US010966701B2

(12) United States Patent
Piskun et al.

(10) Patent No.: US 10,966,701 B2
(45) Date of Patent: Apr. 6, 2021

(54) TISSUE RETRACTOR FOR MINIMALLY INVASIVE SURGERY

(71) Applicant: Boston Scientific Scimed, Inc., Maple Grove, MN (US)

(72) Inventors: Gregory Piskun, Morganville, NJ (US); Brian Tang, Fremont, CA (US); Jeffrey Peter Radziunas, Wallingford, CT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 151 days.

(21) Appl. No.: 15/148,999

(22) Filed: May 6, 2016

(65) Prior Publication Data
US 2016/0278757 A1 Sep. 29, 2016

Related U.S. Application Data

(63) Continuation-in-part of application No. 14/714,287, filed on May 16, 2015, which is a continuation-in-part (Continued)

(51) Int. Cl.
*A61B 17/02* (2006.01)
*A61B 1/00* (2006.01)
(Continued)

(52) U.S. Cl.
CPC ...... *A61B 17/0218* (2013.01); *A61B 1/00066* (2013.01); *A61B 1/00082* (2013.01); (Continued)

(58) Field of Classification Search
CPC ............ A61B 17/0218; A61B 1/00085; A61B 1/2736; A61B 1/32
See application file for complete search history.

(56) References Cited

U.S. PATENT DOCUMENTS

| 457,787 A | 8/1891 | Leisenring |
| 1,621,159 A | 3/1927 | Evans |

(Continued)

FOREIGN PATENT DOCUMENTS

| CN | 100452044 C | 1/2009 |
| CN | 100462044 C | 2/2009 |

(Continued)

OTHER PUBLICATIONS

European Search Report dated Jun. 1, 2014 for International Application No. PCT/US2014/040429.

(Continued)

*Primary Examiner* — Olivia C Chang
(74) *Attorney, Agent, or Firm* — Kacvinsky Diasak Bluni PLLC

(57) ABSTRACT

Improved methods and devices for performing an endoscopic surgery including a system for performing minimally invasive procedures including a flexible catheter having a working space expanding system positioned at a distal portion, the working space expanding system movable from a non-expanded insertion position to an expanded position forming an expanded region to expand the working space within the body lumen. A tissue retractor having an inner member positioned within an outer guide member has a plurality of closed loops at a distal portion forming a petal-like structure. The loops are positioned in a collapsed position within the outer guide member and are movable to an expanded position when exposed from the outer guide member.

13 Claims, 42 Drawing Sheets

Related U.S. Application Data of application No. 14/622,831, filed on Feb. 14, 2015, which is a continuation-in-part of application No. 13/913,466, filed on Jun. 9, 2013, now Pat. No. 9,186,131, which is a continuation-in-part of application No. 12/970,604, filed on Dec. 16, 2010, now Pat. No. 8,506,479, which is a continuation-in-part of application No. 13/531,477, filed on Jun. 22, 2012, now Pat. No. 8,932,211.

(60) Provisional application No. 61/287,077, filed on Dec. 16, 2009.

(51) Int. Cl.
| | |
|---|---|
| *A61B 1/018* | (2006.01) |
| *A61B 1/31* | (2006.01) |
| *A61B 1/313* | (2006.01) |
| *A61B 1/32* | (2006.01) |
| *A61B 17/00* | (2006.01) |
| *A61B 17/128* | (2006.01) |
| *A61M 25/10* | (2013.01) |
| *A61B 17/34* | (2006.01) |

(52) U.S. Cl.
CPC ...... *A61B 1/00085* (2013.01); *A61B 1/00087* (2013.01); *A61B 1/00135* (2013.01); *A61B 1/00154* (2013.01); *A61B 1/018* (2013.01); *A61B 1/31* (2013.01); *A61B 1/313* (2013.01); *A61B 1/32* (2013.01); *A61B 17/00234* (2013.01); *A61B 17/1285* (2013.01); *A61B 2017/00269* (2013.01); *A61B 2017/00287* (2013.01); *A61B 2017/00557* (2013.01); *A61B 2017/00818* (2013.01); *A61B 2017/0225* (2013.01); *A61B 2017/345* (2013.01); *A61M 25/1011* (2013.01); *A61M 2025/1052* (2013.01)

(56) References Cited

U.S. PATENT DOCUMENTS

| | | | |
|---|---|---|---|
| 3,517,128 | A | 6/1970 | Hines |
| 4,040,413 | A | 8/1977 | Ohshiro |
| 4,083,369 | A | 4/1978 | Sinnreich |
| 4,224,929 | A | 9/1980 | Furihata |
| 4,295,464 | A | 10/1981 | Shihata |
| 4,519,403 | A | 5/1985 | Dickhudt |
| 4,611,594 | A | 9/1986 | Grayhack et al. |
| 4,710,171 | A | 12/1987 | Rosenberg |
| 4,966,596 | A | 10/1990 | Kuntz et al. |
| 5,025,778 | A | 6/1991 | Silverstein |
| 5,059,199 | A | 10/1991 | Okada |
| 5,087,265 | A | 2/1992 | Summers |
| 5,112,310 | A | 5/1992 | Grobe |
| 5,197,971 | A | 3/1993 | Bonutti |
| 5,386,817 | A | 2/1995 | Jones |
| 5,411,508 | A | 5/1995 | Bessler et al. |
| 5,423,830 | A | 6/1995 | Schneebaum et al. |
| 5,655,698 | A | 8/1997 | Yoon |
| 5,716,321 | A | 2/1998 | Kerin et al. |
| 5,722,103 | A | 3/1998 | Walega |
| 5,776,097 | A | 7/1998 | Massoud |
| 5,947,983 | A | 9/1999 | Solar et al. |
| 5,954,731 | A | 9/1999 | Yoon |
| 5,997,547 | A | 12/1999 | Nakao et al. |
| 6,009,877 | A | 1/2000 | Edwards |
| 6,042,596 | A | 3/2000 | Bonutti |
| 6,119,913 | A | 9/2000 | Adams et al. |
| 6,142,931 | A | 11/2000 | Kaji |
| 6,142,933 | A | 11/2000 | Longo et al. |
| 6,203,552 | B1 | 3/2001 | Bagley et al. |
| 6,214,024 | B1 | 4/2001 | Houser |
| 6,264,086 | B1 | 7/2001 | McGuckin et al. |
| 6,302,311 | B1 | 10/2001 | Adams et al. |
| 6,343,731 | B1 | 2/2002 | Adams et al. |
| 6,405,732 | B1 | 6/2002 | Edwards |
| 6,423,058 | B1 | 7/2002 | Edwards et al. |
| 6,428,473 | B1 | 8/2002 | Leonard et al. |
| 6,494,881 | B1 | 12/2002 | Bales et al. |
| 6,616,603 | B1 | 9/2003 | Fontana |
| 6,695,198 | B2 | 2/2004 | Adams et al. |
| 6,805,273 | B2 | 10/2004 | Bilotti et al. |
| 6,808,491 | B2 | 10/2004 | Kortenbach et al. |
| 6,840,423 | B2 | 1/2005 | Adams et al. |
| 6,866,178 | B2 | 3/2005 | Adams et al. |
| 6,874,669 | B2 | 4/2005 | Adams et al. |
| 6,913,610 | B2 | 7/2005 | Nakao |
| 6,923,806 | B2 | 8/2005 | Hooven et al. |
| 6,938,814 | B2 | 9/2005 | Sharma et al. |
| 7,014,646 | B2 | 3/2006 | Adams et al. |
| 7,059,331 | B2 | 6/2006 | Adams et al. |
| 7,169,115 | B2 | 6/2007 | Nobis et al. |
| 7,276,066 | B2 | 10/2007 | Ouchi |
| 7,396,329 | B2 | 7/2008 | Nakao |
| 7,445,598 | B2 | 11/2008 | Orban |
| 7,918,787 | B2 | 4/2011 | Saadat |
| 7,959,559 | B2 | 6/2011 | Yamaya |
| 8,007,508 | B2 | 8/2011 | Cox |
| 8,277,373 | B2 | 10/2012 | Maahs et al. |
| 8,506,479 | B2 | 8/2013 | Piskun et al. |
| 8,517,933 | B2 | 8/2013 | Mohr |
| 8,608,652 | B2 | 12/2013 | Voegele et al. |
| 8,764,630 | B2 | 7/2014 | Yamatani |
| 8,777,961 | B2 | 7/2014 | Cabrera et al. |
| 8,932,326 | B2 | 1/2015 | Riina et al. |
| 8,979,884 | B2 | 3/2015 | Milsom et al. |
| 9,050,004 | B2 | 6/2015 | Diao et al. |
| 9,161,746 | B2 | 10/2015 | Piskun et al. |
| 9,168,053 | B2 | 10/2015 | Cox |
| 9,259,233 | B2 | 2/2016 | Gruber et al. |
| 9,370,379 | B2 | 6/2016 | Osman |
| 9,375,224 | B2 | 6/2016 | Jansen |
| 9,661,984 | B2 | 5/2017 | Piskun |
| 2001/0004947 | A1 | 6/2001 | Lemke et al. |
| 2001/0047169 | A1 | 11/2001 | McGuckin, Jr. et al. |
| 2001/0049497 | A1 | 12/2001 | Kalloo et al. |
| 2001/0056260 | A1 | 12/2001 | Grimes et al. |
| 2002/0123748 | A1 | 9/2002 | Edwards et al. |
| 2002/0183593 | A1 | 12/2002 | Chin et al. |
| 2002/0193660 | A1 | 12/2002 | Weber et al. |
| 2003/0023143 | A1 | 1/2003 | Abe et al. |
| 2003/0050663 | A1 | 3/2003 | Khachin et al. |
| 2003/0074015 | A1 | 4/2003 | Nakao |
| 2003/0135230 | A1 | 7/2003 | Massey et al. |
| 2003/0225432 | A1 | 12/2003 | Baptiste et al. |
| 2003/0225433 | A1 | 12/2003 | Nakao |
| 2004/0034278 | A1 | 2/2004 | Adams |
| 2004/0082859 | A1 | 4/2004 | Schaer |
| 2004/0158263 | A1 | 8/2004 | McAlister et al. |
| 2004/0204725 | A1 | 10/2004 | Bayer |
| 2004/0210116 | A1 | 10/2004 | Nakao |
| 2004/0249367 | A1 | 12/2004 | Saadat et al. |
| 2005/0177105 | A1 | 8/2005 | Shalev |
| 2005/0234297 | A1 | 10/2005 | Devierre |
| 2005/0234299 | A1 | 10/2005 | Eitenmuller et al. |
| 2005/0240147 | A1 | 10/2005 | Makower et al. |
| 2005/0251111 | A1 | 11/2005 | Saito et al. |
| 2005/0251177 | A1 | 11/2005 | Saadat et al. |
| 2005/0272977 | A1 | 12/2005 | Saadat et al. |
| 2005/0273085 | A1 | 12/2005 | Hinman et al. |
| 2006/0074277 | A1 | 4/2006 | Yoshida |
| 2006/0100480 | A1 | 5/2006 | Ewers et al. |
| 2006/0189845 | A1 | 8/2006 | Maahs et al. |
| 2006/0191975 | A1 | 8/2006 | Adams et al. |
| 2006/0247662 | A1 | 11/2006 | Schwartz |
| 2006/0264706 | A1 | 11/2006 | Piskun |
| 2007/0005093 | A1 | 1/2007 | Cox |
| 2007/0021778 | A1 | 1/2007 | Carly |
| 2007/0255207 | A1 | 11/2007 | Hangai et al. |
| 2007/0287886 | A1 | 12/2007 | Saadat |
| 2007/0287889 | A1 | 12/2007 | Mohr |

(56) References Cited

U.S. PATENT DOCUMENTS

| | | |
|---|---|---|
| 2007/0293724 A1 | 12/2007 | Saadat et al. |
| 2008/0045842 A1 | 2/2008 | Furnish et al. |
| 2008/0051629 A1 | 2/2008 | Sugiyama et al. |
| 2008/0058590 A1 | 3/2008 | Saadat et al. |
| 2008/0132835 A1 | 6/2008 | Nagamatsu et al. |
| 2008/0161645 A1 | 7/2008 | Goldwasser et al. |
| 2008/0188868 A1 | 8/2008 | Weitzner et al. |
| 2008/0228209 A1 | 9/2008 | DeMello et al. |
| 2008/0249534 A1 | 10/2008 | Gruber et al. |
| 2008/0262492 A1 | 10/2008 | Lee |
| 2008/0269557 A1 | 10/2008 | Marescaux et al. |
| 2008/0269559 A1 | 10/2008 | Miyamoto et al. |
| 2008/0275300 A1 | 11/2008 | Rothe et al. |
| 2008/0300454 A1 | 12/2008 | Goto |
| 2009/0018500 A1 | 1/2009 | Carter et al. |
| 2009/0030369 A1 | 1/2009 | Nagamatsu et al. |
| 2009/0149716 A1 | 6/2009 | Diao et al. |
| 2009/0156996 A1 | 6/2009 | Milsom et al. |
| 2009/0287046 A1 | 11/2009 | Yamatani |
| 2009/0312645 A1 | 12/2009 | Weitzner et al. |
| 2010/0010296 A1 | 1/2010 | Piskun et al. |
| 2010/0049137 A1 | 2/2010 | Fischer, Jr. |
| 2010/0106240 A1 | 4/2010 | Duggal et al. |
| 2010/0152590 A1 | 6/2010 | Moore et al. |
| 2011/0065985 A1 | 3/2011 | Wehrheim |
| 2011/0077498 A1 | 3/2011 | McDaniel |
| 2011/0160538 A1 | 6/2011 | Ravikumar et al. |
| 2011/0172491 A1 | 7/2011 | Piskun et al. |
| 2011/0224494 A1 | 9/2011 | Piskun et al. |
| 2011/0245858 A1 | 10/2011 | Milsom et al. |
| 2011/0306832 A1 | 12/2011 | Bassan et al. |
| 2012/0053485 A1 | 3/2012 | Bloom |
| 2012/0083797 A1 | 4/2012 | Cabrera et al. |
| 2012/0095498 A1 | 4/2012 | Stefanchik et al. |
| 2012/0109178 A1 | 5/2012 | Edwards et al. |
| 2012/0165604 A1 | 6/2012 | Stokes et al. |
| 2013/0090527 A1 | 4/2013 | Axon |
| 2013/0172828 A1 | 7/2013 | Kappel et al. |
| 2013/0274553 A1 | 10/2013 | Piskun et al. |
| 2013/0317303 A1 | 11/2013 | Deshmukh et al. |
| 2013/0324795 A1 | 12/2013 | Nakajima et al. |
| 2014/0316379 A1 | 10/2014 | Sonderegger et al. |
| 2015/0150436 A1 | 6/2015 | Cornhill et al. |
| 2015/0157192 A1 | 6/2015 | Piskun et al. |
| 2015/0265268 A1 | 9/2015 | Diao et al. |
| 2015/0265818 A1 | 9/2015 | Piskun et al. |
| 2015/0272564 A1 | 10/2015 | Piskun et al. |
| 2015/0351890 A1 | 12/2015 | Levin et al. |
| 2016/0038172 A1 | 2/2016 | Cox |
| 2016/0081702 A1 | 3/2016 | Kan et al. |
| 2016/0106466 A1 | 4/2016 | Gruber et al. |
| 2016/0157843 A1 | 6/2016 | Dickson et al. |
| 2016/0374658 A1 | 12/2016 | Piskun |

FOREIGN PATENT DOCUMENTS

| | | |
|---|---|---|
| CN | 201200436 | 3/2009 |
| CN | 102018493 | 4/2011 |
| CN | 102695541 A | 9/2012 |
| CN | 103340679 A | 10/2013 |
| CN | 104135972 A | 11/2014 |
| EP | 0163502 A2 | 12/1985 |
| EP | 1588670 | 10/2005 |
| EP | 2512577 A2 | 10/2012 |
| GB | 2365340 | 2/2002 |
| JP | S63292935 A | 11/1988 |
| JP | H08317928 A | 12/1996 |
| JP | H08336538 A | 12/1996 |
| JP | 2533732 | 4/1997 |
| JP | H1028691 A | 2/1998 |
| JP | 2000166936 A | 6/2000 |
| JP | 2000-325303 | 11/2000 |
| JP | 2001527429 A | 12/2001 |
| JP | 2004529708 A | 9/2004 |
| JP | 2005/046274 | 2/2005 |
| JP | 2007511247 A | 5/2007 |
| JP | 2008528239 A | 7/2008 |
| JP | 2008536552 A | 9/2008 |
| JP | 2010511440 A | 4/2010 |
| JP | 2012075908 A | 4/2012 |
| JP | 2013514827 A | 5/2013 |
| WO | WO 91/01773 | 2/1991 |
| WO | WO 9635469 | 11/1996 |
| WO | 9640347 A1 | 12/1996 |
| WO | 03000139 A1 | 1/2003 |
| WO | 2004103430 A2 | 12/2004 |
| WO | 2006110275 A2 | 10/2006 |
| WO | 2007081601 A2 | 7/2007 |
| WO | WO 2008/011163 | 1/2008 |
| WO | WO 2009/059296 | 5/2009 |
| WO | WO 2009/076176 | 6/2009 |
| WO | WO 2009/117696 | 9/2009 |
| WO | WO 2011/084616 | 7/2011 |
| WO | 2012068048 A1 | 5/2012 |
| WO | WO 2013/050880 | 11/2013 |
| WO | WO 2013/192116 | 12/2013 |
| WO | 2014164661 A | 10/2014 |
| WO | 2014200737 A1 | 12/2014 |
| WO | WO 2015/026968 | 2/2015 |
| WO | 2015191125 A1 | 12/2015 |

OTHER PUBLICATIONS

European Search Report dated May 3, 2011 for European Patent Application No. 06789411.3.
Written Opinion dated Jun. 20, 2007 for International Application No. PCT/US06/30464.
Chinese Office Action dated May 12, 2009 for Chinese Application No. 200680028706.2.
International Search Report and Written Opinion dated May 6, 2016 for International Application No. PCT/US2016/016911.
PCT Search Report dated Jul. 18, 2016 for PCT Application No. PCT/US2016/031355.
International Search Report and Written Opinion for PCT application No. PCT/US17/50685, dated Dec. 14, 2017, 16 pages.
International Search Report and Written Opinion dated May 9, 2018, for PCT/US17/68991 (13 pages).
European Communication for European Patent Application No. 14733912.1, dated Jun. 11, 2018, 2 pages.
International Search Report and Written Opinion for International Application No. PCT/US18/14388, dated Jun. 19, 2018, 9 pages.
International Search Report and Written Opinion for PCT/US10/60802, dated Aug. 24, 2011, 12 pages.
International Search Report and Written Opinion for International Application No. PCT/US18/21779, dated Jun. 14, 2018, 10 pages.
"*Sergey Kantsevoy* vs. *LumenR LLC*, Answer, Affirmative Defenses and Counterclaims", Civil Action No. 17-CV-359 (ELH), filed Feb. 28, 2017, 25 pages.
"Letter from Kurt W. Lockwood, Principal at Kacvinsky Daisak Bluni pllc, to Philip G. Hampton, II c/o Haynes and Boone, LLP" dated Nov. 9, 2018, 16 pages.
"Letter from Philip G. Hampton, II at Haynes and Boone, LLP to Kurt W. Lockwood, Esq. at Kacvinsky Daisak Bluni PLLC", dated Nov. 16, 2018, 2 pages.
"*Sergey Kantsevoy* v. *LumenR LLC* Complaint, Civil Action No. 17-359", filed Feb. 7, 2017, 18 pages.
"*Sergey Kantsevoy* v. *LumenR LLC*, Dr. Sergey Kantsevoy's Answer to LumenR LLC's Counterclaims", Civil Action No. 17-359 (ELH), filed Mar. 17, 2017, 8 pages.
"*Oleg Shikhman* vs. *Bobcat Endoscopy, LLC* (F/K/A/ LumenR LLC) and Gregory Piskun, M.D. Complaint", filed on Oct. 17, 2017, at Judicial District of Fairfield at Bridgeport, 25 pages.
"*Oleg Shikhman* vs. *Bobcat Endoscopy, LLC* (F/K/A/ LumenR LLC) and Gregory Piskun, M.D. Reply to Affirmative Defenses, Matters in Avoidance and Answer to Counterclaims", dated Dec. 12, 2018, 19 pages.
"*Oleg Shikhman* vs. *Bobcat Endoscopy, LLC* (F/K/A/ LumenR LLC) and Gregory Piskun, M.D., Answer, Special Defenses and Counterclaims", dated Sep. 13, 2018, 23 pages.

(56) References Cited

OTHER PUBLICATIONS

"*Oleg Shikhman* vs. *Bobcat Endoscopy, LLC* (F/K/A/ LumenR LLC) and Gregory Piskun, M.D., First Amended Answer, Affirmative Defenses and Counterclaims", dated Nov. 9, 2018, 24 pages.
"Letter from Jeffrey M. Chamberlain, Senior Principal at Kacvinsky Daisak Bluni pllc to Michael J. Rye, Esq. c/o Cantor Colburn, LLP", dated Nov. 13, 2018, 3 pages.
"Letter from Michael J. Rye, Partner at Cantor Colburn LLP to Michael Mahoney, CEO at Boston Scientific Corporation", dated Oct. 17, 2017, 3 pages.
Letter from Michael J. Rye, Partner at Cantor Colburn LLP to Jeffrey M. Chamberlain at Kacvinsky Daisak Bluni PLLC, dated Aug. 28, 2018, 2 pages.
European Search Report for the European Patent Application No. EP19214960, dated Apr. 17, 2020, 6 pages.
*Oleg Shikhman* v. *Bobcat Endoscopy LLC, et al.*, Memorandum of Decision, filed Oct. 31, 2019, 22 pages. (p. 1, line 15—p. 2, line 3; p. 2, lines 7-8, p. 7, lines 4-6; p. 8, lines 3-13; p. 10, line 4—p. 11, line 9; p. 18, line 5—p. 19, line 2; p. 18. footnote 15.)

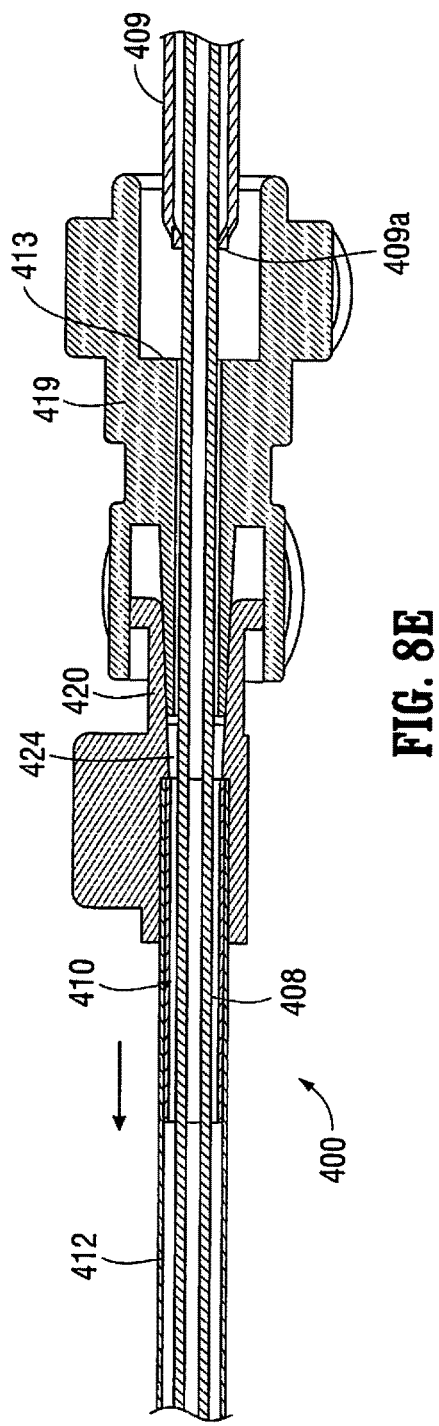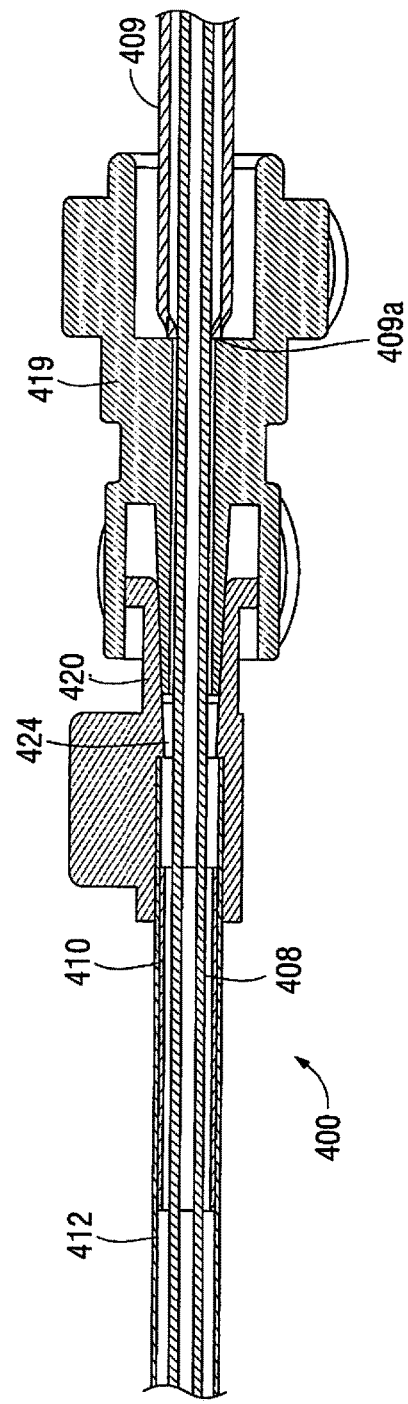
FIG. 8E
FIG. 8F

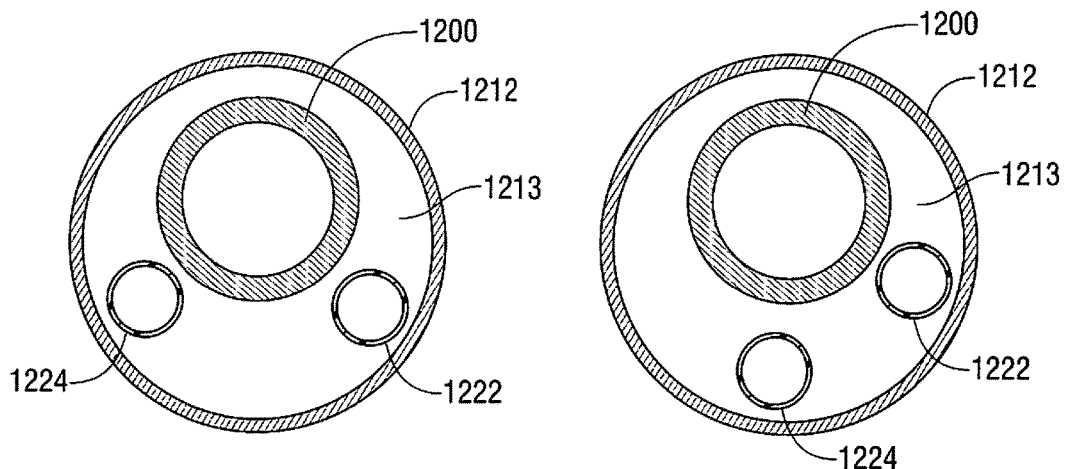
FIG. 37A  FIG. 37B
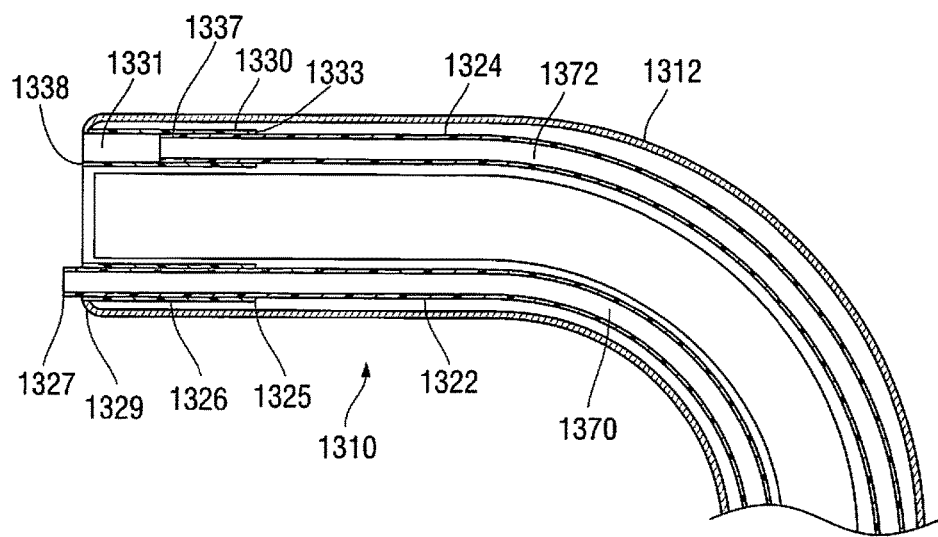
FIG. 38

TISSUE RETRACTOR FOR MINIMALLY INVASIVE SURGERY

This application is a continuation in part of application Ser. No. 14/714,287, filed May 16, 2015, which is a continuation in part of application Ser. No. 14/622,831, filed Feb. 14, 2015 which is a continuation in part of application Ser. No. 13/913,466, filed Jun. 9, 2013, now U.S. Pat. No. 9,186,131, which is a continuation in part of application Ser. No. 12/970,604, filed Dec. 16, 2010, now U.S. Pat. No. 8,506,479, which claims priority from provisional application Ser. No. 61/287,077, filed Dec. 16, 2009, and is a continuation in part of application Ser. No. 13/531,477, filed Jun. 22, 2012, now U.S. Pat. No. 8,932,211. The entire contents of each of these applications are incorporated herein by reference.

BACKGROUND

Field of the Invention

This application is directed to a tissue retractor and more particularly to a tissue retractor for use in an endoluminal system.

Description of the Related Art

Endoscopic procedures involving the gastrointestinal system offer advantages over conventional surgery in that they are less invasive and may provide visualization.

One current problem with endoscopic systems within the gastrointestinal system includes a lack of technology for an optimal minimally-invasive expansion of a stable, working space adjacent to the target tissues. Having the ability to effectively expand and optimally reconfigure (reshape) the working space could markedly facilitate an intra-luminal operation. A better expanded, stable and optimally configured working space may facilitate the instruments and endoscope to be independently manipulated and better visualized around the working space. One of skill would appreciate having the ability to better see and approach both the target tissue and the surrounding anatomy for reference, orientation, and surgical maneuvering.

Another current problem includes a lack of an endoscopic technology for not only expanding, but also affixing and reshaping, both the target tissue and surrounding tissue. In a bowel, for example, such a stable operative space could include a space that is non or less collapsible, with limited peristalsis or aperistaltic, and/or affixed at a particular point in the abdominal cavity. The fixed point can be considered fixed in relation to, for example, a fixed body point in the patient, such as the patient's hip. Significant bowel wall movement is undesirable during an intra-luminal operation on the bowel, for example, since it may create a challenging, unstable operative environment. Such bowel wall movement is normal, of course, even in a sedated patient and can be caused, for example, by bowel collapse from an air leak, peristalsis, breathing, and movement of the scope and instruments. Having a technology to overcome this problem would help provide a stable operative space, which is clinically desired by one of skill in the operative environment.

Another current problem includes a lack of an endoscopic technology for retracting the tissue dynamically, for example, through an adjustable tissue retraction structure allowing for a controlled degree of expansion or collapse of the structure, to further expand or configure the working space as desired around the instruments and target tissue. Such control can effectively provide for a method of adjusting the retractor, as well as tissue placement, in-and-around the working space. By increasing and releasing the tension on the retractor, the tissue in the working space, for example, can be better visualized and controlled during a procedure. Moreover, the tissue retraction and, particularly, traction-contra-traction can be facilitated to help create a desired dissecting plane or position the tissue more optimally during an operation. Having a technology to overcome this problem would help create an operative environment that is more desirable for tissue dissection, retraction, cutting and a removal of tissue.

Another current problem includes a lack of an endoscopic technology for organizing the endoscope, instruments, and working space in a manner that can optimize the relative positions inside the working space for the treatment. The larger working space can improve the ability to manipulate the instruments and endoscope in a minimally-invasive manner. Namely, one of skill would like to have a working space that has a point of entry for the instruments that is sufficiently far away from the target tissue to provide flexibility in approaching and visualizing the target tissue, perhaps providing more operating room for selecting a trajectory of the instruments toward the target tissue that is, for example, at least substantially perpendicular to the plane of dissection of the target tissue. Having a technology to overcome this problem would provide the person of skill with a system and procedure that is more desirable for a removal of tissue.

Another current problem includes lack of an endoscopic technology for manipulating, e.g., retracting, bulky tissue inside or away from the operating field which would otherwise obscure the operating field and thereby make performance of the surgical procedure within the working space more difficult.

In view of at least the above, one of skill in the art of endoscopic, gastrointestinal surgical treatments would appreciate the technology taught herein which provides one or more of (i) a minimally-invasive expansion of the intra-luminal working space; (ii) an affixing, of both the target tissue and surrounding tissue to help provide a stable, operative space; (iii) a retracting of the tissue dynamically, allowing for a partial or complete expansion or collapse, to further configure the working space between the instruments and the target tissue; (iv) an organization of the endoscope instruments, such as the retractor and tools to maximize the working space and maneuverability, allowing for a maximum flexibility in approaching and visualizing the target tissue, including enabling triangulation and (v) a tissue retractor system for moving bulky tissue inside and away from the operating field which would otherwise obscure the field. It should be appreciated that having such improvements would reduce the technical complexity, and increase the efficacy and safety of, otherwise complex endoscopic operations. Moreover, doing so at a low cost, while using an affordable system that is introduced in the subject atraumatically and in a manner that does not substantially disrupt the conventional endoscopy workflow, would be seen by those of skill as a very substantial advancement in the field of endoscopic surgical procedures.

SUMMARY

The teachings provided herein are generally directed to improved methods and devices for operatively treating gastrointestinal disorders endoscopically in a stable, yet dynamic operative environment, and in a minimally-invasive manner. The systems, for example, include an endoscopic surgical suite. The surgical suite can have a reversibly-expandable retractor that expands to provide a stable, operative environment within the body lumen. The expansion can be asymmetric to maximize space for instruments to be maneuvered independently to visualize a target tissue and treat the target tissue in a minimally invasive manner. The system provides an increase in distance between tool ports and the target tissue to improve maneuverability and triangulation of the tools with respect to the target tissue, as well as a larger field of view. The system further provides a surgical tool to enhance visibility of the operating field within the surgical suite.

In accordance with one aspect of the present disclosure, a retractor for moving tissue in an endoluminal procedure is provided comprising an outer member, an inner member slidably positioned within the outer member for movement between a proximal position and a distal position, and a plurality of closed loops at a distal portion of the inner member forming a petal-like structure. The loops are positioned in a collapsed position within the outer member when the inner member is in the proximal position and movable to an expanded position upon exposure from the outer member when the inner member is moved to the distal position. In the expanded position, the loops extend in different radial directions and the extent of expansion of the loops in radial directions is controlled by the extent of distal advancement of the inner member within the outer member.

In some embodiments, the retractor includes a retaining mechanism to maintain the inner member in position within the outer member. In some embodiments, the retaining mechanism includes a rotatable member and a clamping member, the clamping member engageable with the inner member, wherein rotation of the rotatable member applies a force to the clamping member which applies a clamping force on the inner member to retain the inner member in position. In other embodiments, the retaining mechanism includes a screw thread wherein rotation of a threaded knob provides incremental advancement of the threaded inner member to control the extent of deployment of the loops of the retractor.

In some embodiments, the loops are composed of shape memory material with a memorized position in the expanded position. The loops can be configured in some embodiments to spring out with a force to a fully expanded position when a sufficient portion of the loops are exposed from within the outer member. In some embodiments, one or more of the loops can be covered with a pliable material.

In accordance with another aspect of the present disclosure, a combination of a tissue retractor and a system for performing minimally invasive procedures in a working space within a body lumen of a patient is provided. The system comprises a flexible catheter having an inner wall, an outer wall and configured and dimensioned to receive a flexible endoscope. A first flexible guide is slidably positioned within the catheter. The catheter has a working space expanding system positioned at a distal portion thereof movable from a non-expanded insertion position to an expanded position forming an expanded region to expand the working space within the body. The distal portion of the first flexible guide is movable to angled positions within the expanded region. The tissue retractor has an outer member, an inner member and a plurality of loops at a distal portion of the inner member, the plurality of loops positioned in a collapsed position within the outer member and movable to an expanded position extending radially in different directions within the working space when exposed from the outer member.

In some embodiments, the system further includes a second flexible guide slidably positioned within the catheter and configured and dimensioned to receive an instrument for axial movement therein, the second flexible guide having a longitudinal axis and a distal portion movable to angled positions with respect to the longitudinal axis of the second flexible guide.

In some embodiments, the catheter further includes a covering for the working space expanding system, the covering having an opening to receive body tissue.

In some embodiments, the tissue retractor is insertable within the first flexible guide. In some embodiments, the tissue retractor is insertable directly through a lumen in the catheter.

The working space expanding system can include a plurality of flexible elements, movable from a collapsed insertion position outwardly away from a longitudinal axis of the flexible catheter to an expanded position. An actuator can be provided positioned at a proximal region of the catheter and operably coupled to the flexible elements to move the plurality of flexible elements between the collapsed and expanded positions.

In accordance with another aspect of the present disclosure, a method for performing a minimally invasive procedure in a working space within a body lumen of a patient is provided comprising a) providing a catheter having a lumen and a working space expanding system at a distal portion; b) expanding the working space expanding system from a non-expanded insertion position to an expanded position forming an expanded cage to expand the working space within the body lumen; c) inserting through the catheter a tissue retractor having a plurality of expandable petals; d) exposing the petals within the working space to enable the petals to move from a collapsed insertion position to an expanded position; e) manipulating the tissue retractor from a proximal end so one or more of the petals contacts and moves tissue away from a tissue dissecting plane that would otherwise obstruct the tissue dissecting plane; and e) dissecting target tissue with a dissecting instrument inserted through the catheter.

In some embodiments, the step of inserting the tissue retractor comprises inserting the retractor directly through a lumen of the catheter. In other embodiments, the method further comprises the step of inserting a first flexible guide through the catheter, and the step of inserting the tissue retractor comprises inserting the tissue retractor through the flexible guide.

The method can further comprise the step of inserting a second flexible guide through the catheter and the dissecting instrument is inserted through the second flexible tube.

The method can further comprise the step of controlling the extent of expansion of the petals of the tissue retractor.

The systems provided herein can be used in several different methods of treatment, such as for example treating a gastrointestinal lesion. The lesion can include, for example, a perforation, a tissue pathology a polyp, a tumor, a bleed, a diverticuli, an ulcer, a cancerous tissue, an abnormal vessel, or an appendix.

In accordance with another aspect, a system for moving tissue in an endoluminal procedure is provided comprising an outer guide member and an inner member mounted within the outer guide member, the inner member having a series of retractor elements at a distal portion, the retractor elements movable from a collapsed position within the outer guide member to an expanded position when exposed from the outer guide member, one or both of the inner member and outer guide member slidable relative to the other member to expose the retractor elements so they move to the expanded position, the outer guide member having a pre-bent distal end such that the distal end is at an angle to a longitudinal axis of the outer guide member, wherein the outer guide member controls lateral movement of the inner member as the pre-bent distal end of the outer guide member effects bending of the distal portion of the inner member to direct the distal portion of the inner member laterally with respect to a longitudinal axis of the inner member, the outer member dimensioned for insertion through a catheter to endoluminally access tissue.

In some embodiments, a first stop limits proximal movement of the inner member and/or a second stop limits distal movement of the inner member. The system can include an internal member positioned external of and coaxial with the inner member, the internal member forming the first stop to limit proximal movement upon contact with an internal reduced diameter structure of a luer fitting. The system can include a hypotube positioned external of and coaxial with the inner member, the hypotube having a handle with an abutment wall forming the second stop engaging an adapter to provide the second stop.

In some embodiments, the retractor elements comprise a series of loops forming a petal-like structure. In some embodiments, in the expanded position the loops extend in different radial directions and the extent of expansion of the loops in radial directions is controlled by the extent of distal advancement of the inner member within the outer guide member. In some embodiments, the loops are composed of shape memory material with a memorized position in the expanded position. In some embodiments, the inner member is a wire and the loops are formed from the wire.

In some embodiments, the system includes a catheter dimensioned to receive the inner member and outer guide member, the catheter including a working space expanding system positioned at a distal portion thereof, and the working space expanding system is movable from a non-expanded insertion position to an expanded position forming an expanded region to expand the working space within the body, and a distal portion of the outer guide member is maneuverable within the working space expanding system. In some embodiments, distal axial movement of the outer guide member increases a lateral distance from an outermost edge of the loops to the longitudinal axis and proximal movement of the outer guide member decreases a lateral distance from the outermost edge of the loops to the longitudinal axis. In some embodiments, the outer guide member is rotatable within the catheter to change the orientation of the loops when exposed from the outer guide member.

In some embodiments, the inner member is substantially straight in a normal condition and is bent by the outer guide member.

In some embodiments, a second outer guide member having a pre-bent angle different than a pre-bent angle of the outer guide member is provided to effect bending of the inner member to a different angle.

In some embodiments, the system includes a flexible catheter having an inner wall and an outer wall and is configured and dimensioned to receive a flexible endoscope, the outer guide member slidably positioned within the catheter. In some embodiments, the catheter further comprises a covering for the working space expanding system, the covering having an opening to receive body tissue.

In accordance with another aspect of the present disclosure, a kit for performing minimally invasive endoluminal procedures in a working space within a body lumen of a patient is provided. The kit comprises a) a flexible catheter having an inner wall, an outer wall and configured and dimensioned to receive a flexible endoscope, b) a first flexible guide for slidable positioning within the catheter, the first flexible guide having a longitudinal axis and a distal portion curved at a first angle with respect to the longitudinal axis, and c) a second flexible guide for slidable positioning within the catheter, the second flexible guide having a longitudinal axis and a distal portion curved at a second angle with respect to the longitudinal axis. The catheter further has a working space expanding system positioned at a distal portion thereof, the working space expanding system movable from a non-expanded insertion position to an expanded position forming an expanded region to expand the working space within the body. The first flexible guide is axially movable within the expanded region to control lateral movement of a first instrument positioned therein and the second flexible guide is axially movable within the expanded region to control lateral movement of a second instrument positioned therein.

In some embodiments, the kit further comprises tissue retractor having a plurality of loops at a distal portion, the plurality of loops positioned in a collapsed position within the first flexible guide and movable to an expanded position extending radially in different directions within the working space when exposed from the first flexible guide. In some embodiments, the tissue retractor is non-removably retained within one of the flexible guides.

In some embodiments, the kit further comprises a third flexible guide for slidably positioning within the catheter, the third flexible guide having a longitudinal axis and a distal portion curved at a third angle with respect to the longitudinal axis of the guide, the third angle being different from the first and second angles.

In some embodiments, the working space expanding system comprises a plurality of flexible elements, wherein the plurality of flexible elements are movable from a collapsed insertion position outwardly away from a longitudinal axis of the flexible catheter to an expanded position. In some embodiments, an actuator is positioned at a proximal region of the flexible catheter and operably coupled to the working space expanding system to move the plurality of flexible elements between the collapsed and expanded positions.

In accordance with another aspect of the present disclosure, a method for performing minimally invasive procedures in a working space within a body lumen of a patient is provided, the method comprising:

providing a catheter having a lumen and a working space expanding system at a distal portion;

expanding the working space expanding system from a non-expanded insertion position to an expanded position forming an expanded chamber to expand the working space within the body lumen;

inserting through the catheter a flexible outer guide member and a tissue retractor slidably positioned within the outer guide member, the tissue retractor having a plurality of expandable petals;

exposing the petals from the outer guide member within the body lumen to enable the petals to move from a collapsed insertion position to an expanded position within the body lumen; and either before or after the step of exposing the petals, moving the outer guide member axially to adjust the lateral extension of the tissue retractor toward the target tissue to adjust a distance from an outermost edge of the retractor to the target tissue.

In some embodiments, the method further comprising the steps of a) manipulating the tissue retractor from a proximal end so one or more of the petals contacts and moves tissue away from a tissue dissecting plane that would otherwise obstruct the tissue dissecting plane and b) dissecting target tissue with a dissecting instrument inserted through the catheter.

BRIEF DESCRIPTION OF THE FIGURES

FIG. 8E is a side view of an alternate embodiment of the retractor deployment mechanism of the present invention in the retracted position FIG. 8F is a side view of the retractor deployment mechanism of FIG. 8E in the extended position.

FIGS. 37A and 37B are transverse cross-sectional views through the outer tube showing radial movement of an intermediate portion of the floating channels within the lumen of the outer tube.

FIG. 38 is a cross-sectional view illustrating bending of the outer tube and movement of the floating channels of FIGS. 35A-35C.

DETAILED DESCRIPTION

Figure 1:
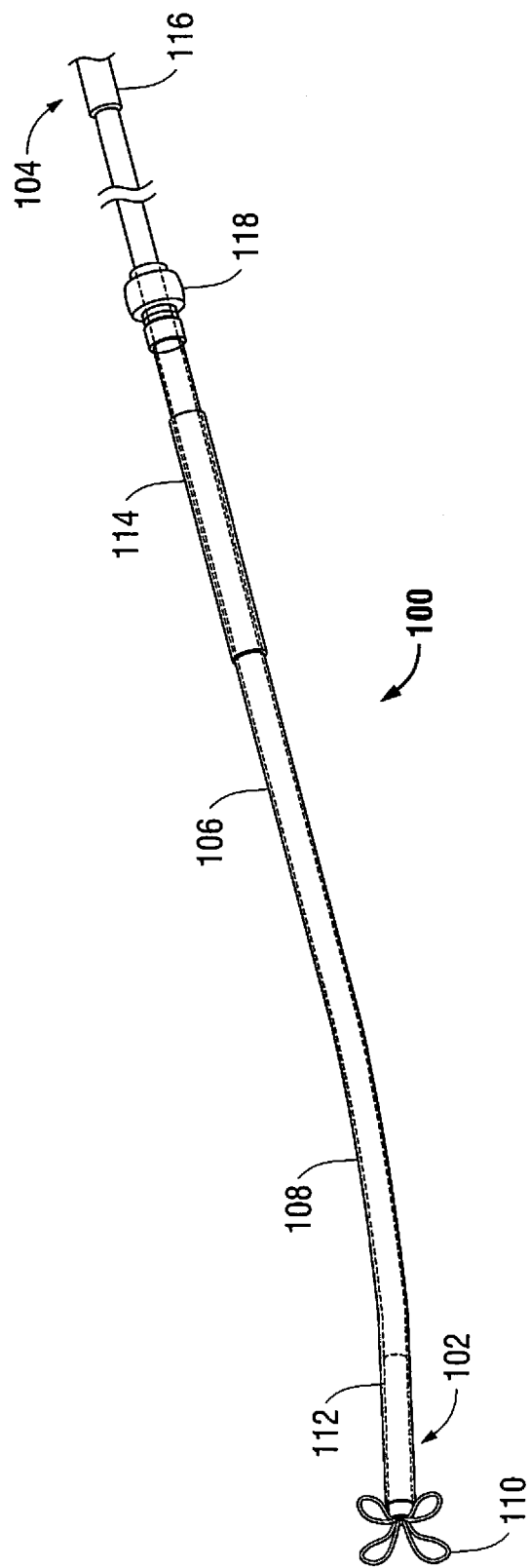
FIG. 1 is a perspective view of one embodiment of a tissue retractor of the present disclosure for moving tissue, the petals (loops) shown in the expanded position.
Figure 2A:
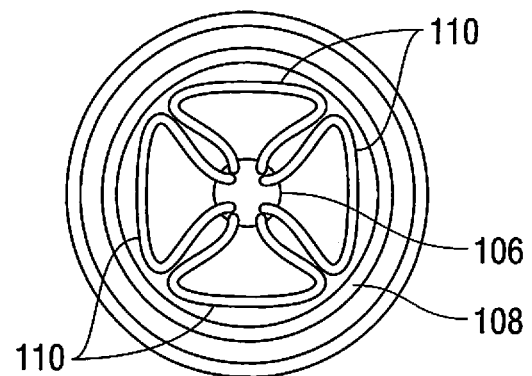
FIG. 2A is a front view of the tissue retractor of FIG. 1 with the petals shown in the collapsed (non-expanded) position.
Figure 2B:
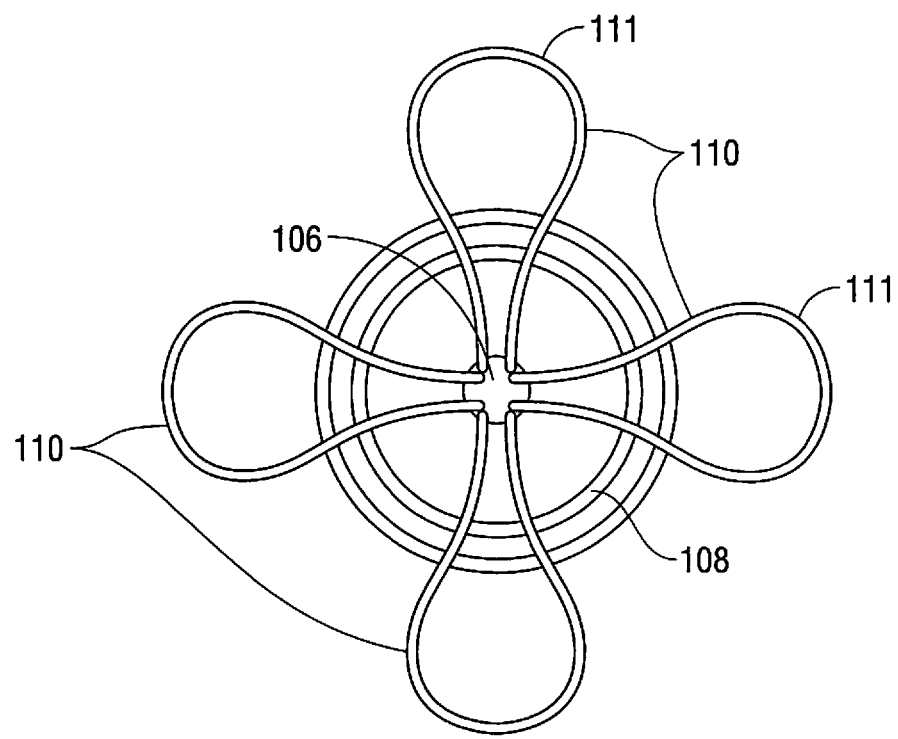
FIG. 2B is a front view of the tissue retractor of FIG. 1 with the petals shown in the expanded position.

The teachings provided herein are generally directed to improved methods and devices for operatively treating gastrointestinal disorders endoscopically in a stable, yet dynamic operative environment, and in a minimally-invasive manner. The systems, for example, include an endoscopic surgical suite that is created by the systems disclosed herein. The surgical suite can have a reversibly-expandable retractor that expands to provide a stable, operative environment within a subject. In some embodiments, the expansion can be asymmetric around a stabilizer subsystem to maximize space for endoscopic tools and in some embodiments an endoscope, to be maneuvered independently treat the target tissue. The systems herein provide an increase in distance between tool ports and the target tissue to enhance the independent maneuverability and triangulation of each of the tools with respect to the target tissue. This increase in distance can also provide a way of obtaining a larger field of view. The systems taught herein, for example, can (i) enable a working space to be dynamically configured around the target tissue in tortuous body lumens and orifices such as the gastrointestinal tract using controls from outside the body; (ii) provide a flexible, passageway for multiple surgical tools and instruments, such as endoscope and graspers to be passed from outside the body towards the target tissues; (iii) organize and/or constrain tools in the working space; (iv) at least substantially immobilize and/or stabilize the target tissue and surrounding tissue for a treatment; and/or (v) enable control over the geometry position, and orientation of the instruments such as the grasper in the working space from outside the body.

In some embodiments disclosed herein, an articulating endoscope is inserted through a channel of the catheter; in other embodiments the system is backloaded over a flexible endoscope, such as a conventional colonoscope, then the endoscope is inserted to a position adjacent the target tissue and then the catheter is advanced over the flexible endoscope so the reshaping (retractor) system (cage) is next to the target tissue.

In some embodiments disclosed herein, the endoscopic working instruments (tools) for treating the target tissue are inserted directly through a respective lumen or channel of the multi-lumen catheter. In these embodiments where the instruments (tools) are inserted directly into the lumen of channel of the catheter, the working instruments can have a curve at a distal end which automatically assumes the curved position when exposed from the catheter so it can curve toward the target tissue, or alternatively, the working instruments can have a mechanism actively controlled by the user to articulate/angle the distal tip. In other embodiments, instead of the endoscopic working instruments (tools) being inserted directly into the channel or lumen of the catheter, a flexible tube is inserted through the lumen or channel of the catheter and acts as a guide for the instrument. That is, the flexible tube is first inserted into the lumen or channel of the catheter and then the endoscopic instrument is inserted through the respective flexible tube. The flexible tube can have a curve at a distal end which automatically assumes the curved position when exposed from the catheter so it can curve toward the target tissue, or alternatively, the flexible tube can have a mechanism actively controlled by the user to articulate/angle the distal tip. In these embodiments utilizing the flexible tubes, the curving and maneuverability of the flexible tubes controls the positioning and orientation of the endoscopic instruments, and therefore the endoscopic instruments need not be provided with a pre-curved tip or articulating mechanisms.

In preferred embodiments, the systems disclosed herein include a retractor which creates an asymmetric working space within the body lumen. More particularly, when working in a confined body lumen, such as the colon, expansion of the lumen is limited because it is undesirable to over-expand which could stretch the lumen beyond its ability to return to its normal state or more dangerously could rupture the lumen. The asymmetric working spaces disclosed herein are designed to expand, and in some instances, reconfigure or reshape the body lumen-transform the cylindrical space within the body lumen to a non-cylindrical asymmetrical space (i.e., changing the geometry) to shift the space around the target tissue to create more working space around the target tissue to provide both visual and mechanical improvements. Stated another way, in a cylindrical working space, there is a lot of area of unused space while in the reshaping of the embodiments disclosed herein the space is moved or shifted to reduce the unused space and create a larger area for tissue access and treatment.

FIGS. 1-8F illustrate embodiments of a tissue retractor of the present disclosure for use with the systems of FIGS. 11-42 disclosed herein. The tissue retractor is configured to gently but firmly push bulky tissue, such as a large polyp, away from the dissection plane (operating field) within the body lumen, e.g., the colon, during the surgical procedure. The tissue retractor is configured to retract bulky tissue which would otherwise obscure the dissection plane during the procedure and might not be able to be sufficiently moved by the jaws of conventional graspers. For example, in certain instances, a large polyp could occupy ½ or even ⅔ of the body lumen, and during the procedure becomes floppier, moving in different directions to obstruct the view of the dissecting plane. The tissue retractor of the present invention provides loops or petals which have sufficient rigidity to move the poly (or other tissue) and provide a relatively large interface between the loops and the polyp (or other tissue) to enhance retraction. The various tissue retractors can be used with the flexible guides (tool channels) described below. Alternatively, they can be used with specialized flexible guides (tool channels) designed specifically for use with the tissue retractor. In either case, the flexible guides preferably have a pre-bent tip to bend the tissue retractor toward the target tissue. Movement of the flexible guides and tissue retractor to provide improved movement and manipulation are described in more detail below.

Figure 4:
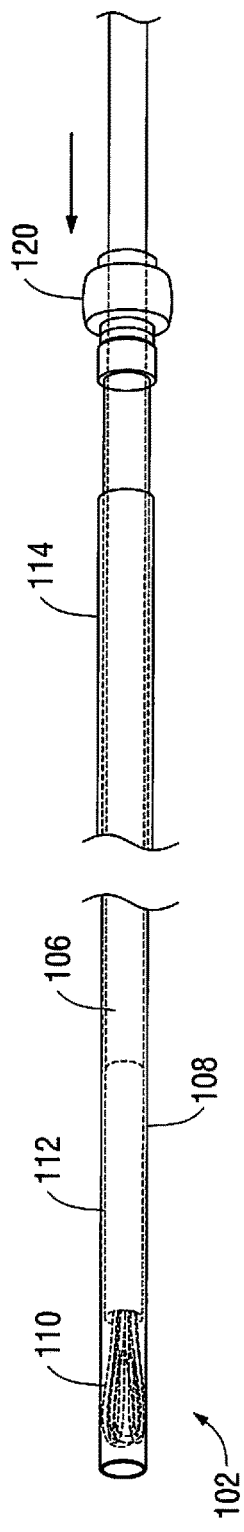
FIG. 4 is a side view of the tissue retractor of FIG. 1 shown with the petals in the collapsed position.
Figure 5:
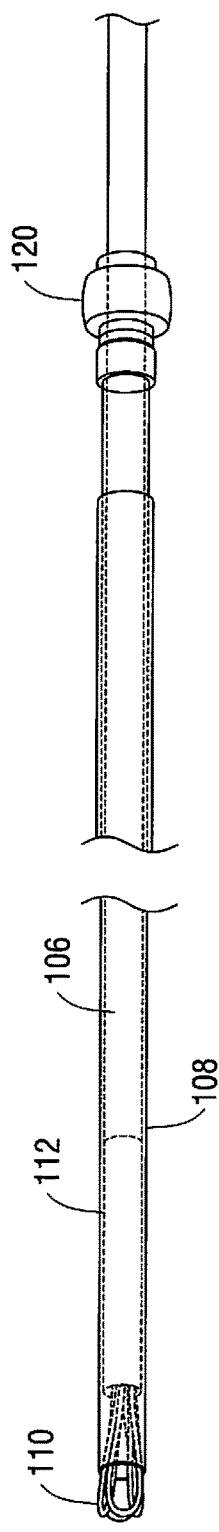
FIG. 5 is a side view similar to FIG. 4 showing initial advancement of the inner shaft to expose a portion of the petals.
Figure 6:
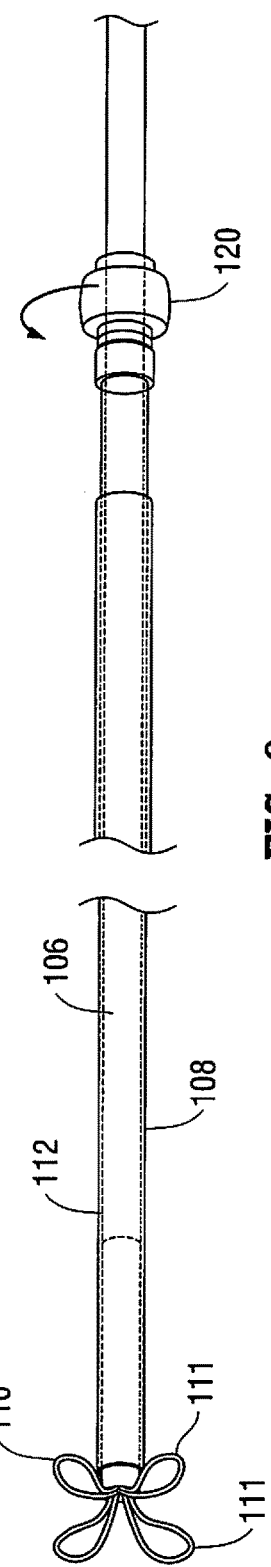
FIG. 6 is a side view similar to FIG. 5 showing further advancement of the inner shaft and full expansion of the petals.

Turning first to FIGS. 1, 2A, 2B and 4-7C, the tissue retractor of this embodiment is designated generally by reference numeral 100 and has a distal portion 102 and a proximal portion 104. An inner shaft (inner member) 106 is slidably positioned within outer tube or sheath (outer member) 108, preferably having a curvature as shown. At the distal end of inner shaft 106 is attached a plurality of closed loops or petals 110. Although four petals (loops) 110 are shown, it should be appreciated that a fewer number or a greater number of petals 110 could be provided. The petals 110 are movable from a collapsed insertion position within the outer tube 108 to an advanced position where they are exposed from the outer tube 108 and can move to the expanded position of FIG. 1. FIG. 4 illustrates the petals 110 in the collapsed (retracted) position and FIGS. 1 and 6 illustrate the petals 110 in their fully expanded position. Note that in the embodiments described herein, the petals 110 are exposed by advancement of the inner shaft 106 relative to the outer tube 108. However, it should be appreciated, that alternatively, the outer tube could be retracted to expose the petals 110 or both the inner shaft could be moved proximally and the outer tube moved distally. In each of these methods, it is the relative movement of the inner shaft and outer tube 110 that exposes the petals 110 for expansion.

A material such as a shrink wrap tube 112 can be attached to a distal portion of the inner shaft 106. This can reinforce the inner shaft 106. The outer tube 108 can have a control surface 114 which provides a larger diameter region. The proximal portion of the inner shaft 106 can have an increased diameter portion 116 which can be formed for example by a shrink wrap or other materials placed over a proximal portion of the inner shaft 106 to "build up" the outer diameter. This improves the grasping of the inner shaft 106 by the user to facilitate movement.

Figure 7A:
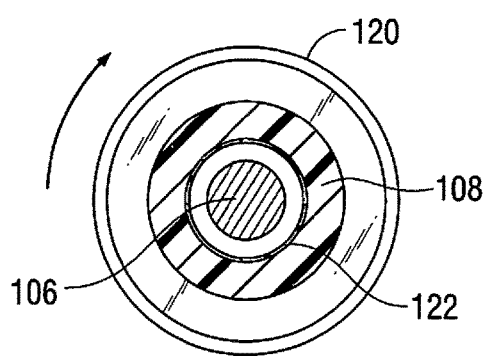
FIG. 7A is a cross-sectional view of the locking mechanism, the locking mechanism shown in the unlocked position.
Figure 7B:
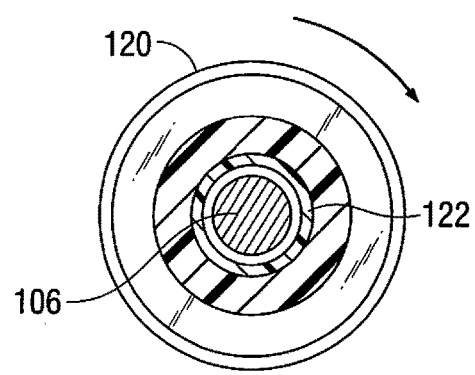
FIG. 7B is a cross-sectional view similar to FIG. 7A showing initial rotation of the locking mechanism.
Figure 7C:
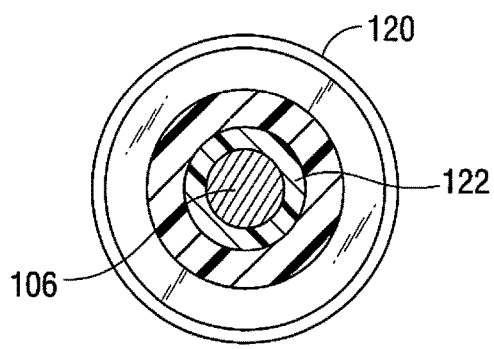
FIG. 7C is a cross-sectional view similar to FIG. 7B showing the locking mechanism in the locked position to clamp the inner shaft.

Tissue retractor 100 includes a locking mechanism 118 to retain the inner shaft 106 in the desired axial position to thereby retain the retractor petals (loops) 110 in the desired expanded position. Locking mechanism 118 includes a rotatable outer knob 120 and an inner circumferential clamping member 122 which either partially or fully surrounds the inner shaft 106. When the outer knob 120 is in the unclamping position, the inner diameter or dimension of the clamping member 122 is of sufficient size to enable free axial sliding movement of the inner shaft 106. This position is shown in FIG. 7A. When the user desires to lock the axial position of the inner shaft 106, the knob 120 is rotated as shown in FIGS. 7A and 7B to the position of FIG. 7C to apply a clamping force on clamping member 122 which thereby reduces its inner diameter and dimension and clamps around inner shaft 106 as shown in FIG. 7C.

Petals 110 are shown in the illustrated embodiment as closed loops. The petals 110 can be formed from wires attached to the inner shaft 106. As noted above, the petals 110 are movable from the collapsed insertion position of FIG. 4 (and FIG. 2A) to the expanded position of FIG. 6 (and FIG. 2B). The petals 110 can be made of shape memory material with a memorized configuration of FIG. 6 so that when exposed from the outer tube 108 they are no longer constrained and return to their expanded memorized position. In some embodiments, the petals 110 are configured to "spring out" once partially exposed. That is, once a sufficient area of the petals 110 is exposed from the outer tube 108, they "spring out" to their expanded position.

In the illustrate embodiments, the petals 110 have a curved outer surface 111 which can be angled with respect to a longitudinal axis of the inner shaft 106. That is, an axis extending through the apex of the loop can be at an angle to the longitudinal axis of the inner shaft 106 so that one or more of the loops 110 are at an angle to the longitudinal axis. Alternatively, the loops can be substantially perpendicular to the longitudinal axis. The loops 11 have sufficiently flexibility to be collapsible for insertion while having sufficient rigidity to move/retract tissue. Various portions of the loops can be utilized to contact and move tissue. The four loops illustrated are the substantially the same size, however, in alternate embodiments, loops of different sizes could be provided.

Figure 3A:
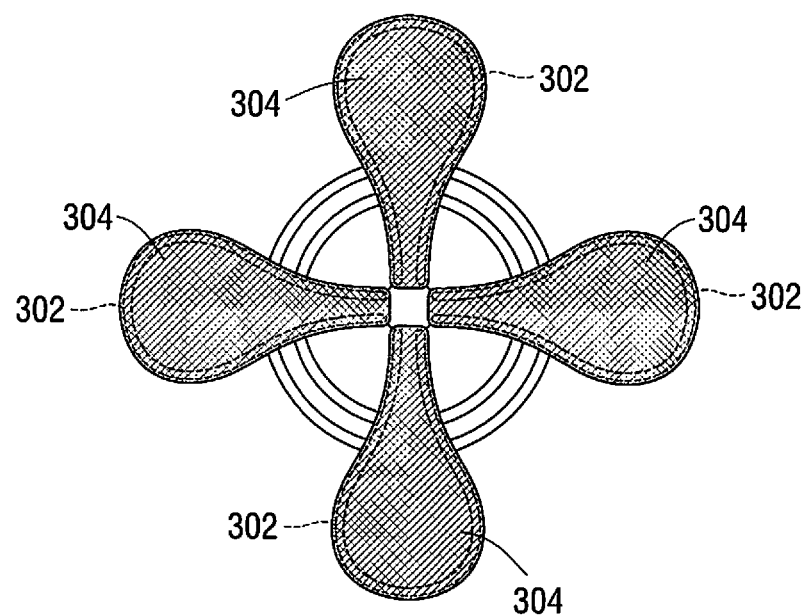
FIG. 3A is a front view of an alternate embodiment of the tissue retractor with the petals shown in the expanded position.
Figure 3B:
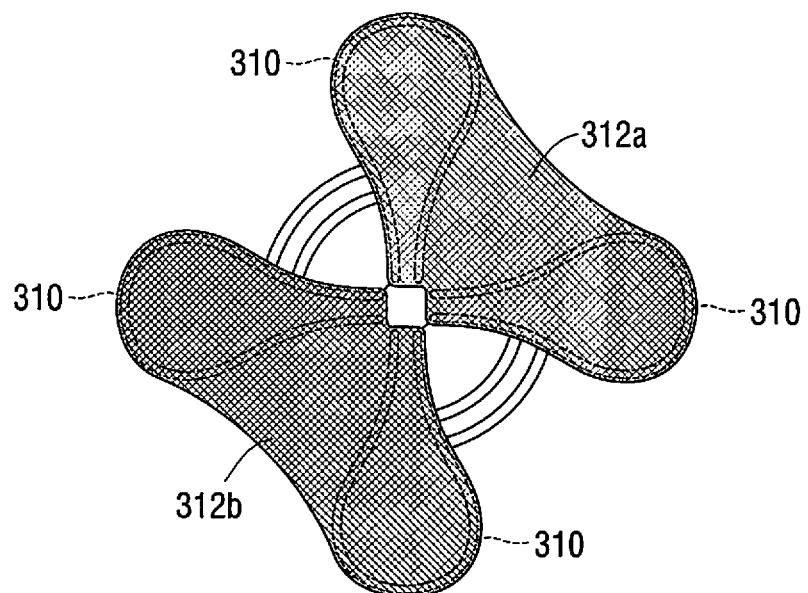
FIG. 3B is a front view of an alternate embodiment of the tissue retractor with the petals shown in the expanded position.

In an alternate embodiment of the tissue retractor shown in FIG. 3A, the loops (petals) 302 are covered with a thin pliable material 304, such as a plastic, cloth or other materials, to provide a barrier to prevent tissue protruding into (through) the loops. Thus, as shown, each loop 302 is covered by a material 304. In another alternate embodiment of the tissue retractor illustrated in FIG. 3B, a thin pliable material 312a covers two of the loops 310 and a thin pliable material 312b covers another two of the loops 310. This material can be a plastic, cloth or other materials. Material 312a and 312b each provide a barrier for protrusion of the tissue into (through) the loops as well as to prevent tissue protruding between the two covered loops. It should also be understood, that in an alternate embodiment, the pliable material described herein can cover all of the loops. Additional, the pliable material described herein can be placed between adjacent loops and not over the loops. Thus, various combinations of intra-loop and inter-loop coverings can be provided. The retractors of FIGS. 3A and 3B (as well as the alternate versions described in this paragraph) in all other respects are the same as the tissue retractor 100 and therefore the discussion of the structure and method of use with respect to retractor 100 is fully applicable to these retractors. Furthermore, the different retention/locking mechanisms can also be utilized with these retractors.

In use, the tissue retractor 100 is inserted through the catheter system which is discussed in detail below. The inner shaft 106 is then advanced relative to the outer tube 108 (FIGS. 5 and 6) to expose the petals 110 as shown in FIG. 6. When the petals 110 are exposed, the user rotates outer knob 118 as shown in FIG. 6 to lock the inner shaft 106 and thus the petals 110 in position.

Figure 8A:
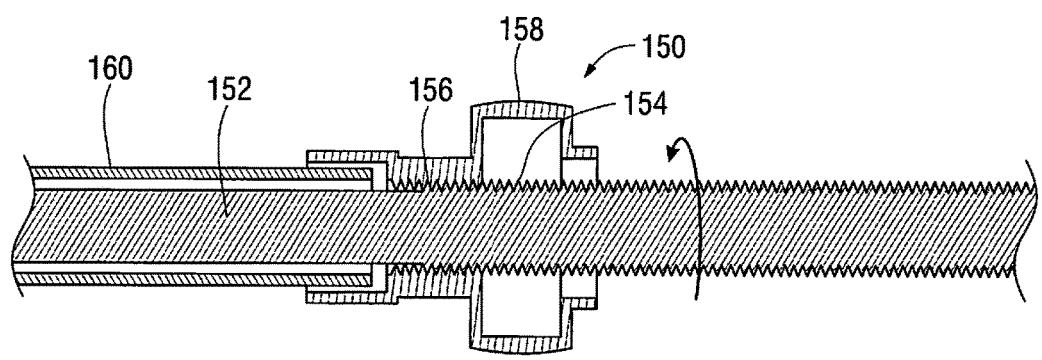
FIG. 8A is a cross-sectional view of an alternate embodiment of an inner shaft advancement mechanism of the present disclosure.
Figure 8B:
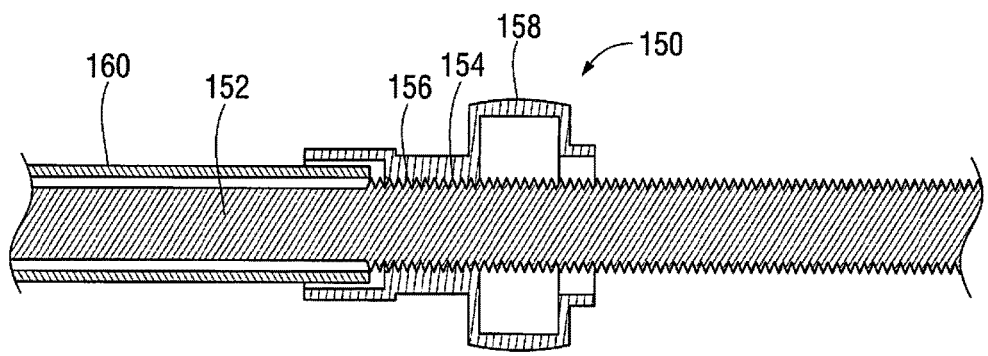
FIG. 8B is a cross-sectional view similar to FIG. 8A showing advancement of the inner shaft due to rotation of the rotatable knob.

FIGS. 8A and 8B illustrate an alternate embodiment of the tissue retractor of the present disclosure. Only the region of the advancement mechanism is shown since the remaining portions of the retractor are identical to the tissue retractor 100 of FIGS. 1-7C and thus the discussion of the other aspects of the retractor 100 are fully applicable to this embodiment. The advancement mechanism 150 of the retractor of FIG. 8A enables the inner shaft to lock at any point along its axial travel so that the petals 110 can be locked at any degree (extent) of expansion. Inner shaft 152 has an outer (external) thread 154 engageable with an internal thread 156 of rotatable knob 158. Rotatable knob 158 is attached to outer tube or sheath 160. When the knob 158 is rotated in a first direction, the threaded engagement with the inner shaft 152 incrementally advances the inner shaft 152. When the user ceases rotation of knob 158, the inner shaft 152 remains fixed in position.

Figure 8C:
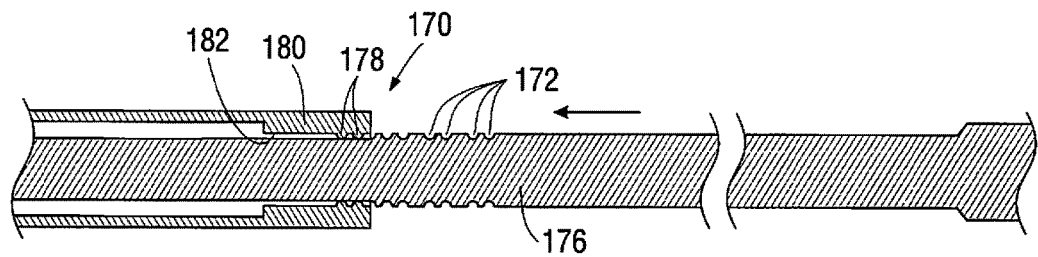
FIG. 8C is a cross-sectional view of an alternate embodiment of an inner shaft retention (locking) mechanism of the present disclosure.
Figure 8D:
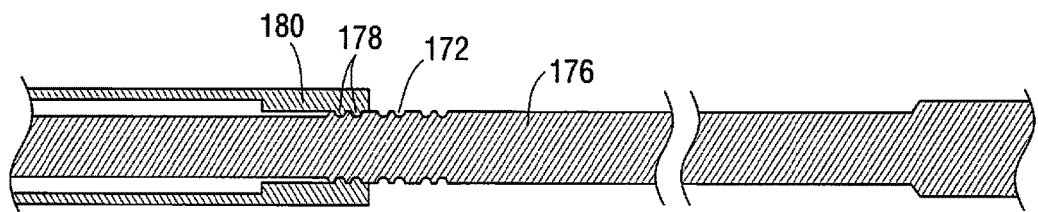
FIG. 8D is a cross-sectional view similar to FIG. 8C showing advancement of the inner shaft to a first retention (locking) position.

In the alternate embodiment of FIGS. 8C and 8D, a series of retention (locking) positions are provided for the inner shaft. The retractor of FIGS. 8C and 8D is identical to retractor 100 except for the retention mechanism 170 so only the region of the retention mechanism 170 is illustrated and discussed as the foregoing discussion of the other aspects of the retractor 100 are fully applicable to this embodiment. The retention mechanism 170 includes a series of grooves or recesses 172 on an outer surface of inner shaft 176 which engage with bumps or projections 178 on inner surface 182 of outer tube or sheath 180 (or on an inner surface of an insert internal of the outer tube 180). The recesses 172 are shown in pairs, spaced apart axially, so that when the inner shaft 176 is advanced, projections 178 of outer tube 180 will engage one of the sets of recesses 172, thereby retaining the inner shaft 176 in position. Such retention/locking can also provide a tactile feel to the user. FIG. 8D shows the inner shaft 176 advanced to the first retention position. Upon application of sufficient axial force to inner shaft 176, the first (distal) pair of recesses moves past the projections 178 until the second set of recesses 172 are engaged by projections 178. This again retains the inner shaft 176 in position, but with the petals 110 partially exposed. For full expansion of the petals 110, the inner shaft 176 is further advanced until the third (proximal) set of recesses 172 engage projections 178, thereby retaining the inner shaft 176 and thereby the petals 110 in the fully expanded position, e.g., corresponding to the petal position of FIG. 3.

It should be appreciated that although three sets of recesses are provided, alternatively fewer or greater number of sets of recesses can be provided to provide a different number of stops for the inner shaft 176. Additionally, each set of recesses 172 can alternatively have only one recess or more than two recesses. The structure can also be configured so that the inner shaft has only one set of recesses and multiple axially spaced sets of projections are positioned on the internal surface of the outer tube 180. It should also be appreciated that the structure can be reversed so the recesses are on the inner surface of the outer tube 180 and the bumps or projections are on the outer surface of the inner shaft 176.

In another alternate embodiment, the inner shaft is frictionally engaged within the outer shaft and remains in position until a user applies a sufficient axial force to overcome the frictional force to advance the inner shaft within the outer shaft to deploy the petals. Once the axial force applied by the user ceases, the inner shaft remains fixed within the outer shaft due to the frictional engagement. This enables retention of the inner shaft ant any point along its length.

Figure 8G:
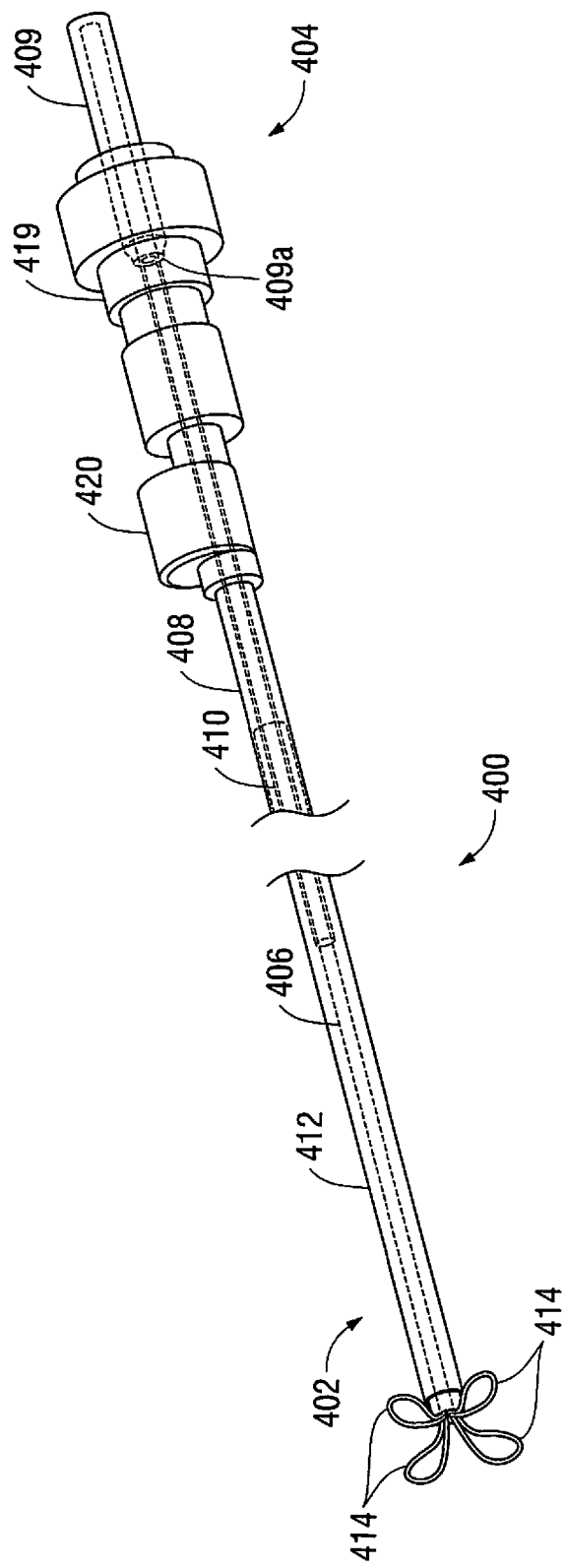
FIG. 8G is a perspective of the retractor of FIG. 8E shown in the extended position to expand the petals.

Another alternate embodiment of the tissue retractor is illustrated in FIGS. 8E-8G, and designated generally by reference numeral 400. Tissue retractor 400 has a distal portion 402 and a proximal portion 404. The tissue retractor 400 includes a central wire 406, a hypotube 408 coaxially positioned over a proximal region of the central wire 406, and an inner sheath 410 coaxially positioned over a region of the hypotube 408. The central wire 406 is attached to the hypotube 408 along its length by bonding or other methods. The inner sheath 410 is connected to the hypotube 408 such as by bonding or other techniques. Thus, the assembly which includes the central wire 406, hypotube 408 and inner sheath 410 (hereinafter referred to as the wire assembly) are movable (slidable) as a unit within the outer sheath 412. The outer sheath 412 preferably has a curvature (pre-bent) at a distal portion and functions as a flexible guide like the flexible guides (tool channels) described below. Note in FIG. 8G the outer sheath 412 is shown in the straight position which corresponds to the position when its distal tip is positioned within the catheter described below. When it is free from the confines of the catheter, the distal tip returns to its pre-bent position such as the bend shown in the flexible guides of FIG. 11 or of FIG. 45.

At the distal end of central wire 406 are a plurality of closed loops or petals 414. The petals 414 can be attached to the central wire 406 or alternatively the petals 414 are integral (monolithic) with the central wire 406 so they are formed from a single wire element. The petals 414 are identical in shape and function to petals 110 described above and therefore the discussion of the structure and function of petals 110 is fully applicable to petals 414. Note as in the embodiments mentioned above, although four petals (loops) 414 are shown, it should be appreciated that a fewer number or a greater number of petals 414 could be provided. As with petals 110, the petals 414 are movable from a collapsed insertion position within the outer tube (guide) or sheath 412 to an advanced position where they are exposed from the outer tube 412 and can move to the expanded position of FIG. 8G. The petals 414 can be made of shape memory material with a memorized configuration of FIG. 8G so when no longer constrained within the outer sheath 412 return to their memorized expanded position. The petals 414 in some embodiments can be covered with a material such as material 304 or 312*a*, 312*b* of FIGS. 3A, and 3B, or its variations, as described above. Note that in the embodiments described herein, the petals 414 are exposed by advancement of the assembly, e.g., hypotube 408, relative to the outer tube 412. However, it should be appreciated, that alternatively, the outer tube 412 could be retracted to expose the petals 414 or both the hypotube 408 could be moved distally and the outer tube 412 moved proximally. In each of these methods, it is the relative movement of the hypotube 408 and outer tube 412 that exposes the petals 414 for expansion.

The retractor 400 can include in some embodiments structure to provide limits on the proximal movement and distal movement of the wire assembly by movement restriction of the hypotube 408. More specifically, the tissue retractor 400 includes a luer fitting 420 attached to a luer adapter 419. The luer fitting 420 includes an internal tapered region 424, tapering inwardly toward the longitudinal axis, to provide a choke point so that upon sufficient retraction of the wire assembly, the inner sheath 410 which provides an end cap structure, is restricted from proximal movement by engagement of the proximal edge with the reduced internal diameter of the tapered region (choke point) 424. The hypotube 408 includes a handle 409 with a distal abutment surface 409a which in some embodiments is covered with a heat shrink material. Surface 409A engages (abuts) the internal flat face 413 of the adapter 419. Thus, this abutment limits distal movement of the wire assembly. A bushing can be provided in the adapter to fit against the hypotube handle 409. In this manner, these proximal and distal stops control the extent of movement of the wire assembly. Also, the distal stop prevents withdrawal of the wire assembly from the outer sheath 412 so it is non-removably positioned within the outer sheath 412.

Various diameters of the components are contemplated. In one embodiment by way of example, the hypotube 408 can have an outer diameter of about 0.079 inches, the hypotube handle 409 with heat shrink thereover can have an outer diameter of about 0.120 inches. the inner shaft 410 can have an outer diameter of about 0.130 inches, the outer sheath 412 can have an outer diameter of about 0.156 inches, and the choke point can have an internal diameter of about 0.115 inches. In one embodiment, the hypotube handle movement from the retracted to the extended position is about 1.00 inches although other distances are also contemplated. In another embodiment by way of example, the inner shaft 410 can have an outer diameter of about 0.091 inches, the outer sheath 412 can have an outer diameter of about 0.117 inches, and the choke point can have an internal diameter of about 0.081 inches. Other dimensions are also contemplated.

In a preferred embodiment, there is some frictional engagement between the inner sheath 410 and outer sheath 412 so that the central wire 406 and petals 414 can be maintained in position when a force is not applied to the hypotube handle 409. In such embodiment, when it is desired to move the central wire 406 axially, a force is applied to the hypotube handle 409 which overcomes the frictional retention force of the inner and outer sheaths 410, 412 to advance or retract the hypotube 408 and attached central wire 406.

In the embodiment of FIGS. 8E-8G, the wire assembly and outer sheath 412 are inserted as a unit together through the catheter described below. That is, the wire assembly is packaged along with (and coaxially inside) the outer sheath 412 and is slidable within the sheath. The proximal stop (i.e., tapered region 424) prevents the wire assembly from being pulled out of the outer sheath 412. It should also be appreciated, that it is also contemplated in an alternate embodiment the distal stop (and/or proximal stop) are not provided and the wire assembly is inserted by the user through a flexible guide such as the flexible guides described below.

Figure 11:
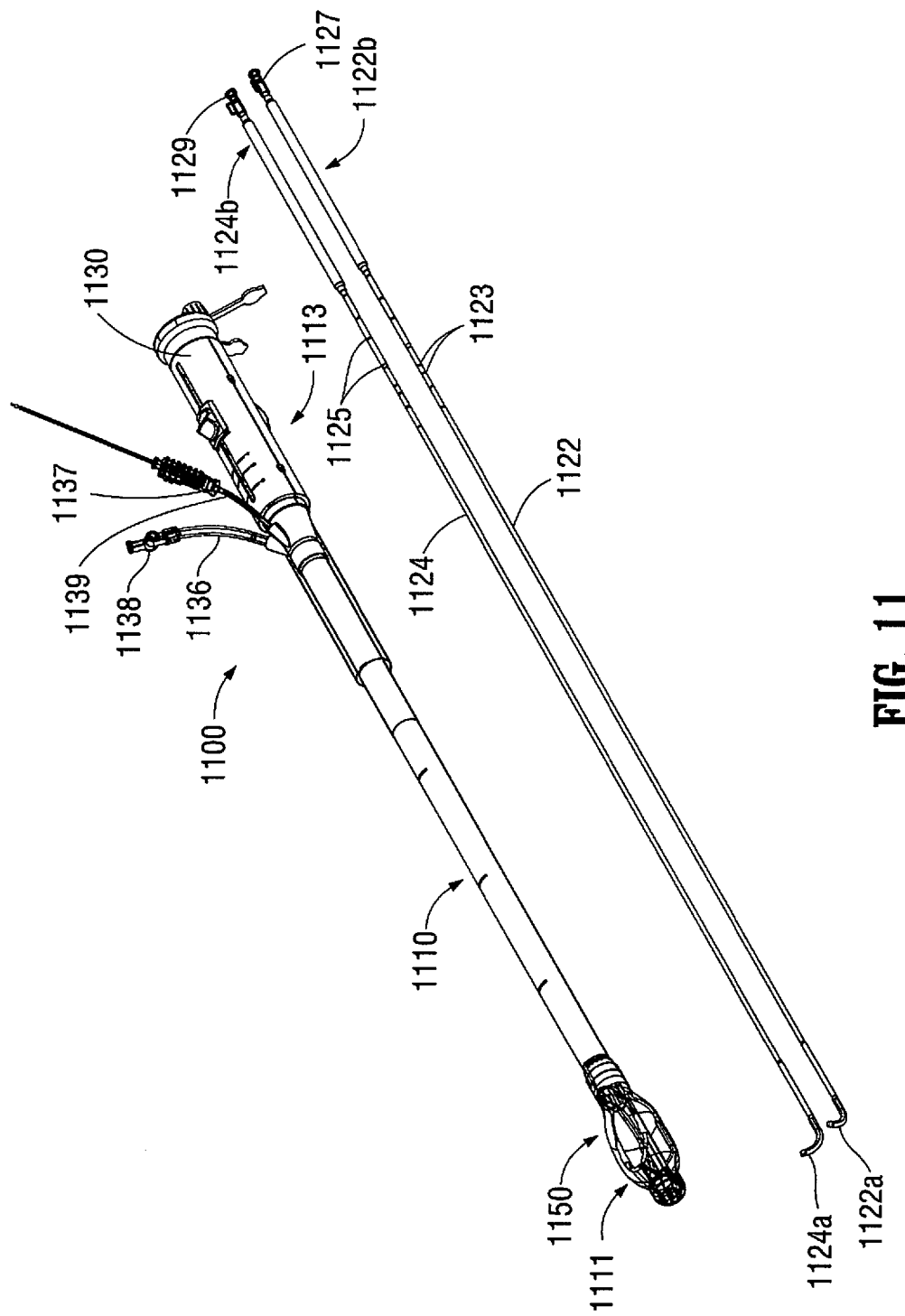
FIG. 11 is a perspective view of one embodiment of the system showing the catheter and two tool channels.

FIGS. 11-30 illustrate embodiments of the system, designated generally by reference numeral 1100. System 1100 includes a multi-lumen catheter or tubular member 1110 configured to receive one or more tool channels or flexible instrument guides. FIG. 11 shows two tool channels 1122 and 1124, it being understood that in some embodiments, only one tool channel can be utilized and in other embodiments more than two tool channels can be utilized, with the catheter provided with a sufficient number of lumens. The tool channels 1122, 1124 can be packaged as a kit with the catheter 1110 as shown in FIG. 11. Alternatively, the tool channels 1122, 1124 can be packaged separately. In other embodiments, the tool channels are packaged already inside the lumens of the catheter 1110. Each tool channel 1122, 1124 has a lumen (channel) to receive an endoscopic instrument (tool) therethrough.

Figure 12:
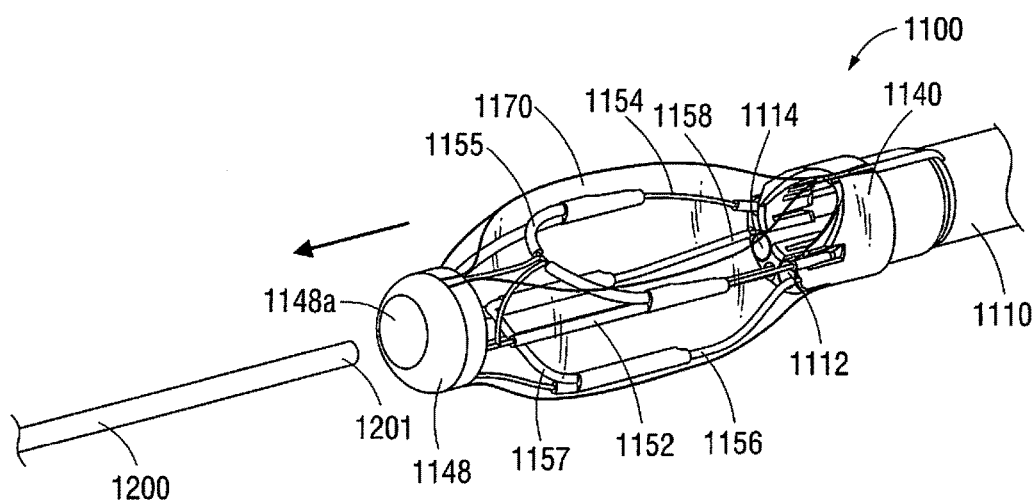
FIG. 12 is a perspective view of the catheter of FIG. 11 being inserted over the proximal end of the endoscope of FIG. 13 (prior to insertion of the endoscope into the colon), the retractor system shown in the collapsed position.

The tool channels (also referred to herein as flexible tubes or flexible guides) 1122 and 1124 are inserted through the proximal end of the catheter 1110 and advanced through respective lumens 1112, 1114 in the catheter 1110 (see FIG. 12). As shown in FIG. 16, which illustrates a proximal portion 1113 of catheter 1110, the catheter 1110 can include ports 1115, 1117, cooperating with the lumens 1112, 1114, respectively (see e.g. FIG. 13), which can include valves to maintain insufflation when the tool channels 1122, 1124 are inserted therethrough and translated axially therein. Tool channel (tube) 1122 preferably has a pre-bent tip 1122a, best shown in FIGS. 11 and 18, to provide a curved distal end. Tool channel (tube) 1124 also preferably has a pre-bent tip 1124a, providing a curved distal end. When the tool channels 1122, 1124 are inserted into the lumens 1112, 1114 of catheter 1110, the tips 1122a, 1124a are preferably substantially straightened to facilitate advancement through the lumens. When the tool channels 1122, 1124 are advanced sufficiently distally so the distal tips 1122a, 1124a are exposed from the confines of the walls of the catheter lumens 1112, 1114, the tips 1122a, 1124a, return to the pre-set curved position. This can be understood with reference to FIG. 18 which illustrates in phantom the straightened position of the tool channels 1122, 1124 for movement within the catheter 1110. As in the other embodiments disclosed herein, the tool channels 1122, 1124 can be composed of superelastic material, although other materials to provide the curved tip which returns from a substantially straight insertion shape to a curved shape when exposed can also be used, such as stainless steel. Also, as in the other embodiments disclosed herein, shape memory properties of material such as Nitinol can be used with a memorized curved tip shape. In alternative embodiments as described above, the tool channels 1122, 1124 can have a mechanism such as a pull wire which is actuated to bend its distal end. The tool channels 1122, 1124 in the embodiments of FIGS. 11-30 are unattached to the catheter 1110 so that the user can freely control their axial movement from a proximal end portion 1122b, 1124b, during use. However, it is also contemplated that in alternate embodiments the tool channels can be attached to the catheter.

The tool channels 1122, 1124 can optionally include markings 1123, 1125, respectively, at a region proximal to the catheter 1110 to provide a visual indicator to the user of the depth of insertion of the tool channels 1122, 1124 through the catheter lumens 1112, 1114. The tool channels 1122, 1124 can have a luer fitting 1127, 1129, respectively, (FIGS. 11 and 19A) with a valve, at the proximal end which can close off backflow of insufflation gas from the body. This maintains insufflation when the endoscopic tool is inserted through the tool channels 1122, 1124 as described below. The tool channels in an alternate embodiment shown in FIG. 19B have a hemostatic valve 1121A, 1121B connected at a proximal end of tool channels 1122', 1124', respectively, to maintain insufflation during tool insertion. As shown, valves 1121A, 1121B are proximal of luer fittings 1127', 1129'. The tool channels 1124', 1126' are identical to tool channels 1124, 1126 in all other respects.

In one embodiment, the tool channels 1122, 1124 can be composed of a flexible soft material, such as Pebax. A superelastic nitinol backbone can in some embodiments be embedded in the wall of the Pebax material, e.g., within the curved portion. Other materials are also contemplated.

Figure 45:
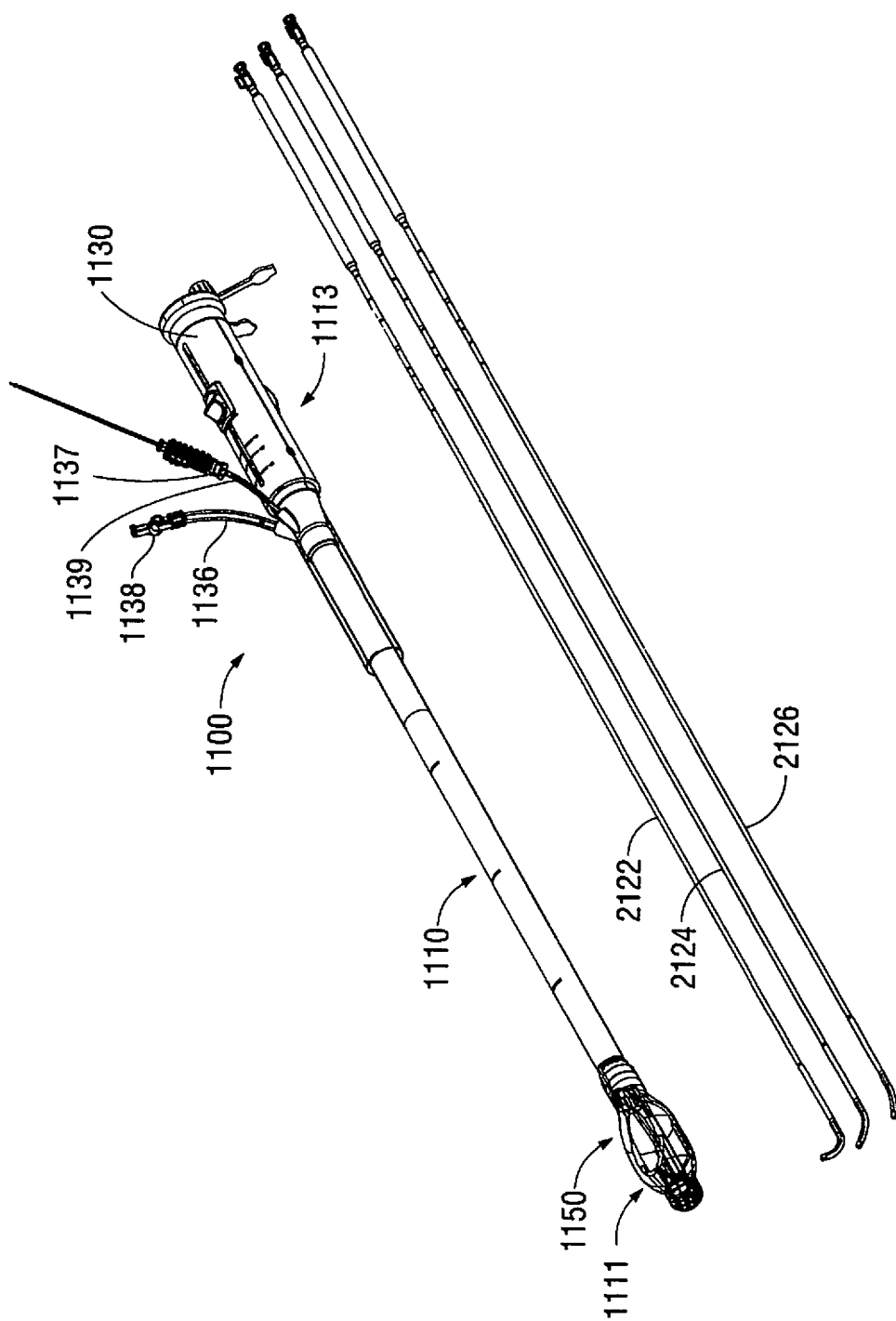
FIG. 45 is a perspective view showing one embodiment of a kit of the present invention having a set of flexible guides of different pre-bent angles.

Although the tool channels 1122, 1124 are shown with approximately 90 degree angles at the tip, other angles with respect to the longitudinal axis are also contemplated. FIG. 45 illustrates three tool channels 2122, 2124 and 2126 having different angles. More specifically, tool channel 2122 has a pre-bent tip curving to about a 90 degree angle, tool channel 2124 has a pre-bent tip curving to about a 60 degree angle and tool channel 2126 has a pre-bent tip curving to about a 45 degree angle. It should be appreciated that other angles are also contemplated. By providing various pre-set curves of different angles, the user can select the appropriate tool channel for directing the surgical instrument. For example, in a narrow lumen, the 60 degree angle may be more desirable that the 90 degree angle because it might be difficult to deliver the tool channel at the 90 degree angle. In some embodiments, the catheter is packaged as a kit with tool channels of varying angles such as the catheter 1100 and three varying angled tool channels 2122, 2124 and 2126 of FIG. 45. In other embodiments, one or more tool channels are packaged separately from the catheter.

Catheter 1110 also preferably has a lumen 1116 (see e.g., FIG. 16) configured and dimensioned to receive an endoscope 1200. In some embodiments, the lumen 1116 is dimensioned to receive a conventional endoscope, e.g., a conventional colonoscope, and the catheter 1110 is backloaded over the endoscope. This is described in more detail below in conjunction with the method of use. In alternate embodiments, the lumen 1116 can receive an articulating endoscope. Moreover, in alternate embodiments, the endoscope can be inserted into the catheter and inserted into the body lumen.

With reference to FIGS. 11 and 16, catheter 1110 includes a handle housing 1130 at the proximal portion 1113 which contains two actuators: actuator 1132 for controlling movement of the retractor system 1150 and actuator 1134 for controlling movement of the rigidifying (stabilizing) structure. These are discussed in more detail below.

Figure 13:
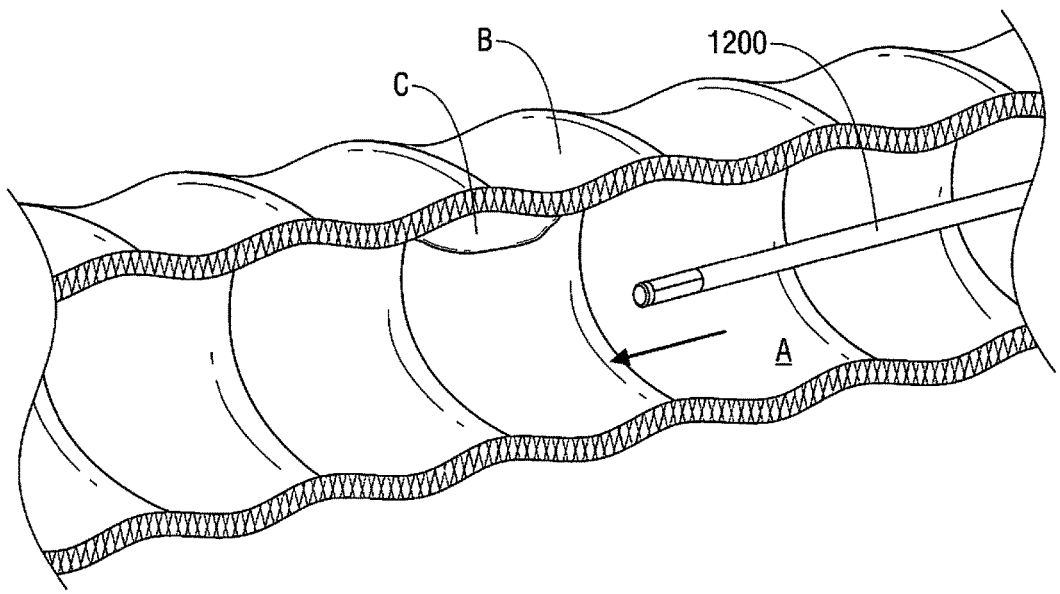
FIG. 13 illustrates insertion of the endoscope through the colon.

Turning now to the retractor system 1150, which forms a working space expanding system, and in certain clinical applications, a body lumen reshaping or reconfiguring system, and with initial reference to FIG. 13, the retractor system 1150 is positioned at the distal portion 1111 of the catheter 1110 (distal of proximal hub 1140) and includes flexible retractor elements 1152 and 1154. Retractor system also includes retractor elements 1156 and 1158. Retractor elements 1152, 1154 form the expandable elements which create the working chamber (space) within the body lumen and form an asymmetric cage. Retractor elements 1156, 1158 form the base of the retractor system, thus helping to define the retractor cage along with elements 1152, 1154. In some embodiments, retractor elements 1156, 1158 do not undergo any change when the retractor system 1150 moves from the collapsed insertion position to the expanded position; in other embodiments, retractor elements 1156, 1158 undergo a slight change in position, i.e., slight expansion or bowing, when the retractor system 1150 is expanded. Retractor elements 1152, 1154, are expandable to form an asymmetric working chamber to improve visibility and working space as described in detail above with respect to the other systems forming asymmetrical working spaces.

Figure 15:
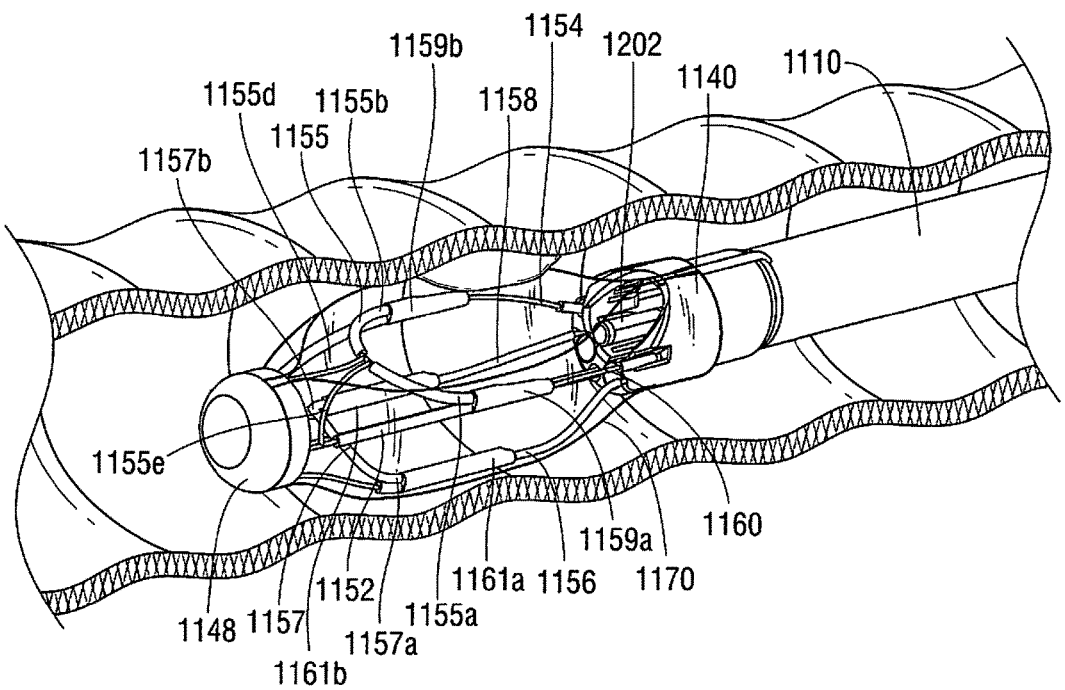
FIG. 15 is a perspective view showing the catheter fully advanced over the endoscope to the desired position adjacent the target tissue, the retractor system shown in the collapsed (non-expandable) position.
Figure 16:
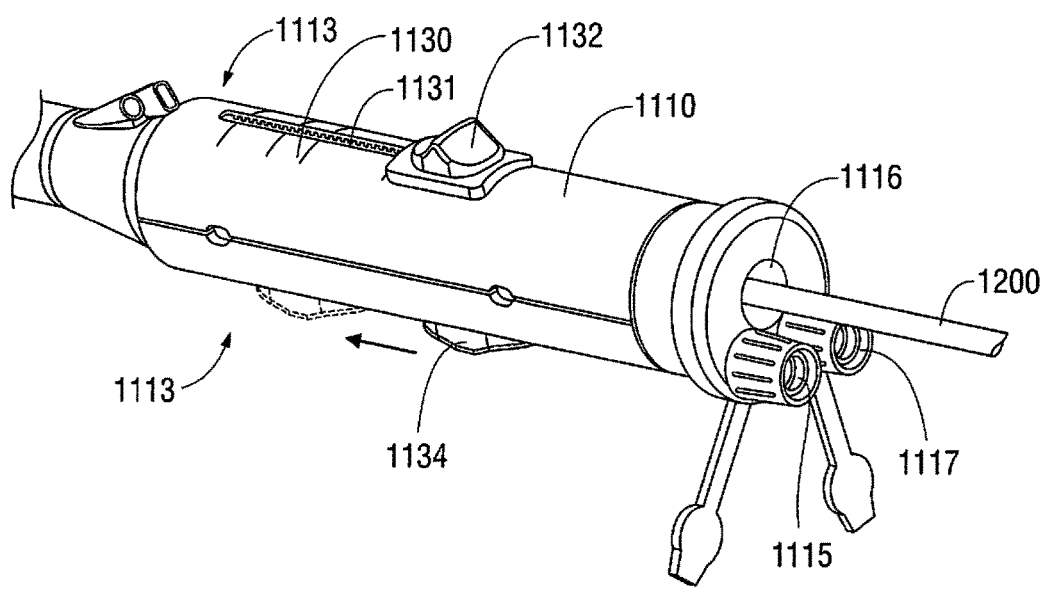
FIG. 16 is a perspective view of the proximal end of the catheter of FIG. 11.
Figure 21A:
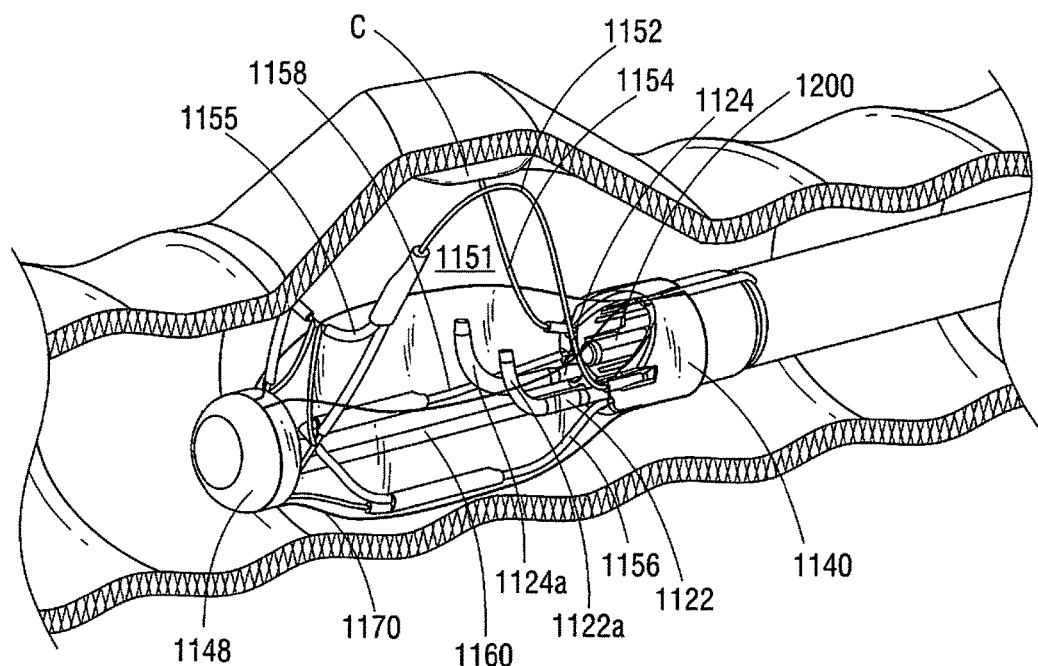
FIG. 21A is a view similar to FIG. 15 showing the retractor system in the expanded position and further illustrating the tool channels being advanced into the working space (chamber) created by the expansion of the retractor system.

As shown by comparing FIGS. 15 and 21A, retractor elements 1152 and 1154 move from a collapsed insertion position wherein they preferably do not extend beyond, or significantly beyond, the transverse dimension of the catheter 1110 to an expanded position wherein they bow laterally outwardly and have a transverse dimension extending beyond the transverse dimension of the catheter 1110. Also by comparing FIGS. 15 and 21A, it can be seen that lower (as viewed in the orientation of these figures) elements 1156, 1158 in the collapsed position do not extend beyond, or significantly beyond, the transverse dimension of the catheter 1110 and when the retractor is expanded, remain substantially in the same position so they still do not extend beyond, or significantly beyond, the transverse dimension of the catheter 1110. In some embodiments, the elements 1156, 1158 do not extend at all beyond the transverse dimension of the catheter 1110. As in the embodiments described above, the retractor system 1150, i.e., the retractor elements 1152, 1154, expand to only one side of a plane passing through a longitudinal axis of the catheter 1110, thereby creating the asymmetric working space 1151 (and asymmetric cage), with its attendant advantages described herein.

Retractor elements 1152, 1154 have a bridge member 1155 to add stability to the retractor and maintain a desired orientation of the retractor elements during the expansion. The bridge member 1155 is attached to the two retractor elements 1152, 1154, preferably at an intermediate portion, to create a transverse structure for the elements 1152, 1154, limiting side-to side movement. The bridge member 1155 can be a separate component attached to the retractor elements by tubular elements 1159a, 1159b, which are fitted over and attached to retractor elements 1152, 1154, respectively. Alternately, the bridge member 1155 can be integrally formed with one or both of the retractor elements 1152, 1154. The bridge member 1155 can be composed of a material similar to the elements 1152, 1154 or can be composed of a different material.

An additional bridge member 1157 (or alternatively multiple bridge members) extends between the two lower (as viewed in orientation of FIG. 15) retractor elements 1156, 1158. These elements 1156, 1158 can help open up the lower section of the retractor system 1150 and help form the cage for the working space, and the bridge member(s) 1157 can help to stabilize these elements 1156, 1158, e.g., limit side to side movement. The bridge members 1155, 1057 can be a separate component attached to the retractor elements by tubular elements, e.g., 1161a, 1161b, 1159a, 1159b as shown, which are fitted over and attached to the respective retractor elements Alternatively, the bridge members 1155, 1157 can be integrally formed with one or both of the retractor elements. The bridge member 1157 can be composed of a material similar to the elements 1156, 1158 or can be composed of a different material. Additional bridge members (not shown) can be provided on the retractor elements 1052, 1054 to increase stability.

The catheter 1110 includes a proximal coupler (cap) 1140 through which the retractor elements extend. Handle housing 1130 includes a longitudinally extending slot 1131 (FIG. 16) along which retractor actuator 1132 axially slides. The retractor elements 1152, 1154 are coupled to the actuator 1132 via block 1146, shown in FIGS. 20A and 20B. That is, each retractor element 1152, 1152 has a proximal extension that extends through the respective lumen 1112, 1114 in the catheter 1150 and is connected at its proximal end to the block 1146. In this manner, when the actuator 1132 is moved along axial slot 1131 from its proximal position of FIG. 20A to its distal position of FIG. 20B, the block 1146 is moved distally, thereby forcing the retractor elements 1152, 1154 laterally outwardly since the elements 1152, 1154 are fixedly attached to the distal coupler 1148 at their distal ends. Elements 1156, 1158 in this embodiment, are fixedly attached to the distal coupler 1148 at their distal ends, and fixedly attached to the proximal coupler 1140 (or other portion of the catheter 1110) at their proximal ends such that movement of actuator 1132 does not effect movement of these elements 1156, 1158. It should be appreciated, however, that if it is desired to have the elements 1156, 1158 move, e.g., flex slightly outwardly when the retractor 1150 is expanded, these elements 1156, 1158 can be attached to the block 1146 so they would be moved when actuator 1132 is advanced, or alternatively attached to a separate actuator. In one embodiment, the elements 1152, 1154, 1156 and 1158 can be fixed within slots formed in the distal coupler 1148. Note the proximal and distal couplers 1140, 1148 can have openings dimensioned to receive an endoscope when the catheter 1110 is backloaded over the endoscope as described below. Housing 1130 can include a plurality of teeth (not shown) similar to the teeth of FIGS. 6A-6D for engagement by a tooth coupled to the actuator 1132, thereby forming a retaining or locking mechanism to retain the retractor elements in one of several select positions. A release mechanism for the retaining or locking mechanism can be provided.

Additionally, it should be appreciated that alternative ways to expand the retractor elements can be utilized, including for example providing relatively movable couplers 1140, 1148 to expand the retractor elements 1152, 1154 (and optionally 1156, 1158) in the same manner as the couplers described above, e.g., couplers 198, 199. The retractor elements can also alternatively be made of self-expanding material, such as shape memory material, which expand when exposed from the catheter or sheath.

Retractor elements 1152, 1154 can optionally have a small crimp forming a flattened position at a distal end adjacent where they are anchored to the distal coupler 1148. This reduces the bending stiffness at the point so it acts like a hinge to create a more predictable direction of expansion, e.g., to deflect upwardly and slightly outwardly. This also decreases the amount of force required to initiate the bending. Such flattened portion can also be used with the retractor elements of the other embodiments disclosed herein.

Figure 17A:
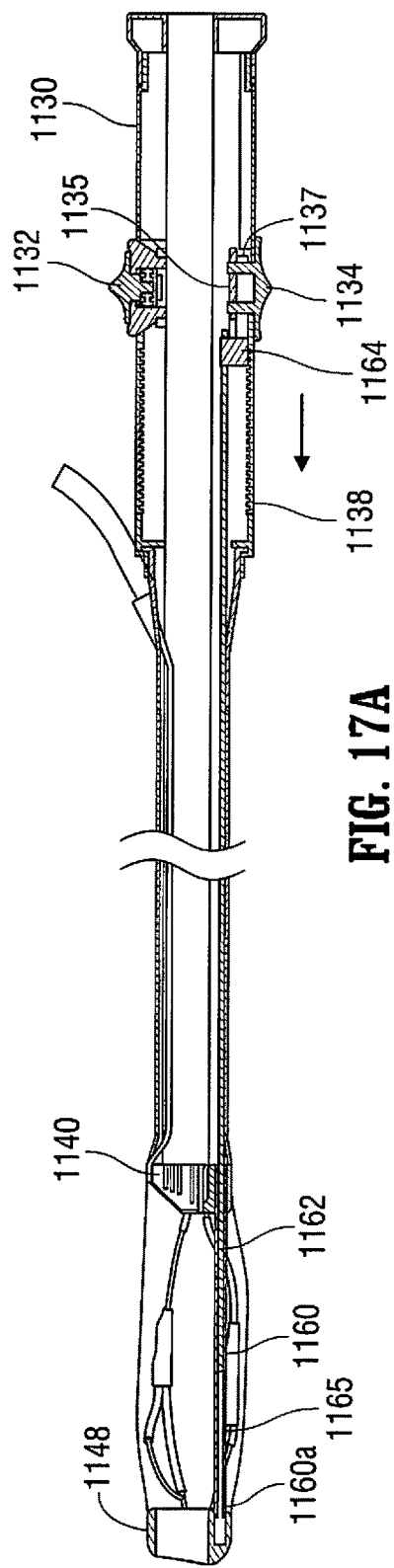
FIGS. 17A and 17B are side views in partial cross-section showing movement of the actuator from a proximal position to a distal position to advance the rigidifying structure to stiffen the retractor system.

The retractor system 1150 can be configured to reversibly stiffen an otherwise flexible arrangement of the retractor 1150. In this regard, retractor system 1150 can include a substantially-rigid beam to support the expanded retractor 1150 which helps to create a more stabilized chamber (or cage) as described herein. With reference to FIGS. 15 and 17A, a flexible tube or beam 1160 is provided in the collapsed configuration, whereas in FIG. 17B, the retractor system has a rigid beam that is formed from the flexible beam 1160. More specifically, in this embodiment, the flexible beam 1160 is in the form of a rod or tube 1165 having a lumen to slidably receive therein a stabilizing or rigidifying structure such as a rigid tube or rod (beam) 1162. The rigidifying (stabilizing) structure 1162 is independently actuated by the user by movement of actuator 1134. Actuator 1134 is slidably mounted within a longitudinally extending slot of housing 1130. In the initial position of FIG. 17A, rigidifying structure 1162 is retracted within a lumen of the catheter and either not engaged, or only partially engaged, with flexible tube (or rod) 1160. Rigidifying structure 1162 attached at its proximal end to sliding block 1164 which is operably connected to actuator 1134. To rigidify tube 1160, actuator 1134 is slid distally to the position of FIG. 17B, thereby advancing sliding block 1164 and the attached stabilizing structure 1162 distally. Such movement advances the rigidifying structure 1162 through the lumen 1165 of the flexible tube 1160 to the distal end 1160a to thereby stiffen the beam. The rigidifying structure 1162 can optionally be removed from the flexible beam 1060 to return the system back to the original more flexible state to aid collapsing of the retractor system 1050 by sliding the actuator 1134 in the reverse direction (proximally) within the axial slot, thereby withdrawing rigidifying structure 1162 from the advanced position within flexible tube 1160. In one embodiment, the rigidifying structure 1162 is in the form of a structure having a proximal and distal metal tubular structure joined by a flexible braid polyimide tube. However, it should be appreciated that other structures are also contemplated. Note the structures 1160, 1162 can be substantially circular in cross-section, although other cross-sectional shapes are also contemplated. As in the aforedescribed embodiments, the rigid beam limits deflection of the distal end 1111 of the catheter 1110 which could otherwise occur by pressure exerted on the distal end by the body lumen wall.

Figure 17B:
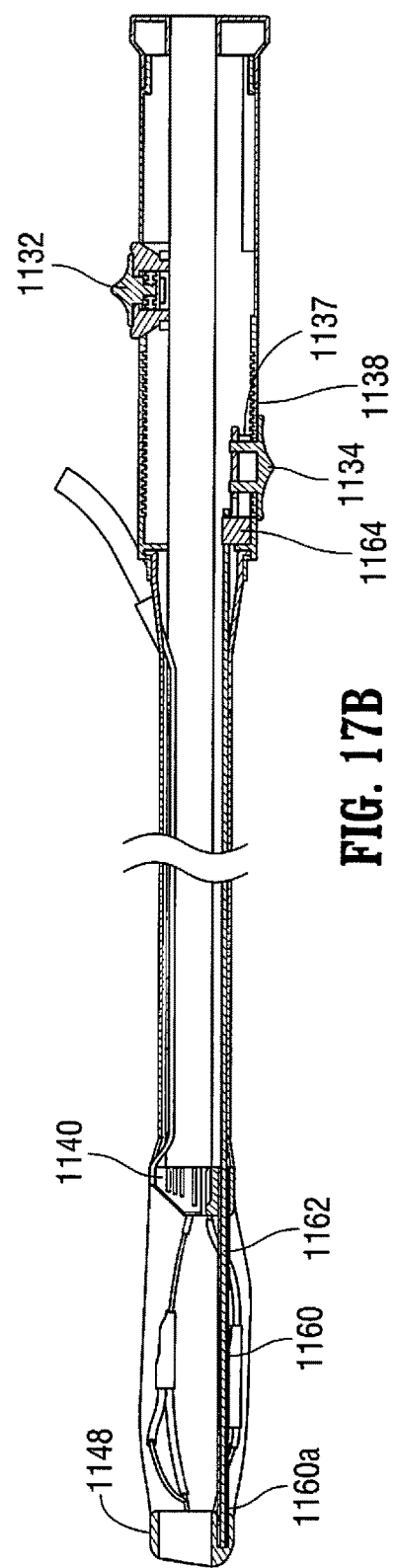

As shown in FIGS. 17A and 17B, the actuator can include a connector 1135 having a tooth or pawl 1137 to engage a tooth on the rack 1138 positioned within housing 1130 to retain the rigidifying structure 1164 in one of several selected positions.

Figure 17C:
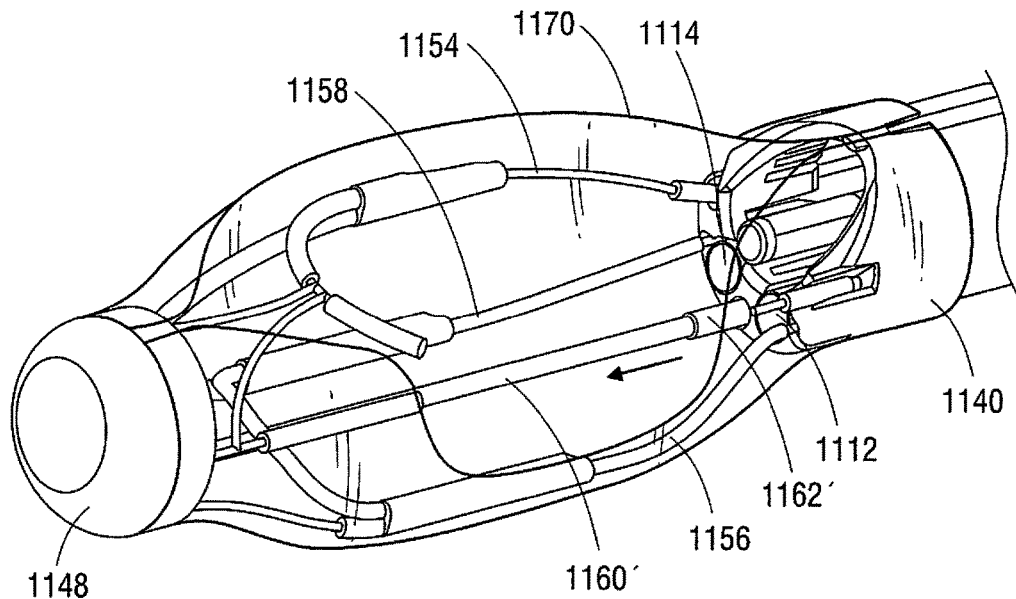
FIG. 17C is a perspective view similar to FIG. 15 showing an alternate embodiment of the rigidifying structure.
Figure 17D:
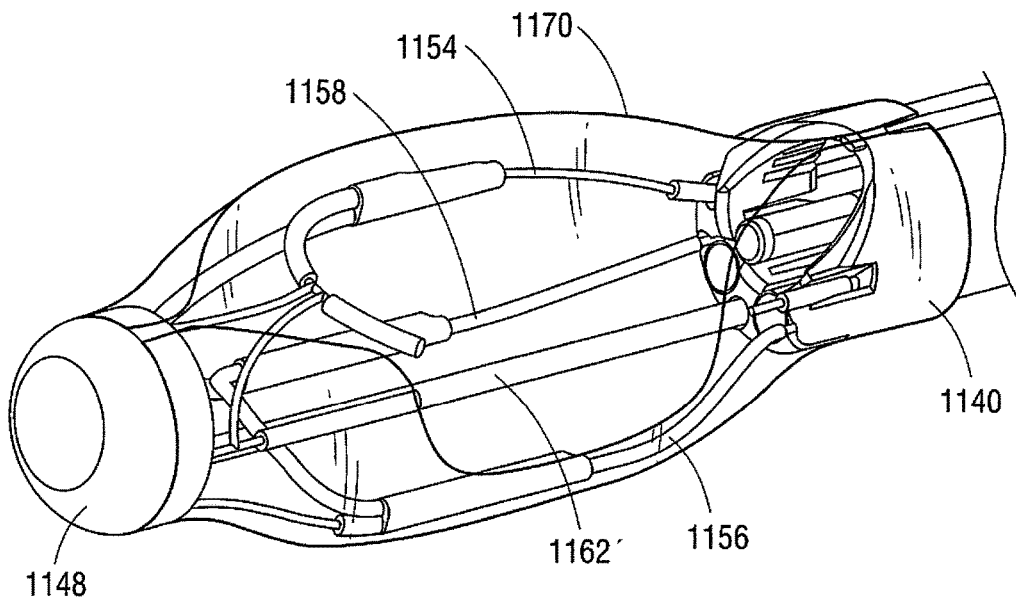
FIG. 17D is a perspective view similar to FIG. 17C showing the rigidifying structure of FIG. 17C advanced over the flexible element.
Figure 18:
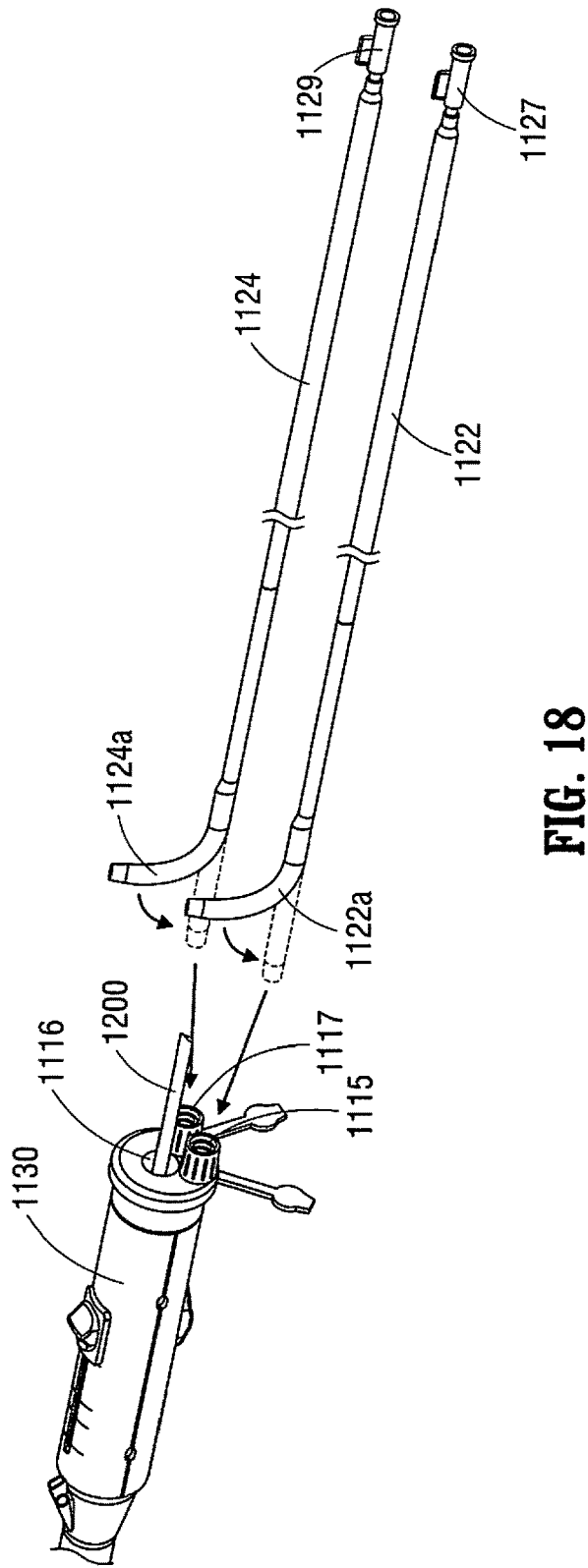
FIG. 18 is a perspective view showing the two tool channels (guides) adjacent the proximal end of the catheter of FIG. 11 for insertion therethrough.

In the alternate embodiment of FIGS. 17C and 17D, instead of advancing a rigidifying structure within the lumen of the flexible element, the rigidifying structure is advanced over the flexible element. More specifically, flexible beam 1160' is rigidified by movement of a rigidifying structure, e.g., tubular member 1162', over the flexible beam 1160'. That is, rigidifying member 1162' has a lumen configured and dimensioned to receive flexible beam 1160' as it is passed thereover in the direction of the arrow of FIG. 17C. Note that flexible element 1152 has been removed from FIGS. 17C and 17D for clarity. Actuator 1134, as well as alternative methods, can be utilized for such movement.

A covering or cover 1170 is preferably provided at a distal end of the catheter 1110. Covering 1170 in the illustrated embodiment is mounted around the perimeter of the proximal coupler 1140 and the distal coupler 1148. In some embodiments, the cover 1170 is pleated and sealed around the couplers (caps) 1140, 1148 by a heat shrink wrap. The cover 1170 is positioned around the elements 1152, 1154, 1156, 1158 in the collapsed insertion position, with an opening in the cover 1170 facing toward the target tissue, e.g., the lesion to be removed. That is, in the orientation of FIG. 15, the opening in cover 1170 faces upwardly. The cover 1170 can be configured to have an opening in the collapsed position, or, alternatively, it can provided with a slit which can be opened due to stretching when the retractor elements 1152, 1154 are moved to the expanded position. When the retractor elements 1152, 1154 are expanded, they move past the cover 1170 toward the target tissue. Alternatively, the edges of the cover 1170 can be attached to the retractor elements 1152, 1154 and thereby move with the retractor elements. When the target tissue is removed by the endoscopic instruments described herein, the removed tissue is placed within the cover 1170, and the cover 1170 is closed, e.g., by a string or suture 1172 shown in FIG. 29 to encapsulate the tissue and prevent leakage and seeding during removal from the body lumen. The suture 1172 can be embedded in a wall of the cover 1170 or in pockets or channels formed in the cover 1170, where it is permanently fixed at a distal anchor point, and pulled proximally to tension the suture 1172 and close the cover 1170.

Figure 10:
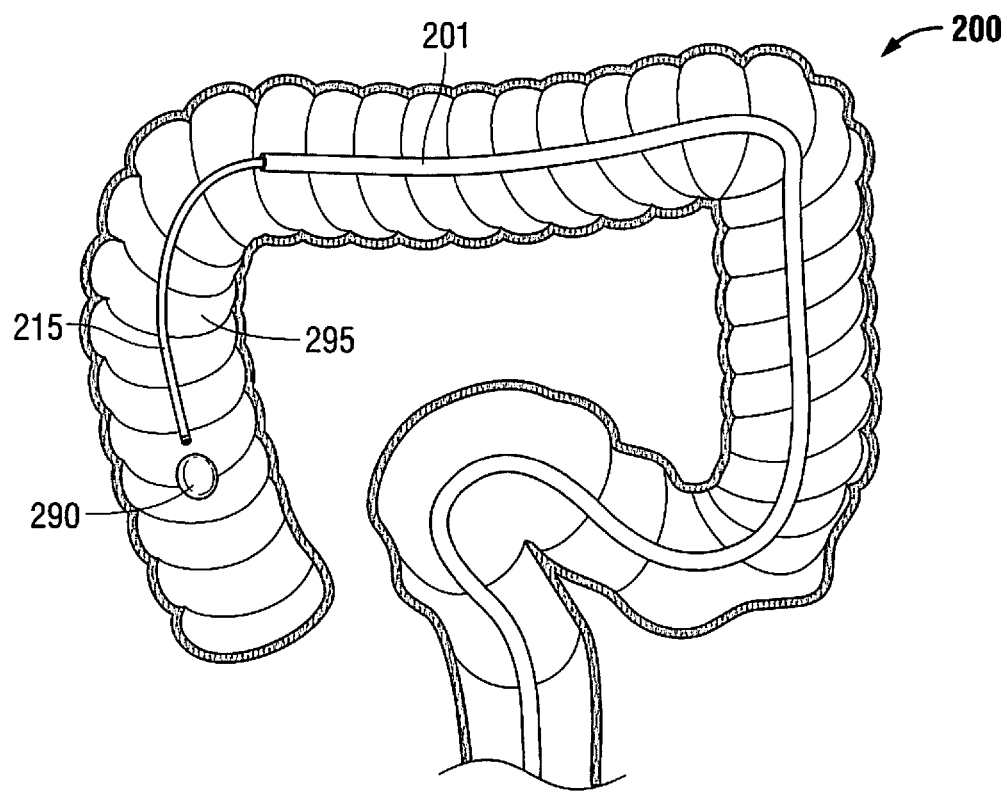

As with the cover (sheath) 1000 of FIG. 10, the cover 1170 by covering the retractor elements 1152, 1154, 1156, 1158 can provide a smooth and atraumatic surface for the delivery of the retractor system to the target site. The cover 1170, like cover 1000, also helps to prevent tissue, e.g. the luminal walls, from entering through the spaces between the beam 1160 and elements 1156, 1158 during the surgical procedure.

In a preferred embodiment, the two ends of suture 1172 extend out of tubing 1139. Their proximal ends can be covered by a length of tubing to facilitate grasping by the user.

Figure 9:
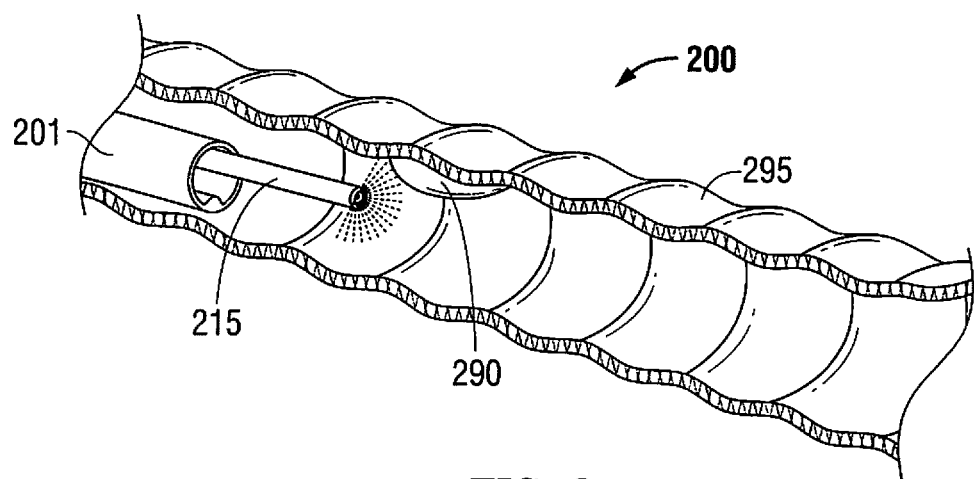
FIGS. 9 and 10 illustrate how a system as taught herein can be positioned for treating a lesion in the ascending colon, according to some alternate embodiments.

The use of the system of FIG. 11 will now be described with reference to removing a lesion, such as a polyp, from a colon wall, it being understood, however, that the system 1100 can used for other procedures within the colon or the gastrointestinal tract, as well as used for other procedures in other body lumens or body spaces of a patient. Its insertion into the ascending colon is illustrated in FIGS. 9 and 10 by way of example. FIG. 8 illustrates how an endoscope 215 can be used to locate the lesion, a target tissue 290 in a portion of the ascending colon 295. FIG. 10 illustrates how the multi-lumen-catheter retractor system 201 can be guided to the target tissue 290 using the endoscope 215 as a guide for the positioning 200 of the system in the treatment of the target tissue 290. As can be appreciated, the multi-lumen catheter is advanced over the endoscope 215 as shown in FIG. 10.

Figure 14:
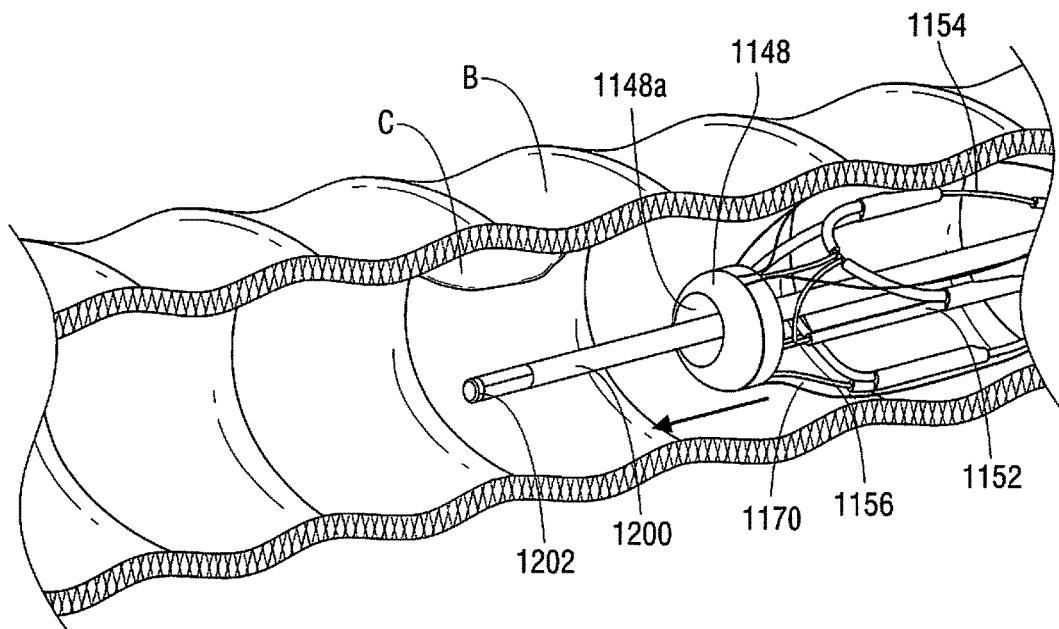
FIG. 14 is a perspective view showing the catheter of FIG. 11 being further advanced over the endoscope of FIG. 13, the retractor system shown in the collapsed position.

Turning first to FIGS. 12 and 13, a distal viewing endoscope 1200, in which the system 1100 has been advanced over the proximal end 1201 as shown in FIG. 12, or alternatively the system 1100 backloaded over the distal end of the endoscope 1200, is inserted through lumen A in the colon B in a procedure to remove the target polyp C from the wall of the colon B. The endoscope 1200 in this embodiment is a distal viewing scope with a wide distal viewing area of about 150-170 degree range so the polyp C and surrounding area can be visualized. After placement of the scope 1200 adjacent the target issue, i.e., slightly proximal of the target polyp C, the system 1100 is further advanced over the endoscope 1200. Distal coupler (cap) 1148 has an opening 1148a, and proximal coupler (cap) 1140 has an opening communicating with the lumen 1116 (FIG. 16) of the catheter 1110 to enable such backloading of the endoscope 1200 and advancement of the system 1100 thereover. The catheter 1110 is advanced over the endoscope 1200 as shown in FIG. 14 until it reaches the target site as shown in FIG. 15, with the retractor system 1050 aligned with the polyp C. As can be appreciated, in this insertion position of the catheter 1110, the retractor system 1150 is in the non-expanded (or collapsed) position, with retractor elements 1152, 1154, preferably not exceeding, or only slightly exceeding, the transverse dimension of the catheter 1110. In this position, the retractor elements, or at least retractor elements 1156, 1158, are covered by the covering 1170. As shown, in this position, the distal end 1202 of the endoscope 1200 is preferably positioned at the end of proximal coupler 1140 and does not extend into the working space 1151 to thereby leave more room for maneuvering of the endoscopic instruments within the working space. Other positions, however, are also contemplated, e.g., in some versions the endoscope can extend into the working space 1151. Note also in this insertion position, actuators 1134 and 1132 are in their retracted position as shown in FIG. 16.

Next, to rigidify the retractor system 1150, the actuator 1134 is moved distally from the position of FIG. 17A to the position of FIG. 17B (see also the arrow in FIG. 16) to advance rigidifying structure 1162 from the retracted position to an advanced position within lumen 1165 of flexible tube 1160. This stiffens/stabilizes the retractor system 1150 as discussed above. Note, as discussed above, the retractor system 1150 can alternatively be stiffened/stabilized by advancement of a rigidifying structure over the flexible element as shown in FIGS. 17C and 17D.

The retractor system 1150 is now expanded. Actuator 1132 is advanced distally from the position of FIG. 20A to the position of FIG. 20B (see also FIG. 19). This advances block 1146 (which is operably coupled to retractor elements 1152 and 1154 as discussed above) which forces retractor elements 1152, 1154 laterally outwardly to the position of FIG. 20B, thereby creating the asymmetric working space (chamber) as described in detail above.

Figure 21B:
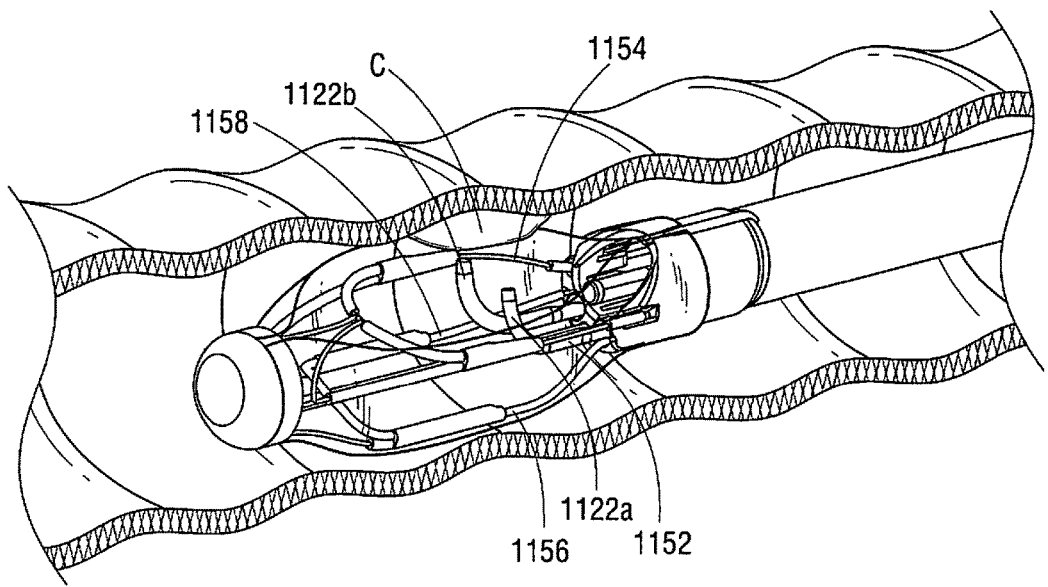
FIG. 21B is a view similar to FIG. 21A illustrating an alternate embodiment wherein the tool channels are advanced from the catheter prior to expansion of the retractor system.

Next, tool channels 1122, 1124 are inserted through the ports 1115, 1117 in the proximal region of the catheter 1110 (see FIG. 19A) and advanced by the user through the catheter lumens 1112, 1114 so they extend out the distal openings of the lumens 1112, 1114 and into the chamber 1151 as shown in FIG. 21A. Note as they emerge from the lumens 1112, 114, and out of the confines of the lumen walls of the catheter 1110, their distal tips 1122a, 1124a return to their curved (bent) position, curving upwardly (as viewed in the orientation of FIG. 21A) toward the polyp C. Note in FIG. 21A, the retractor elements are first expanded, followed by insertion of the tool channels 1122, 1124 out of the catheter lumens 1112, 1114 and into the working space 1151. However, it is also contemplated that in an alternative embodiment, the tool channels 1122, 1124 can be inserted through the catheter lumens 1112, 1114 and into the working space 1151 prior to expansion of the retractor elements 1152, 1154. This alternate method is shown in FIG. 21B, with the tool channel tips 1122a, 1122b exposed, but the retractor system 1150 still in the non-expanded position. Note the tool channels 1122, 1124 can be independently rotated and/or moved axially to adjust their position with respect to the polyp C. As can be appreciated, the terms upwardly and downwardly as used herein refer to the orientation of the system in the referenced Figures. If the position of the system changes, the orientation and terms would also change.

Figure 22:
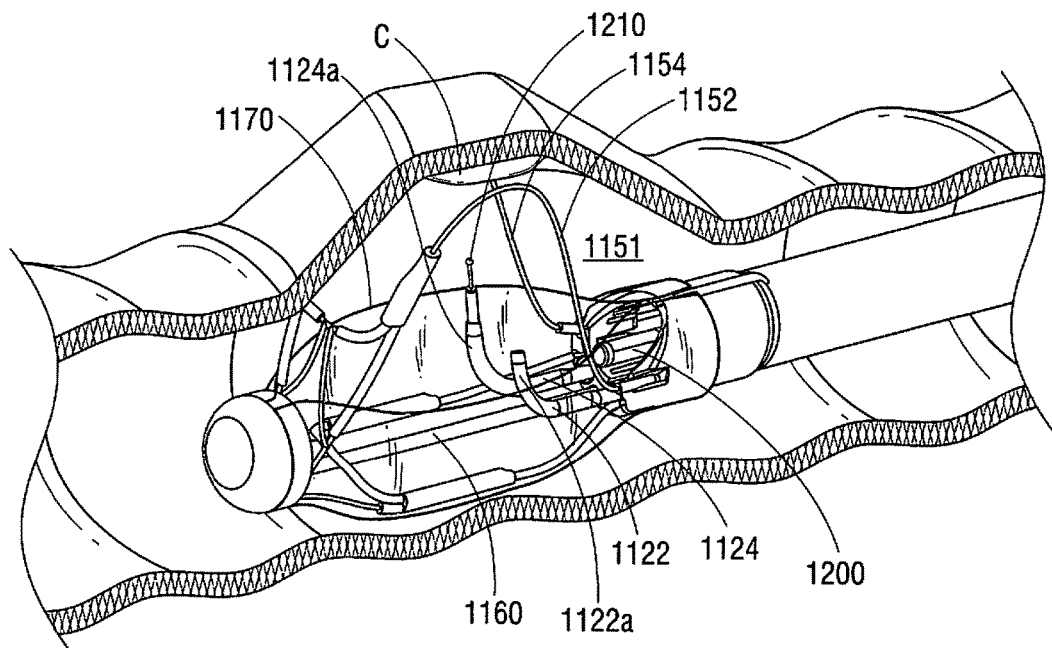
FIG. 22 is a view similar to FIG. 21A showing a first endoscopic instrument (tool) advanced from a first tool channel.
Figure 23:
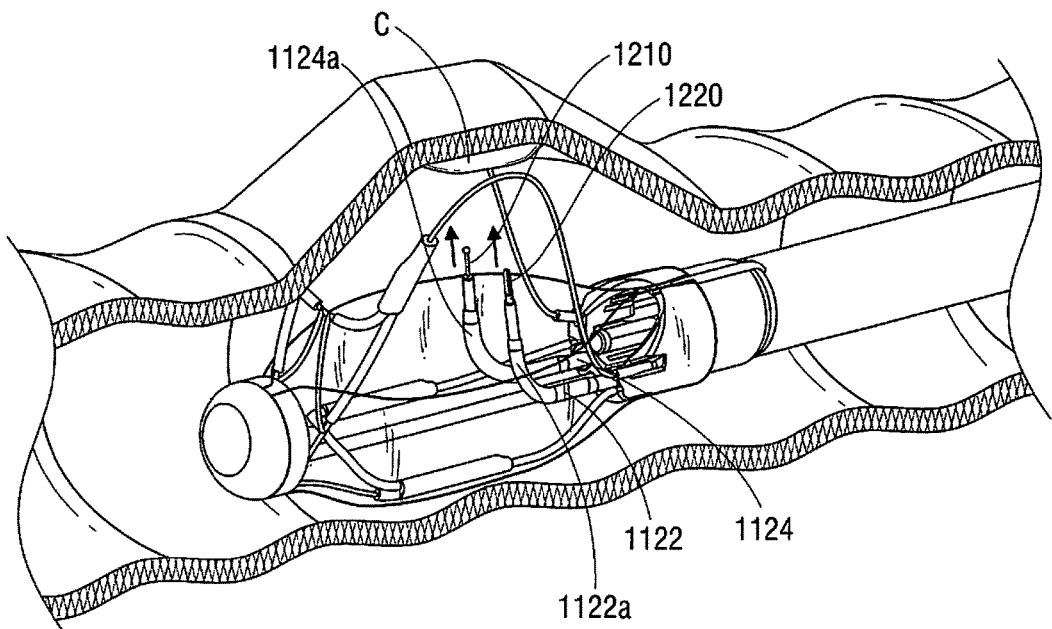
FIG. 23 is a view similar to FIG. 22 showing a second endoscopic instrument (tool) advanced from a second tool channel.
Figure 24:
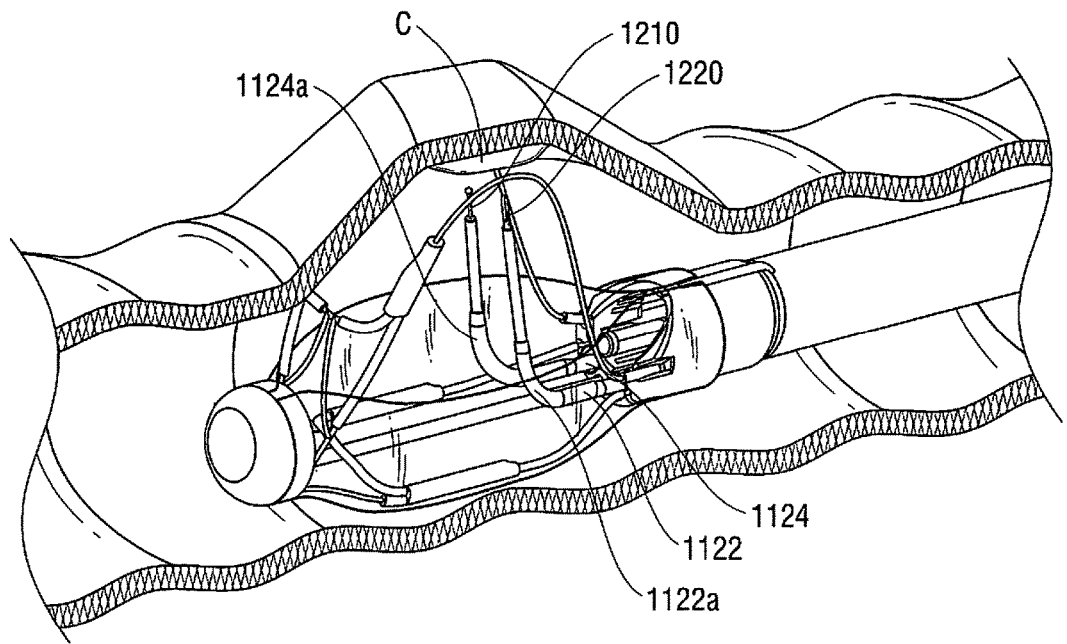
FIG. 24 is a view similar to FIG. 23 showing both endoscopic instruments further advanced from the tool channels.
Figure 25:
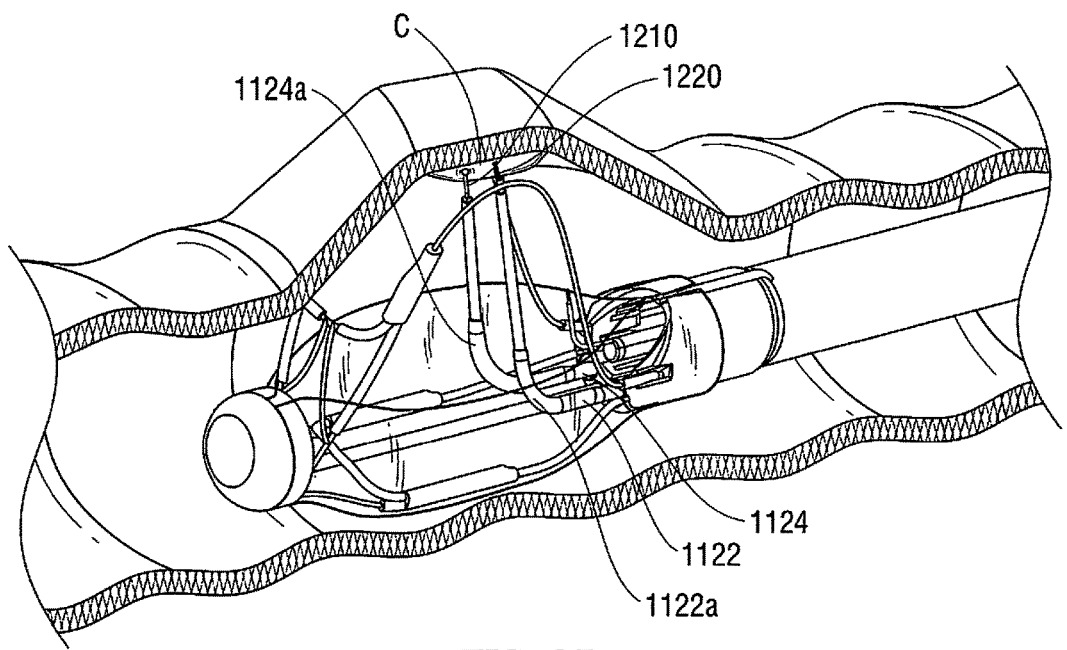
FIG. 25 is a view similar to FIG. 24 showing the endoscopic instruments further advanced from the tool channels to dissect the lesion on the colon wall.

After insertion of the tool channels 1122, 1124, endoscopic instrument (tool) 1210 is inserted through the luer fitting 1129 (FIG. 19A) of the tool channel 1124 and advanced through the lumen (channel) of the tool channel. As shown in FIG. 22, a first endoscopic instrument 1210 extends from tool channel 1124 and follows the curve of the tool channel 1124. A second endoscopic instrument (tool) 1220 is inserted through the luer fitting 1127 of tool channel 1122 and advanced through the lumen of the tool channel 1122. As shown in FIG. 23, the second endoscopic instrument follows the curve of the tool channel 1122. As noted above, the tool channels can include a valve, such as the hemostatic valves as shown in FIG. 19B, so insufflation is not lost during insertion and removal of the endoscopic instruments from the tool channels. The endoscopic instruments 1210, 1220 can be moved further axially as shown in FIGS. 24 and 25 to extend further from the tool channels 1122, 1124 to contact and treat, e.g., remove, the polyp C. This movement of the endoscopic instruments shown by comparing FIGS. 23-25 shows the advantage of the tool channels 1122, 1124. As can be seen, once the tool channels 1122, 1124 are in the desired position with respect to the polyp C, they can be considered as defining a fixed curve. This means that when the endoscopic instruments 1210, 1220 are axially advanced, they move closer to the target polyp C, without a change in curvature and without a change in their axial position with respect to the polyp C, thus providing an extra degree of freedom. The endoscopic instrument 1210, which in the illustrated embodiment is a grasper, applies tension on the polyp C while an electrosurgical dissector dissects/severs the polyp C from the colon wall B. Other endoscopic instruments for polyp removal can also be utilized. Additionally, in some embodiments, a single tool channel can be utilized and another endoscopic instrument, e.g., a grasper or a dissector, can be inserted through a working channel (lumen) of the endoscope. Such instrumentation inserted through an endoscope can also be utilized with the embodiments having two or more tool channels.

Figure 43:
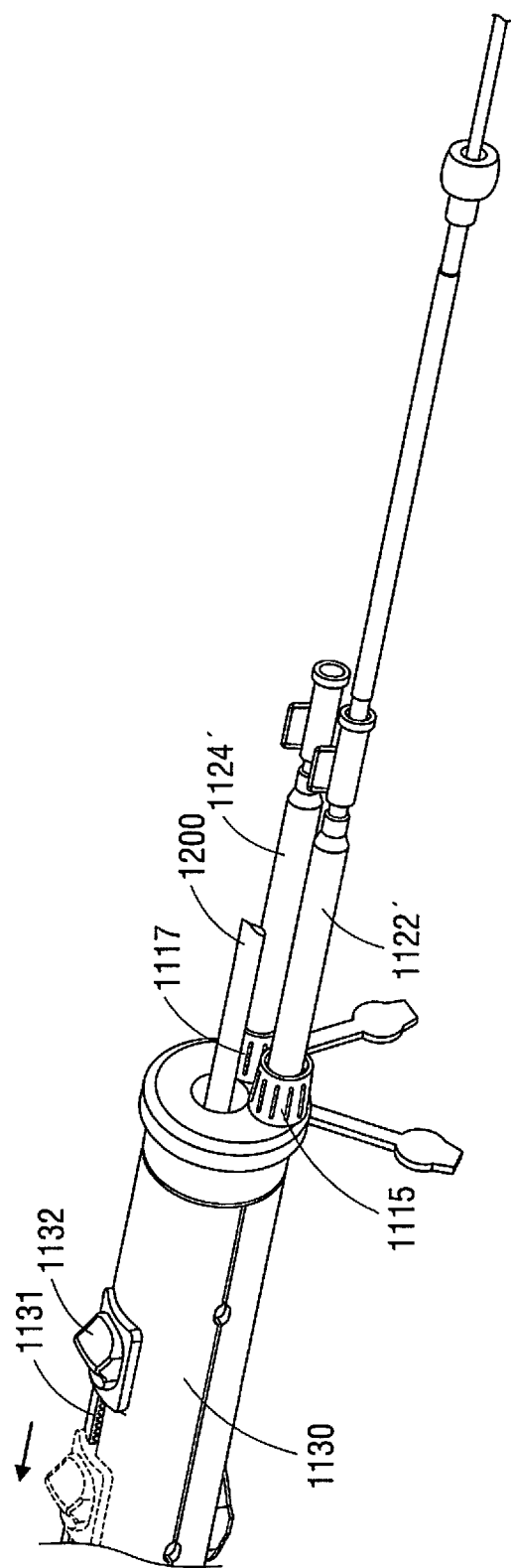
FIG. 43 is a perspective view of the proximal portion of the system illustrating the tissue retractor of FIG. 1 being inserted through one of the tool channels.
Figure 44A:
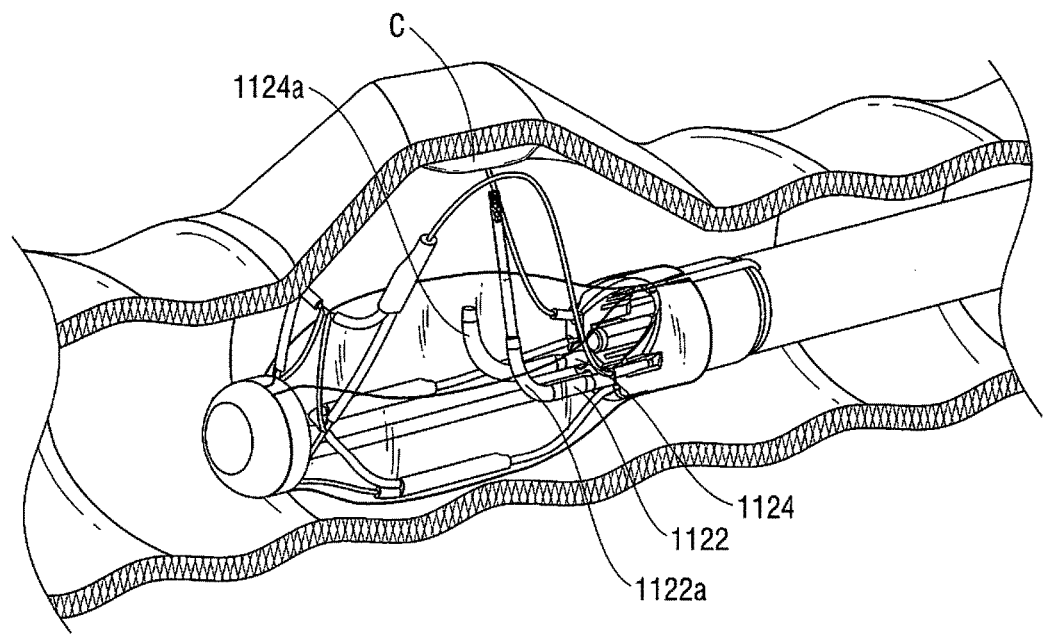
FIG. 44A is a perspective view illustrating the tissue retractor of FIG. 1 inserted through the tool channel so the distal portion extends into the working space, the tissue retractor petals shown in the collapsed position.
Figure 44B:
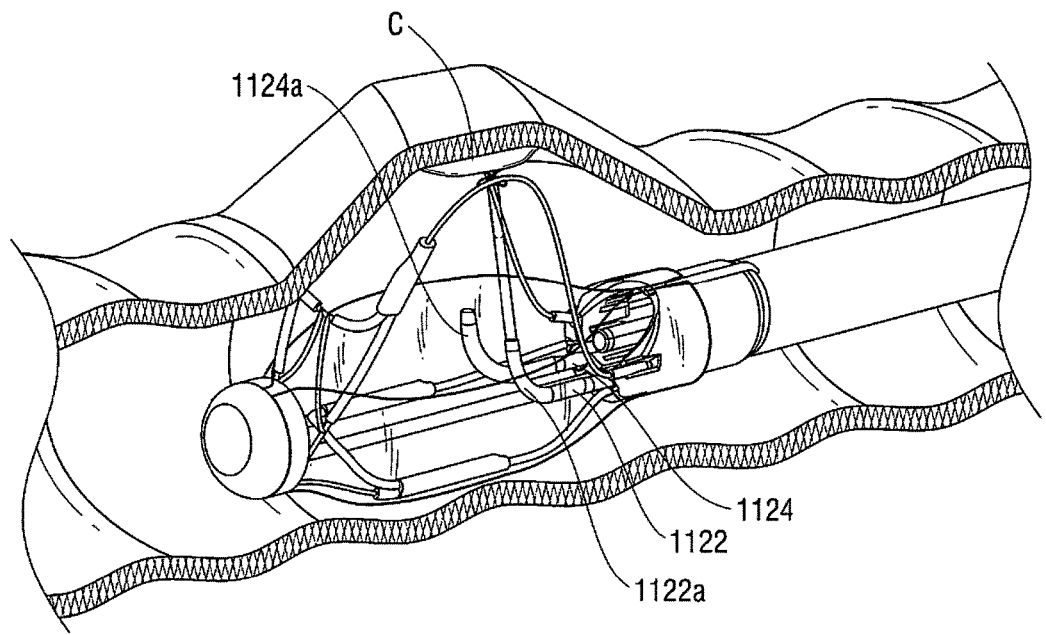
FIG. 44B is a perspective view similar to FIG. 44A showing expansion of the tissue retractor petals in the working space and engaging a polyp.
Figure 44C:
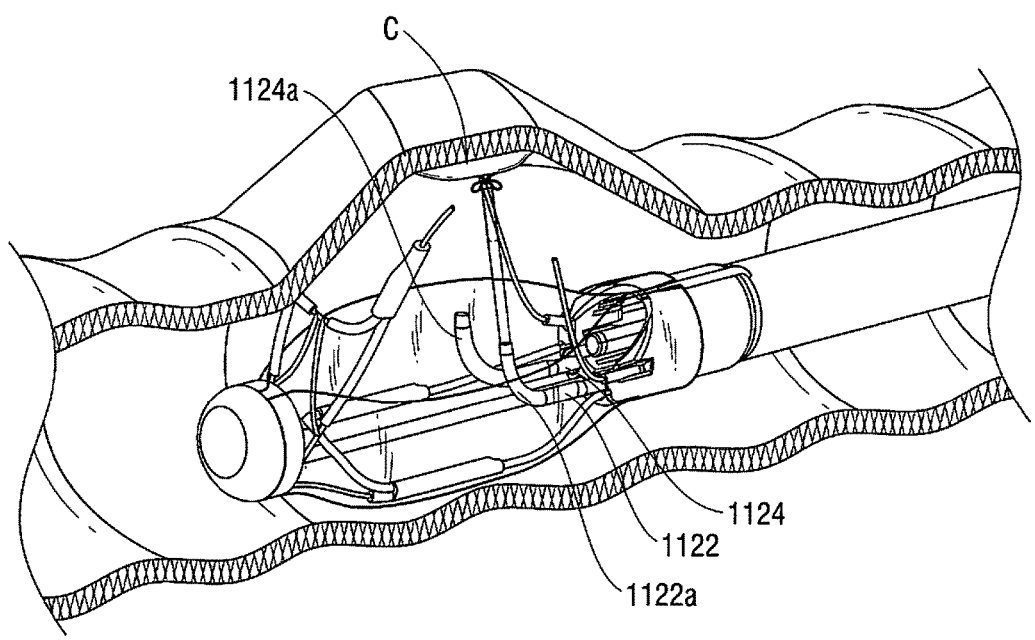
FIG. 44C is a view similar to FIG. 44B with portions of the flexible retractor elements removed for clarity.

FIGS. 43-44C illustrate insertion of the tissue retractor 100 of FIG. 1 through the catheter 1110. As shown in FIG. 43, retractor 100 is inserted through tool channel 1122 and advanced to exit from the distal opening into the expanded working space. As shown in FIG. 44A, the retractor 100 is flexible so it is advanced around the angled tool channel 1122. The inner shaft 106 of tissue retractor 100 is advanced to expose the petals 110 as shown in FIG. 44B and the retractor 100 is manipulated so the petals 110 gently but firmly push bulky tissue, such as a large polyp, away from the dissection plane (operating field) within the body lumen which would otherwise obscure the dissection plane during the procedure. Note FIG. 44C is similar to FIG. 44B except portions of the flexible retractor elements have been removed for clarity. The other tissue retractors disclosed herein can be inserted and manipulated in a similar manner. Alternatively, the tissue retractors disclosed herein can be inserted directly through he lumen of the catheter without the use of a tool channel.

Tissue retractor 100 is shown inserted through the tool channel (flexible guide/tube) 1122 disclosed herein. As described herein, the use of the tool channel increase the degrees of freedom of the tissue retractor in the same way it increases the degrees of freedom of the other endoscopic instruments described herein which can be inserted through the tool channel. The tool channel 1122 directs the instrument laterally as it includes a pre-bent angle. The tool channel has its own axial (longitudinal) movement and its own rotation. The axial movement controls the distance of the retractor petals 414 from the target tissue; the rotation enables the instrument to move side to side. As described above, once the tool channels 1122, 1124 are in the desired position with respect to the polyp C, they can be considered as defining a fixed curve. This means that when the retractor 100 is axially advanced, it moves closer to the target polyp C, without a change in curvature and without a change in their axial position with respect to the polyp C, thus providing an extra degree of freedom. Each of the tissue retractors of FIGS. 1-8G can be inserted through the tool channels 1122, 1124 or alternatively directly through the lumen of the catheter.

In an alternate embodiment, retractor 400 has a specifically designed tool channel for use therewith instead of utilizing the tool channel 1122. In such embodiment, the tool channel (outer sheath) 412 can be composed of a metal such as nitinol, with a pre-bent tip to a desired angle, e.g., 45 degrees, 60 degrees, 90 degrees, or other angles. When inserted through the catheter, the pre-bent distal tip is substantially straightened, and when it is exposed from the outer sheath 414 it returns to its pre-bent angle. The tissue retractor, i.e., central wire 402 (and attached hypotube and inner sheath) are non-removably positioned within the outer sheath 414. The retractor petals 414 (and wire 406) in a preferred embodiment are composed of a sufficiently soft wire so they do not affect the bend of the outer sheath 414 and their distal angle is controlled by the bending of the tip of the outer sheath 414.

Figure 30:
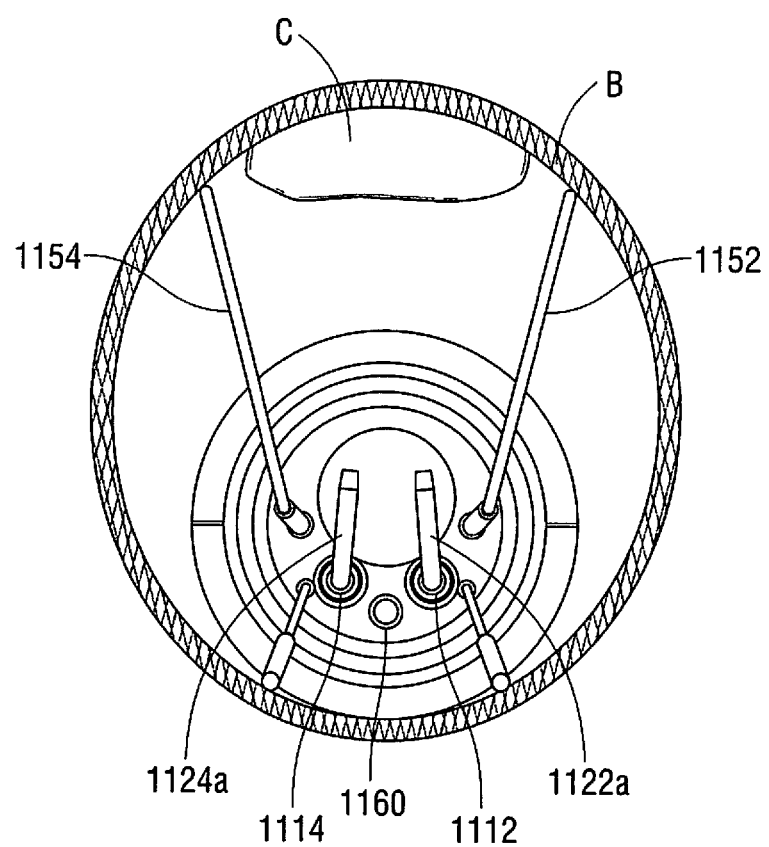
FIG. 30 is a front view of the system in the expanded position of the retractor system and showing two tool channels extending from the catheter.
Figure 31A:
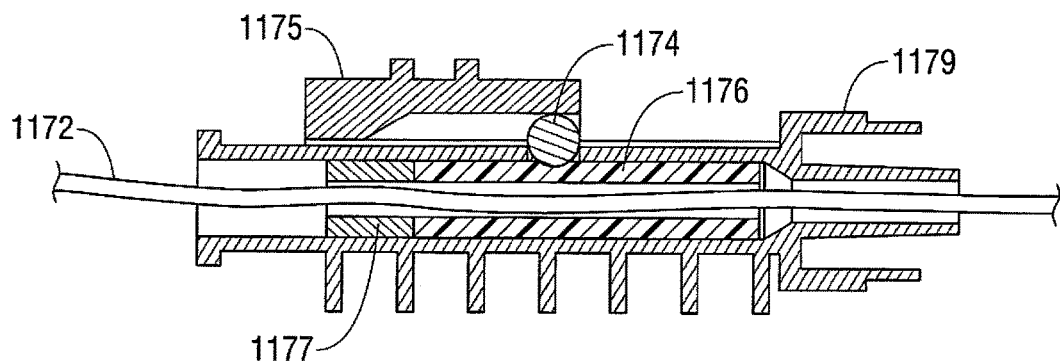
FIGS. 31A and 31B are cross-sectional views illustrating the switch for retaining the suture for closing the covering (bag).
Figure 31B:
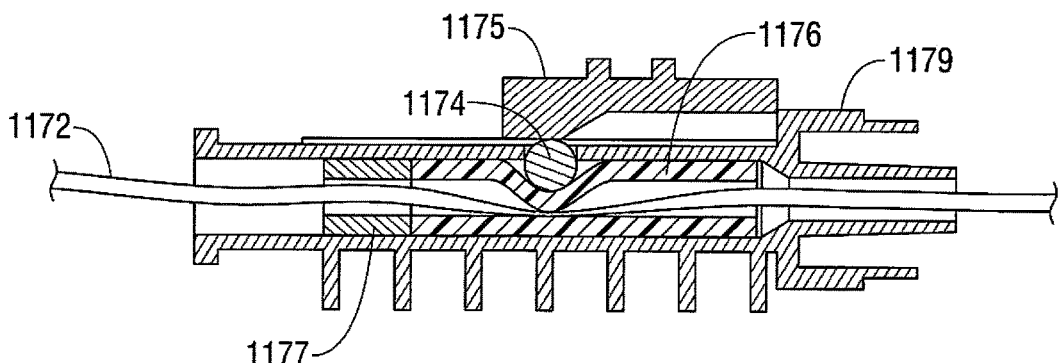

Also note that due to the angles of the tool channels 1122, 1124 and thus the endoscopic instruments inserted therethrough, tissue triangulation can be achieved as depicted by the dotted lines in FIG. 30.

Figure 26:
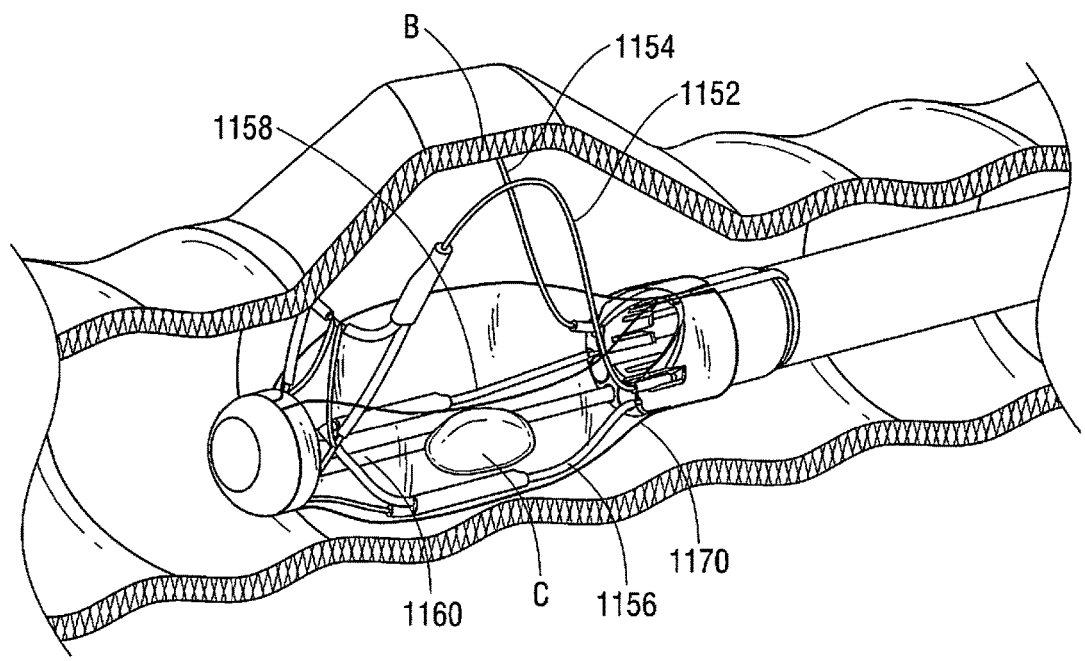
FIG. 26 is a view similar to FIG. 25 showing the lesion which has been removed from the colon wall by the dissecting instrument placed within the retractor system.
Figure 27:
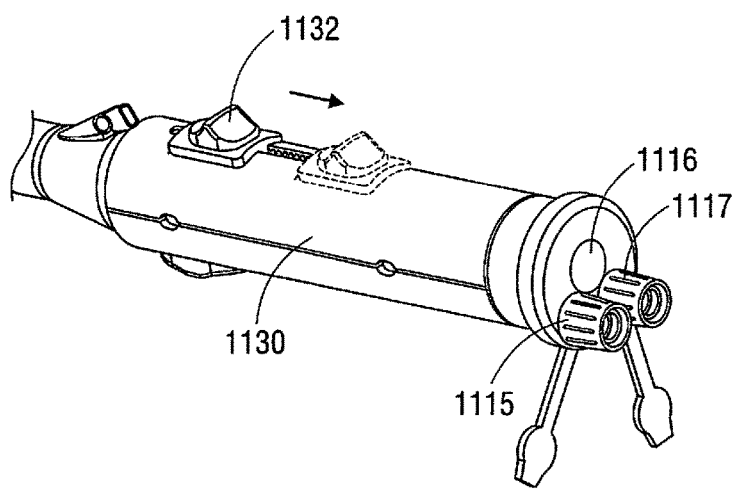
FIG. 27 is a perspective view of the proximal end of the catheter showing proximal movement of the actuator to return the retractor system to the collapsed position for removal from the colon.

After removal of the polyp C from the colon wall B, it is placed within the cover 1170 as shown in FIG. 26, ready for removal from the body. Actuator 1134 can be moved proximally to return the retractor system to the more flexible condition if desired. Actuator 1132 is moved proximally in the direction of the arrow of FIG. 27 to return the expanded retractor elements 1152, 1154 to their collapsed position of FIG. 28 for removal of the catheter 1110. The string or suture 1172 can then in some embodiments be tensioned to close the cover (bag) 1170 as shown in FIG. 29, forming a bag to encapsulate the polyp C. Note that the cover 1170 is preferably transparent so that the drawings illustrate the retractor elements, bridge members, beam, etc. However, to facilitate understanding of the cover 1170, FIG. 29 shows the retractor elements, bridge elements, beam etc. in phantom insider the bag/cover 1170.

FIGS. 32-42 illustrate alternative embodiments of the system of the present invention. The system includes floating (flexible) channels within the outer tube. In one embodiment, the floating channels are fixed at their proximal and distal ends; in another embodiment the floating channels are fixed at their proximal ends but are unattached at their distal ends. As can be appreciated from the discussion below, the floating channels reduce the overall stiffness of the catheter (outer tube) which would otherwise be stiffer if the channels were fixed along their entire length and did not float within the catheter. The floating channels also reduce kinking of the tool channels (flexible guides) inserted through the floating channels and reduce kinking of the tools inserted through the tool channels (or inserted directly through the floating channels in the embodiments where the tool channels are not utilized).

Figure 32:
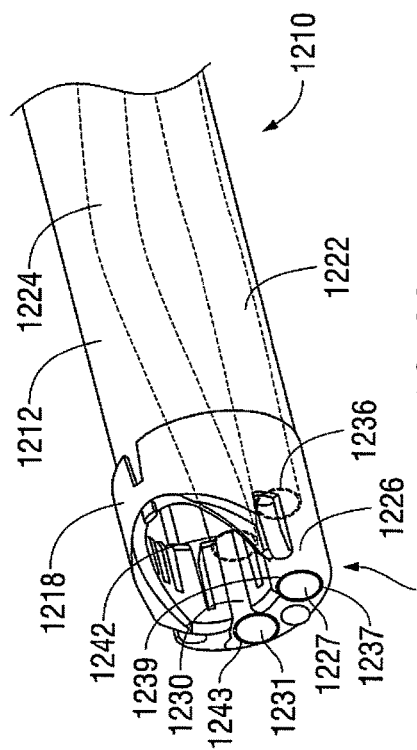
FIG. 32 is a perspective view of the distal end of the outer tube (catheter) of an alternate embodiment of the system showing two floating channels therein.
Figure 33:
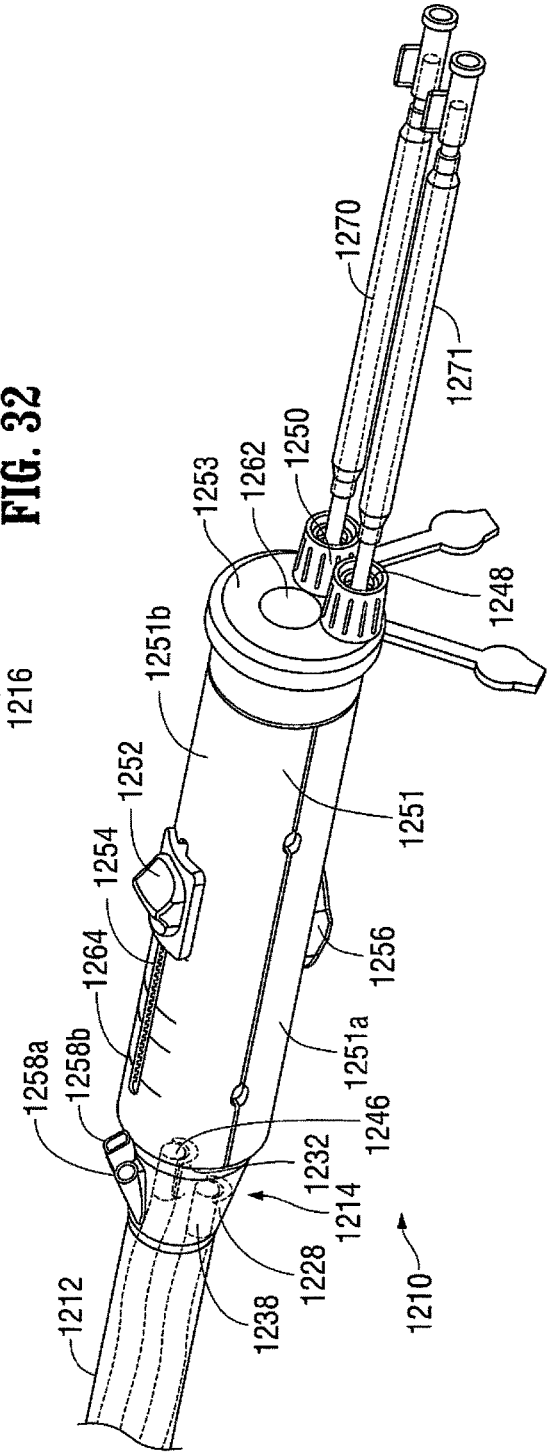
FIG. 33 is a perspective view of a proximal portion of the system of FIG. 32.
Figure 34:
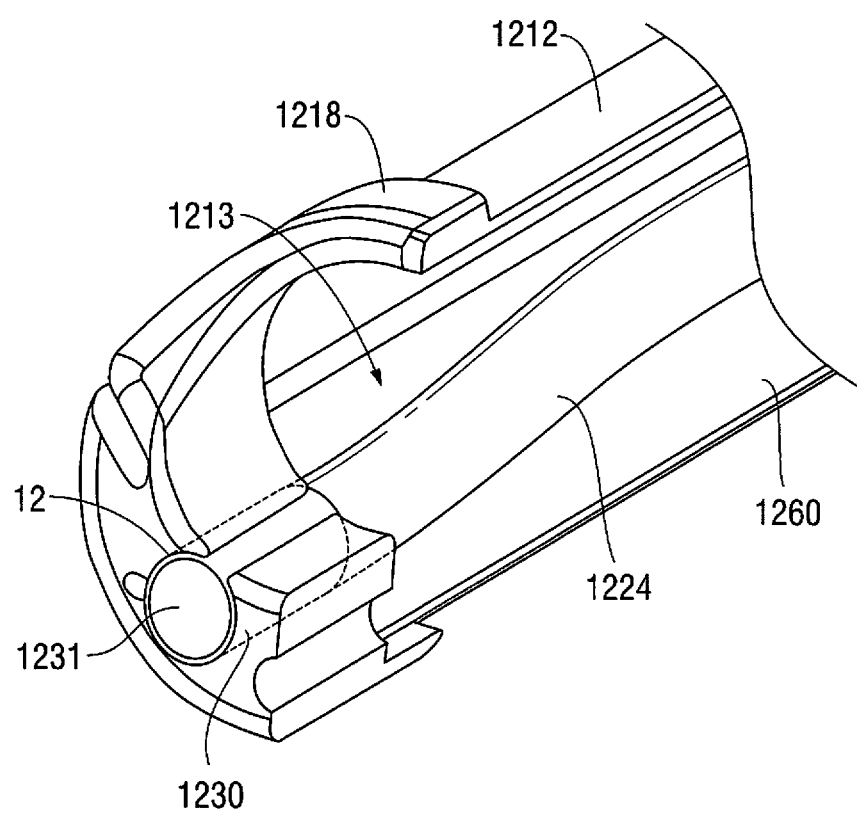
FIG. 34 is a close up cutaway view showing one of the floating channels of FIG. 32.

More specifically, in the embodiment shown in FIGS. 32-34, the system 1210 includes a flexible catheter or outer tubular member (main tube) 1212. The proximal portion of the outer tube 1212 is designated generally by reference numeral 1214 and the distal portion is designated generally by reference numeral 1216. A proximal end cap 1218 is positioned over distal portion 1216 of outer tubular member 1212.

A handle housing 1251 similar to handle housing 1130 of FIG. 11 described above is composed of two half shells 1251a, 1251b attached together. Shell 1251b has an actuator 1252 in the form of a sliding button, although other forms of actuators can be provided. Actuator 1252 is connected to cage wire push tubes, such as push tubes 1428, 1430 of FIGS. 40 and 42 described below, extending through outer tube 1212. Distal movement of the actuator 1252 along slot 1254 causes distal movement of the push tubes 1428, 1430 which causes the flexible elements of the cage to bow outwardly as described below. At the distal end of the handle housing 1251 are access ports 1258a, 1258b for inflow tubes (not shown) which can be part of a member (organizer) secured within the handle housing 1251 at a proximal region. At the proximal end of the handle housing 1251 is a handle end cap 1253 with an opening 1262 for entry of an endoscope into the outer tube 1212. Ports 1248, 1250 extend from proximal end cap 1253 to provide entry for the tool channels (flexible guides) 1270, 1271. The ports 1248, 1250 preferably include a valve to maintain insufflation when the tool channels 1270, 1271 are inserted therethrough and translated axially therein. Markings 1264 can be provided on the handle housing 1251 to indicate to the user the extent of distal travel of the actuator 1252 to control the size of the expanded cage. For example, the markings provided can be "4, 5 and 6" to indicate expansion of the cage to 4, 5 or 6 centimeters, providing the user with a general indication of the incremental expanded positions. Other markings and/or extent of expansions are also contemplated. The actuator 1252 can have a plurality of teeth or other retention structure to retain the actuator 1252 and thus the retractor elements in select extended positions.

Actuator 1256 on shell 1251a provides for rigidifying the cage by rigidifying a flexible beam. As described below, in alternate embodiments, a separate slidable beam for rigidifying the cage is not provided as alternative rigidifying structure is provided. As in the embodiment of FIGS. 17A and 17B, in this embodiment of FIG. 33, a stiffener member in the form of a rigid beam is operatively connected to actuator 1256 so that distal movement of the actuator 1256 advances the stiffener distally either within a lumen of the flexible element or over the outer surface of the flexible element to provide a stiffer structure. Actuator 1256 can be moved proximally to unstiffen the flexible element to facilitate collapse of the retractor system.

With reference to the cross-sectional view of FIG. 37A, the outer tube (catheter) 1212 in this embodiment has a single lumen 1213. This lumen 1213 is dimensioned to receive 1) an endoscope 1200, such as the endoscopes described above; and 2) two flexible channels 1222, 1224. The two flexible channels 1222, 1224 are in the form of flexible tubes and float inside the lumen 1213. That is, the two floating channels 1222, 1224 have intermediate portions that can move radially (laterally) within the lumen 1213 of the outer tube 1212. Stated another way, the floating channels 1222, 1224 are unconstrained within the outer tube 1212 so they can bend relative to the outer tube 1212 so their bending action does not need to follow that of the outer tube 1212. In this manner, when the outer tube 1212 is inserted in the body lumen and needs to bend to accommodate the curvatures of the body lumen, e.g., the gastrointestinal tract, the flexibility of the outer tube 1212 is maintained since the floating channels 1222, 1224 can move within the lumen 1213. As can be appreciated, if the two channels were fixed with respect to the outer tube 1212 so there was no bending or movement with respect to the outer tube 1212, and the channels were forced to bend in conformity with the outer tube 1212, the outer tube 1212 would be much stiffer as the channels would have to carry the bending stresses which could limit bending of the catheter and/or cause kinking of the tool channels or tools extending through the channels of the catheter. Thus, in the embodiments of the present invention which include the floating channels, these advantages of increased flexibility are achieved. It should be understood that any of the systems disclosed herein could be provided with floating channels. Likewise, any of the systems disclosed herein could be provided without floating channels. FIG. 37B provides by way of example a location of the floating channels 1222, 1224 when they are moved within the catheter 1212 as it is bent. Clearly, floating channels 1222, 1224 will move to various other positions in response to catheter bending.

Also, by providing a single lumen in this embodiment to receive the endoscope and the tool channels, rather than separate lumens which would require additional wall structure, a smaller diameter catheter can be provided which also reduces the overall stiffness of the catheter.

The endoscope 1200 in the embodiment of FIG. 37A also floats within the lumen 1213. That is, the endoscope occupies only a certain region of the lumen 1213 and can move radially (laterally) within the lumen 1213 of outer tube 1212 to increase the flexibility of the system. Thus, the endoscope 1200 can move relative to the outer tube 1212 in a similar manner as the floating channels 1222, 1224 can move relative to the outer tube 1212.

In one embodiment by way of example, the internal diameter of the lumen 1213 of the outer tube 1212 ranges between about 5 mm and about 50 mm and is preferably about 10 mm to about 20 mm. Each of the floating channels preferably has an outer diameter of about 2 mm to about 10 mm, and preferably about 5 mm. The endoscope typically has a diameter of about 2 mm to about 20 mm and is preferably about 5 mm to about 12 mm. Thus, as can be appreciated, the floating channels and endoscope occupy only a small percentage of the internal lumen 1213, leaving sufficient room for movement. Note that other dimensions and thus ratios of the floating channels and endoscope to the internal diameter of the lumen 1213 are also contemplated for the systems disclosed herein.

In one embodiment, by way of example, the outer tube 1212 has a length, measured from the distal end of handle 1251 to a distal edge of end cap 1218 of about 10 cm to about 200 cm, and more preferably about 60 cm to about 90 cm. The floating channels 1222, 1224 have a length of about 10.1 cm to about 204 cm, and preferably about 60.5 cm to about 91 cm, thereby exceeding the length of the outer tube 1212. Other dimensions are also contemplated. This greater length of the floating channels 1222, 1224 in the embodiments where they are fixed at both the proximal and distal ends enables the floating movement.

Turning now to details of the floating channels and their securement within outer tube 1212, in the embodiment of FIGS. 32-34, channel 1222, referred to herein as a first flexible channel or a first floating channel or a first flexible tube, has a proximal end 1238 and an opposing distal end 1239. Channel 1224, referred to herein as a second flexible channel or a second floating channel or a second flexible tube, has a proximal end 1246 and an opposing distal end 1249. Note the terms "first" and "second" to describe various components of the systems of the present invention are used herein for ease of description. Note in the embodiments of FIGS. 32-42, two floating channels are provided. It is also contemplated that only one floating channel is provided or more than two floating channels are provided.

Positioned with the outer tube 1212 at a distal end is a first fixed distal tube 1226 which forms a pocket for the first floating channel 1222. First distal tube 1226 has an opening 1227, a proximal edge 1236 and a distal edge 1237. In some embodiments, instead of an opening 1227 the distal end can be closed. Preferably, distal edge 1237 is substantially flush with the distal edge of distal end cap 1218. At the proximal end of the system, positioned either within the outer tube 1212 or alternatively at a distal region of the handle housing 1251, is a first fixed proximal tube 1228.

Also positioned with the outer tube 1212 at a distal end is a second fixed distal tube 1230 which forms a pocket for the second floating channel 1224. Distal tube 1230 has an opening 1231, a proximal edge 1242 and a distal edge 1243. In some embodiments, instead of an opening 1231 the distal end can be closed. Preferably, distal edge 1243 is substantially flush with the distal edge of distal end cap 1218. At the proximal end of the system, positioned either within the outer tube 1212 or alternatively at a distal region of the handle housing 1251, is a second fixed proximal tube 1232 having a proximal edge 1246. The first and second proximal tubes 1228, 1232 are preferably attached to an inner wall of the outer tube 1212 or handle housing 1251 by bonding or welding or other attachment methods. Similarly, the first and second distal tubes 1226, 1230 are preferably attached to an inner wall of the outer tube 1212 by bonding or welding or other attachment methods. Note in FIG. 33, the fixed proximal tubes 1228 or 1232 are shown cutaway (into a half cylinder) for clarity, it being understood that the tubes can be cylindrical in configuration like the distal fixed tubes 1226, 1230. Other configurations for the fixed distal and proximal tubes are contemplated.

The distal end of the first flexible channel (tube) 1222 is positioned within the first fixed distal tube 1226 and secured thereto such as by bonding or welding or other attachment methods. It can terminate in any fixed position within the distal tube 1226, and in the illustrated embodiment, terminates at the distal end of the distal tube 1226. The proximal end 1238 of first flexible channel 1222 is positioned within the first fixed proximal tube 1228 and secured thereto such as by bonding or welding or other attachment methods. It can terminate in any fixed position within the proximal tube 1228, and in the illustrated embodiment, terminates at the proximal end of the proximal tube 1228. In this manner, the first flexible channel 1222 is fixed with respect to the outer tube 1212 at its proximal end and at its distal end. However, it remains unattached in an intermediate portion between the proximal and distal end, e.g., along its length between its two fixed ends, so it can float within the outer tube 1212. Similarly, the distal end of the second flexible channel (tube) 1224 is positioned within the second fixed distal tube 1230 and secured thereto such as by bonding or welding or other attachment methods. It can terminate in any fixed position within the distal tube 1230, and in the illustrated embodiment, terminates at the distal end of the distal tube 1230. The proximal end of second flexible channel 1224 is positioned within the second fixed proximal tube 1232 and secured thereto such as by bonding or welding or other attachment methods. It can terminate in any fixed position within the proximal tube 1232, and in the illustrated embodiment, terminates at the proximal end of the proximal tube 1232. In this manner, the second flexible channel 1224 is fixed with respect to the outer tube 1212 at its proximal end and at its distal end. However it remains unattached in an intermediate portion between the proximal and distal end, e.g., along its length between its two fixed ends, so it can float within the outer tube 1212.

Figure 19A:
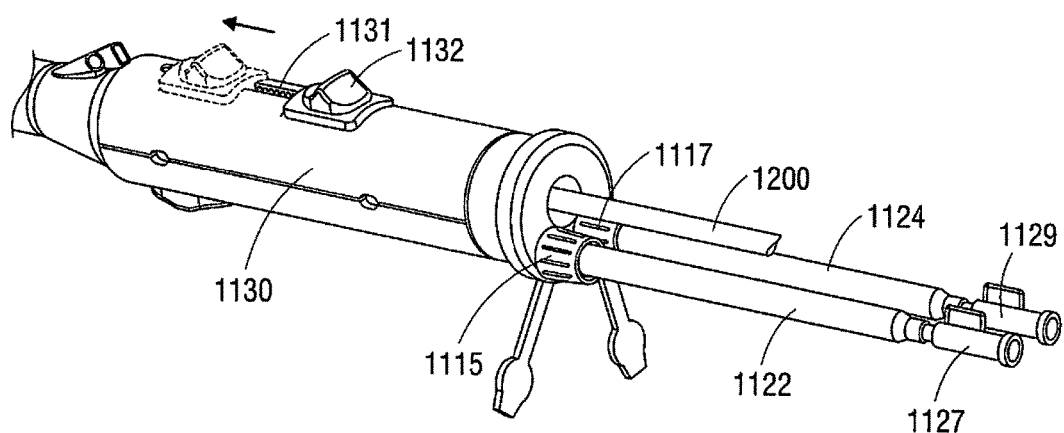
FIG. 19A is a perspective view illustrating the tool channels inserted into the catheter of FIG. 11
Figure 19B:
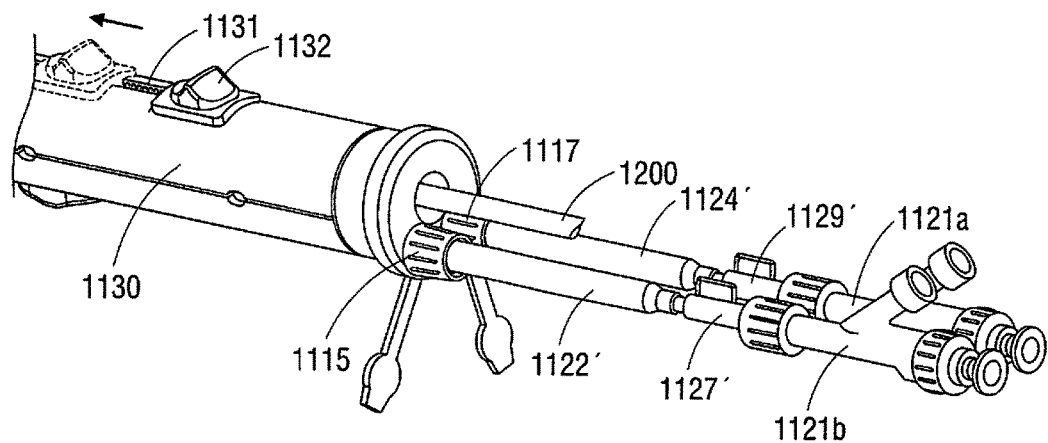
FIG. 19B is a perspective view illustrating an alternative embodiment of the tool channels.
Figure 20A:
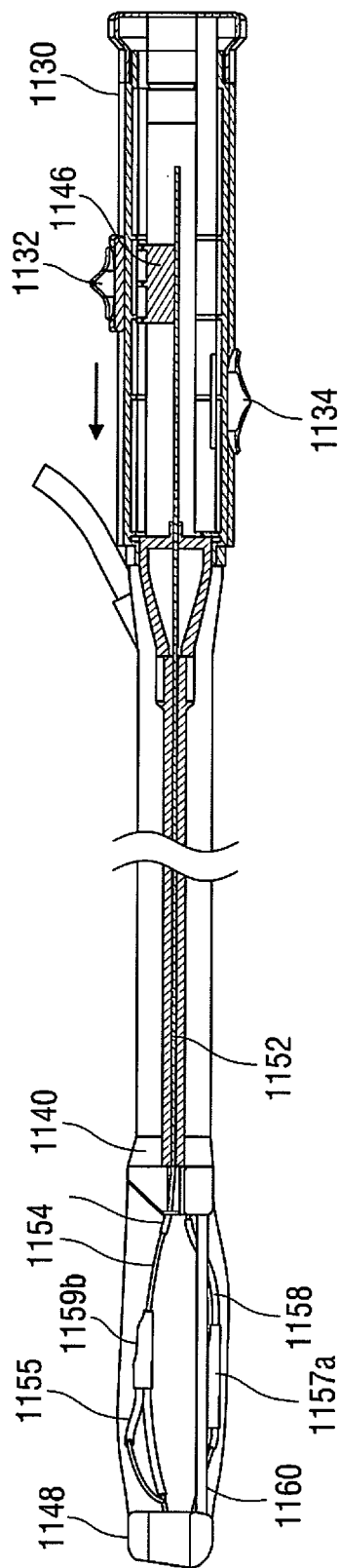
FIGS. 20A and 20B are side views in partial cross-section showing movement of the actuator from a proximal position to a distal position to move the retractor system to the expanded position.
Figure 20B:
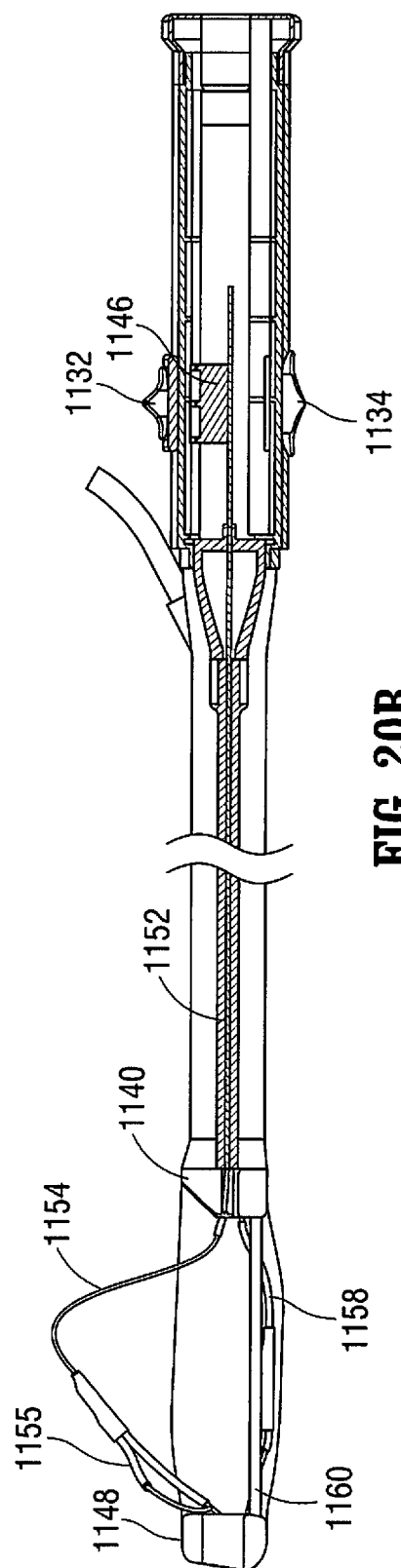

First and second flexible guides or tool channels 1271, 1270 (FIG. 33) are inserted through ports 1248 and 1250 in the same manner as flexible guides (tool channels) 1122, 1124 of FIG. 19A. The flexible guides 1271, 1270 extend through floating channels 1222, 1224, respectively, to emerge out the distal ends into the chamber. Note flexible guides 1271 and 1270 can in some embodiments be composed of a Pebax tubing, an overlying PVC tubing and polyolefin shrink tubing over the PVC tubing. The other flexible guides disclosed herein can also be composed of such structure. This provides a balance between flexibility and rigidity, and also beefs up the proximal end to facilitate handling by the user. Note the flexible guides 1271, 1270 emerge from the proximal cap 1218 and bend at their distal tips in the same manner as flexible guides (tool channels) 1122, 1124. Therefore, since the flexible guides 1271, 1270 are identical in function for guiding/bending working instruments inserted therethrough, for brevity they will not be discussed further since the discussion of flexible guides 1122, 1124 above is fully applicable to flexible guides 1271, 1270. Note for clarity the flexible guides are not shown in the other Figures, it being understood that they would function in the manner of FIGS. 21-25.

Figure 35A:
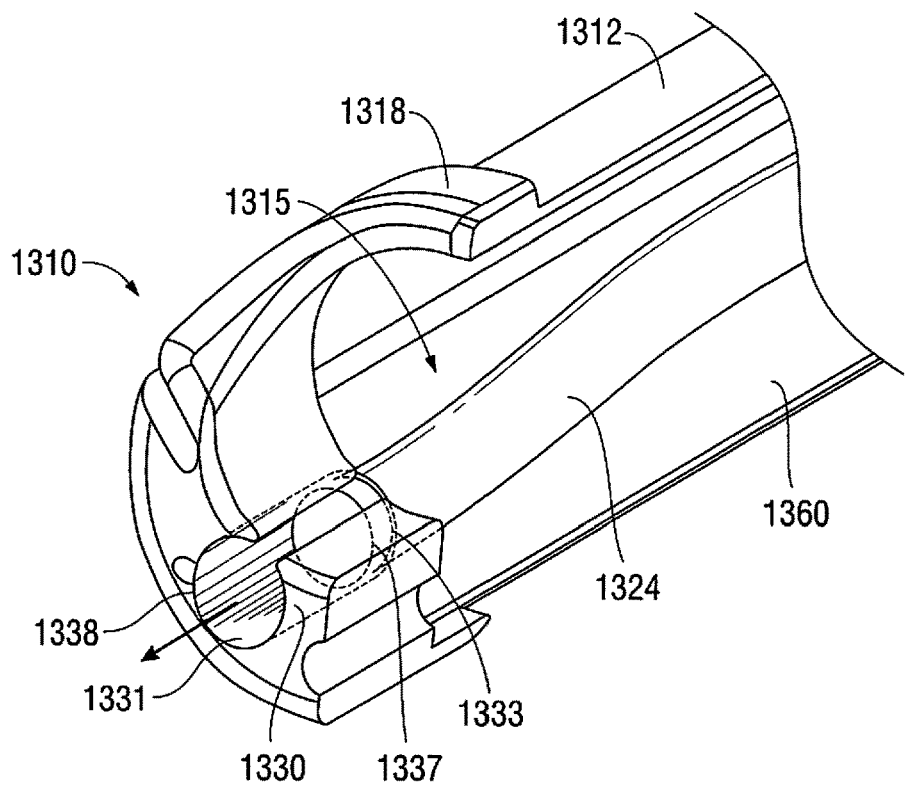
FIG. 35A is a view similar to FIG. 34 showing an alternate embodiment of the floating channel.
Figure 35B:
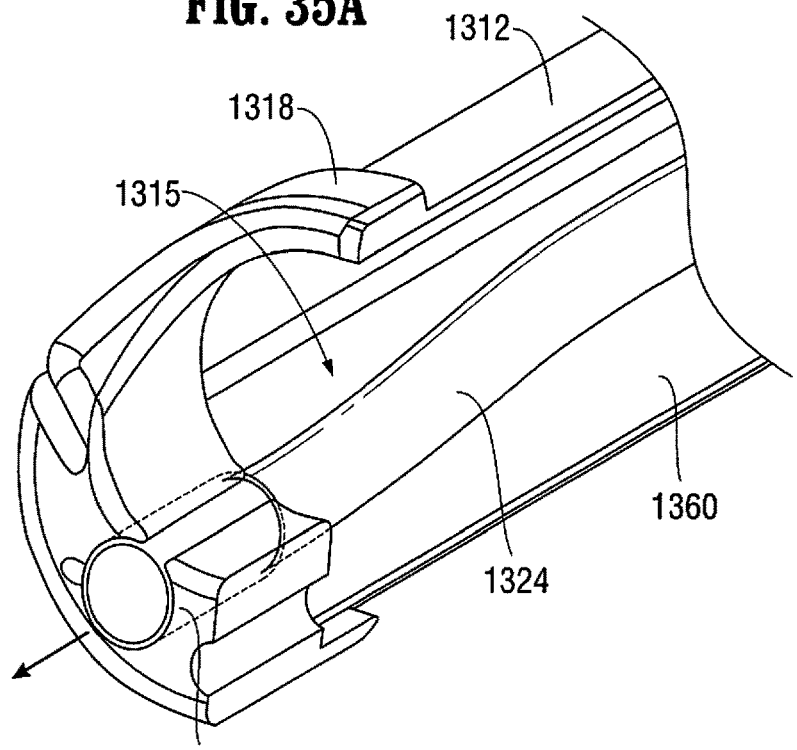
FIG. 35B is a view similar to FIG. 35A showing the floating channel advancing within the fixed distal tube.
Figure 35C:
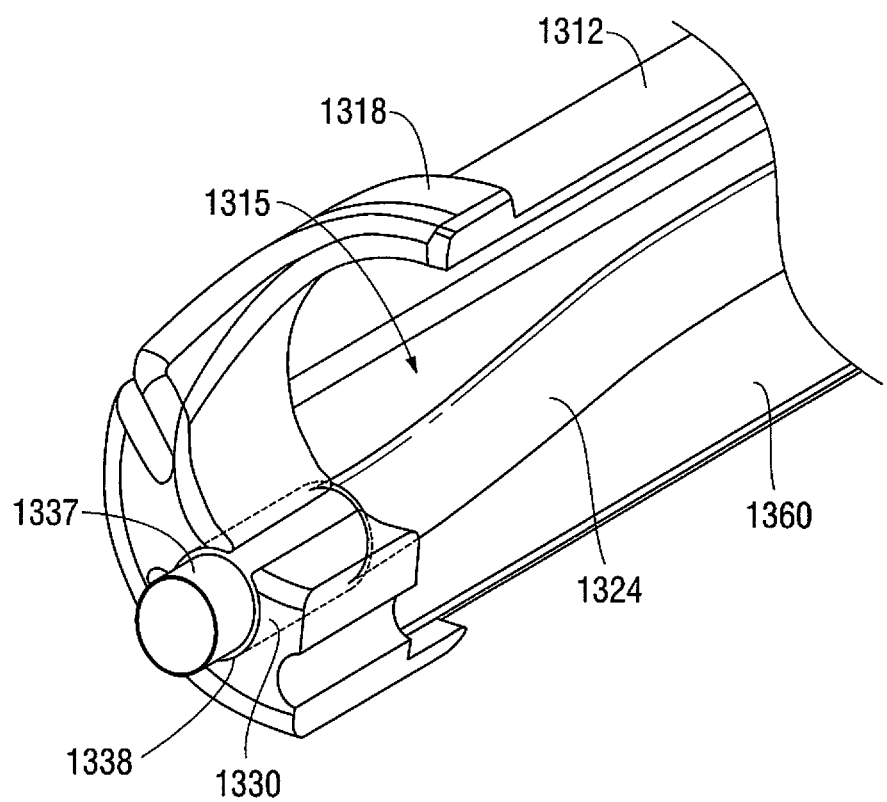
FIG. 35C is a view similar to FIG. 35B showing movement of the floating channel beyond the fixed distal tube.

In an alternate embodiment of FIGS. 35A-35C, the floating (flexible) channels are fixed at their proximal end but remain free (unattached) at their distal ends. More specifically, FIGS. 35A-35C illustrate a cutaway view of the system so that only one of the floating channels, the second floating channel 1324, is illustrated. The first floating channel is attached and configured in a similar fashion as second floating channel 1324. Second floating channel 1324 is attached at its proximal end in the same manner as floating channel 1224, i.e., attached within a fixed proximal tube. The first floating channel 1322 is not shown in FIGS. 35A-35C but is shown in FIG. 38 and is attached at its proximal end in the same manner as first floating channel 1222, i.e., attached within a fixed proximal tube. The floating channels 1322, 1324 differ from the floating channels 1222, 1224 of FIG. 32 in that they are unattached at their distal ends. Consequently, the floating channels 1322, 1324 form telescoping channels within the outer tube (or catheter) 1312.

More specifically, with continued reference to FIGS. 35A-35C and FIG. 38, a first fixed distal tube 1326 is attached within the outer tube 1312 adjacent proximal end cap 1318 positioned over the outer tube (catheter) 1312 of the system 1310. First fixed distal tube 1326 forms a pocket for the first floating channel 1322. Distal tube 1326 has a lumen extending therethrough, a proximal edge 1325 and a distal edge 1329. Preferably, distal edge 1329 is substantially flush with the distal edge of proximal end cap 1318. A second fixed distal tube 1330 is attached within outer tube 1312 adjacent the proximal end cap 1318 and forms a pocket for the second floating channel 1324. Distal tube 1330 has a lumen 1331 extending therethrough, a proximal edge 1333 and a distal edge 1338. Preferably distal edge 1338 is substantially flush with the distal edge of proximal end cap 1318. Second floating channel 1324 has a distal end 1337 which in the position of FIG. 35A is fully within the second fixed distal tube 1330. Upon bending of the outer tube 1312 in one direction, the second floating channel 1324 moves distally to the position of FIG. 35B. Upon additional bending, the floating channel 1324 can extend beyond the distal edge 1338 of the second fixed distal tube 1330 (and beyond the distal edge of the proximal end cap 1318) as shown in FIG. 35C. FIG. 38 (and FIG. 39B) illustrates the effect in bending of the outer tube 1312 in the opposite direction of FIG. 35C. As shown, the second floating channel 1324 remains within the lumen 1331 of the second fixed distal tube 1330 while the distal end 1327 of first floating channel 1322 extends distally beyond the distal edge 1329 of first fixed distal tube 1326 (and beyond the distal edge of the proximal end cap 1318).

Stated another way, the floating channels 1322, 1324 are unconstrained within outer tube (catheter) 1312 and take the shortest path when the outer tube 1312 is bent. Thus, the movement readjusts their position to adjust for the length difference on bending of the outer tube 1312. Note the floating channels 1322, 1324 can also slightly rotate during bending of the outer 1312 to compensate for stress applied to the floating channels during bending. Consequently, this prevents the eccentric positioned channels from being stretched on the outer portion of the curvature and buckling on the inner portion of the curvature. The floating channels can move around within lumen 1315 of outer tube 1312 and take any shape to accommodate bending to increase the flexibility of the device.

Note that in FIG. 35C the outer tube 1312 is bent in a first direction so that second floating channel 1324 on the inside curvature of the outer tube 1312 is advanced distally beyond distal tube 1330. In FIG. 38, the outer tube 1312 is bent in a second opposite direction so that the first floating channel 1322 on the inside curvature of the outer tube 1312 extends beyond the distal tube 1326.

The fixed distal tubes 1326, 1330 which form pockets for the respective floating channels 1322, 1324 are dimensioned so their length exceeds the largest extent of movement in response to the greatest curvature of the outer tube 1312 as a result of bending of the outer tube 1312 during use. This ensures that the floating channels 1322, 1324 will not retract out of the proximal end of the respective fixed distal tubes 1326, 1330, In a preferred embodiment, the length of the distal tubes 1326 and 1330 are between about 1.5 cm to about 3 cm, and preferably about 2 cm. Other dimensions are also contemplated.

Flexible guides identical to flexible guides 1270, 1271 of FIG. 33 and/or flexible guides 1122, 1124 of FIGS. 19-25 are inserted through the floating channels 1322 and 1324 in the same manner as described above so that endoscopic working instruments can be inserted into the chamber formed by the flexible elements for performing the procedure. Note, alternatively, endoscopic working instruments can be inserted directly through the floating channels of any of the embodiments herein without the intermediary flexible guides. Such direct insertion of instrumentation without flexible guides (tool channels) is also described above as an alternative system and method.

The working instruments can include graspers for example. A dissecting/cutting instrument can be inserted through the flexible guide in the floating channel, or alternatively inserted through a working channel of the endoscope. Thus, various working instruments can be inserted through the flexible channels and endoscope channel(s).

The flexible guides described herein, e.g., flexible guides 1270, 1271, can be color coded to improve the system's usability. For example, flexible guide 1270 can be of a first color, such as red, and flexible guide 1271 can be of a second color, such as black. In this way, when the user is manipulating the flexible guides 1270, 1271 at their proximal ends outside the patient's body, the user will more readily see the corresponding color coordinated tip being manipulated within the expanded cage. Note the entire flexible guide can have the same color or alternatively the matching color can be only at the proximal end visible to the user and the distal end visible by the endoscope. It should also be appreciated, that instead of color coding, other indicia can be provided so the user can match the proximal end of the flexible tube with the distal end within the chamber.

Figure 36:
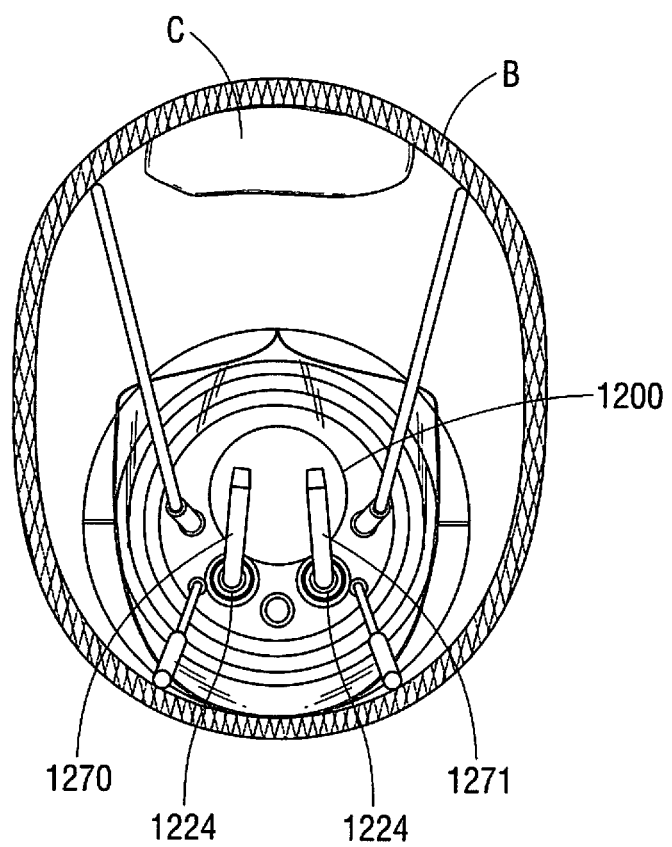
FIG. 36 is a front view of the system of FIGS. 32 and 33 shown within the colon.
Figure 39A:
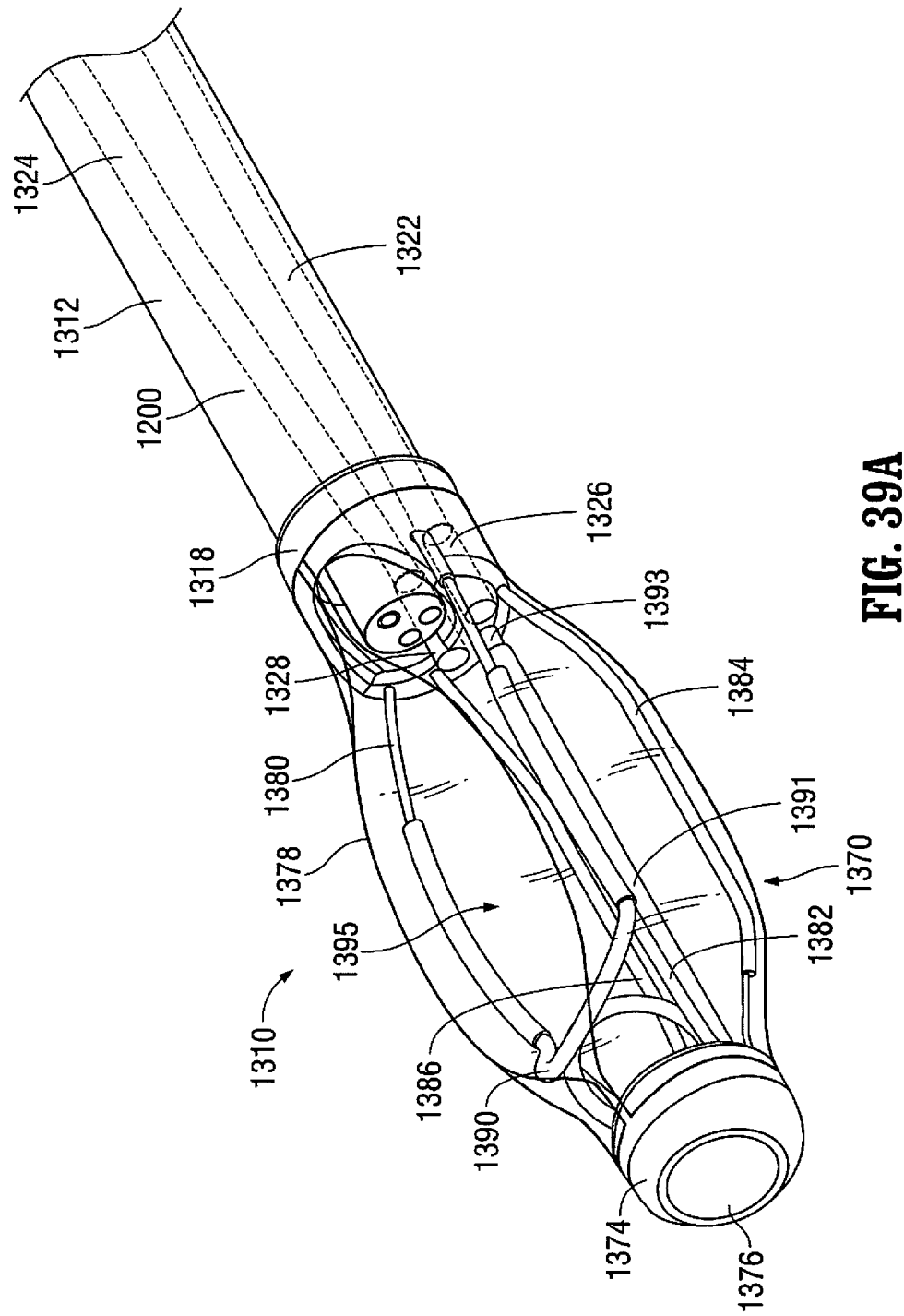
FIGS. 39A and 39B are side perspective views of the distal portion of the system of FIG. 38 showing the effect of bending of the outer tube and movement of the floating channels, and the retractor system shown in the non-expanded configuration.
Figure 39B:
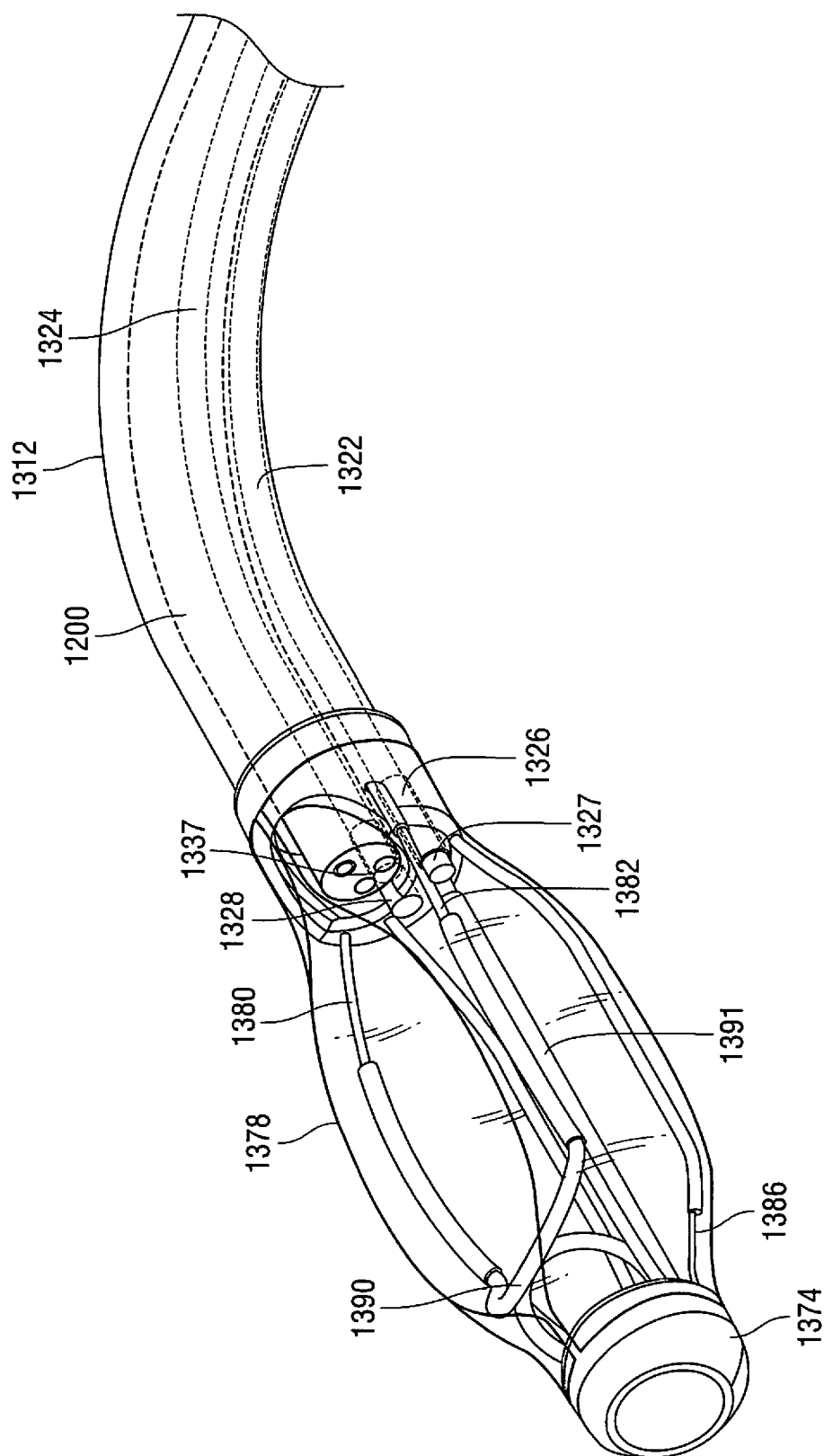
Figure 39C:
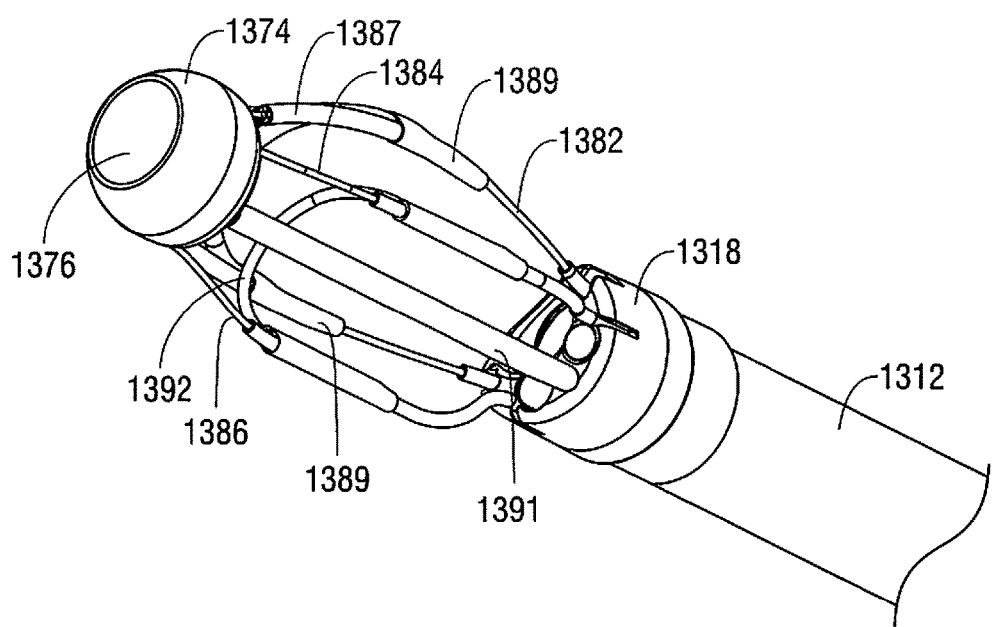
FIG. 39C is a bottom perspective view of the retractor system of FIG. 39A.

FIGS. 39A-39C illustrate the distal portion of the system 1310 to show the retractor elements in the expanded configuration to form the asymmetric cage to create a working space for the surgical procedure. The retractor system 1370 is identical to the retractor system 1150 of the embodiment of FIG. 21A and therefore when expanded from its collapsed insertion position forms a working space expanding system and in certain surgical procedures a body lumen reshaping system which reshapes the body lumen to form an asymmetric space to increase the working space for the maneuverability of the endoscopic instruments through the flexible guides of the system. That is, the retractor system creates a self-contained "surgical suite" which forms an expanded area within the body lumen for the surgeon to perform the surgical procedure within the created space. By reshaping the body lumen, the working space is maximized without overstretching the body lumen. Such working space maximization increases the distance between the target tissue and the end effectors of the endoscopic instruments, hence improving maneuverability of the instruments during the surgical procedure. Note the flexible tool channels (flexible guides) and endoscopic instruments are not shown in these drawings for clarity but would operate in the same manner as in FIGS. 21-25. The retractor system of system 1210 of FIGS. 32 and 33 is identical to the retractor system 1370 of system 1310 and therefore the discussion of the structure and function of the retractor system 1370 is fully applicable to the retractor system of system 1210. FIG. 36 discussed below illustrates an example of the reshaping of the body lumen to a more oval-like configuration.

As noted above, retractor system 1370 is identical to retractor system 1150 and includes flexible retractor elements 1380, 1382 which create the working chamber (space) within the body lumen and form an asymmetric cage. Flexible retractor elements 1384, 1386 form the base of the retractor system 1370. Movement of the retractor elements 1380, 1382, 1384 and 1386 is the same as retractor elements 1152, 1154, 1156 and 1158 described above and/or the same as movement of the retractor elements of FIGS. 40-42 described below. The retractor system 1370, also like retractor system 1150, can include a bridge member 1390 spanning retractor elements 1380,1382 and optionally a bridge member 1392 spanning retractor elements 1384, 1386, which are configured and function in the same manner as aforedescribed bridge members 1155, 1157 and therefore for brevity are not described herein again in detail as the description above for bridge members 1155, 1157 and their alternatives are fully applicable to the retractor system 1370.

The retractor elements 1380, 1382, 1384, 1386 can be made of substantially flexible materials and are preferably formed of a wire composed of nitinol. A layer of soft compatible material, but preferably PTFE tubing 1387, can be positioned over a portion of the wires. A polyolefin heat shrink 1389 can be positioned over the retractor portion of the elements and bridge member to retain the bridge members. Note the retractor elements angulate at the distal end, i.e., pivot from the distal cap 1374. To bulk up the retractor elements adjacent this region, a covering material such as the PTFE tubing can be provided.

Flexible tube or beam 1391 in the form of a rod or tube has a lumen to receive a stabilizing or rigidifying structure such as rigid tube or rod 1393. (Alternatively, the rigid tube or rod can be slid over beam 1391). Flexible beam 1391 and rigidifying structure 1393 are identical to flexible beam 1160 and rigid beam 1162 of FIGS. 17A, 17B described above. Therefore, for brevity, further details of these components are not provided herein since the structure and function of the beams 1160, 1162 provided in detail above are fully applicable to the beams 1391, 1393. An actuator like actuator 1256 of FIG. 33 is operably connected to the rod 1393 for sliding movement with respect to beam 1391 to increase the rigidity of the cage. Alternative structure for the rigidifying structure described above, such as sliding a rigidifying structure over a flexible beam, are also fully applicable as alternatives to the rigidifying structure of the retractor system 1370 of FIG. 39A and the retractor system of the system 1210 of FIGS. 32 and 33.

Figure 28:
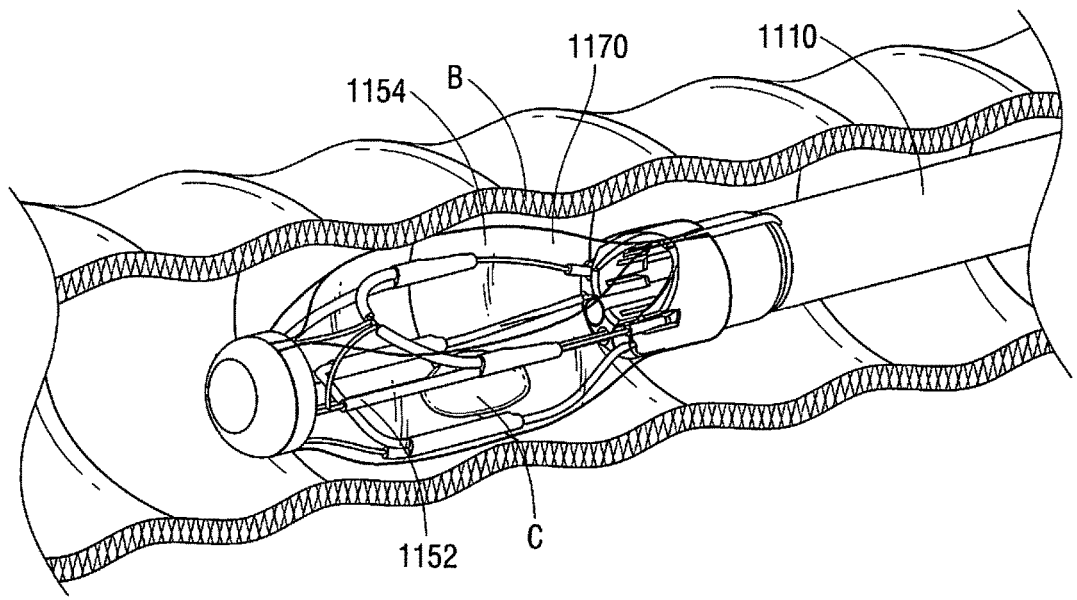
FIG. 28 is a view similar to FIG. 26 showing the retractor system in the collapsed position.
Figure 29:
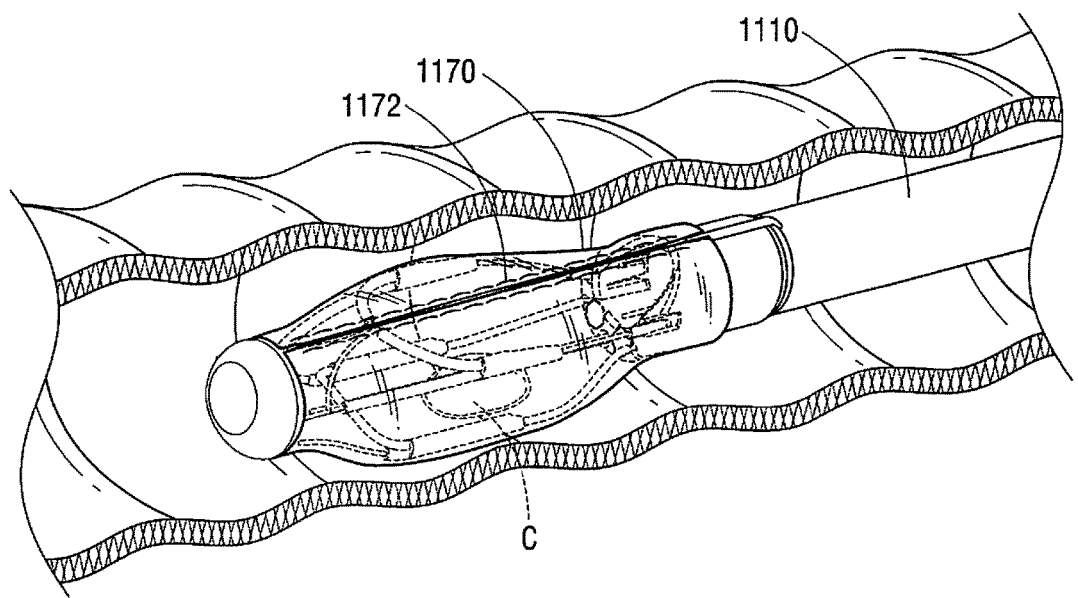
FIG. 29 is a view similar to FIG. 28 showing the covering member closed to encapsulate the lesion for removal.

A covering or cover 1378 identical to cover 1170 of FIGS. 28 and 29 of Figure is provided. The cover 1378 covers the retractor elements 1380, 1382, 1384, 1386 and in the expanded position of the retractor system 1370 has an opening 1395 for access to the tissue. Further details of the cover 1395 are not provided herein since the cover 1395 is identical in structure and function to cover 1170. Also, the various embodiments of the covers described above are fully applicable to the cover for the systems of FIGS. 32-42.

In alternate embodiments, the pursestring to close the cover 1378 of FIGS. 32-42 or the cover of any over the aforedescribed covers is eliminated and reliance is on the cover itself. Elimination of the pursestring simplifies the device by providing fewer components and reduces the steps in the surgical procedure. In embodiments without the pursestring, when the tissue, e.g., the severed polyp, is pulled into the cage formed by the retractor elements, and the retractor elements return to their non-expanded position to collapse the cage, the cover closes down on the captured tissue, e.g., the polyp, to prevent or minimize seeding of the pathological tissue, e.g., cancerous tissue, during removal. The grasper can also maintain its grip on the severed tissue so the grasped tissue and catheter are removed together from the body lumen. The target tissue, e.g., polyp, during the procedure and during its removal from the body would typically be located inside the cage and practically isolated by the cage and its cover from the surrounding innocent tissues.

Figure 40:
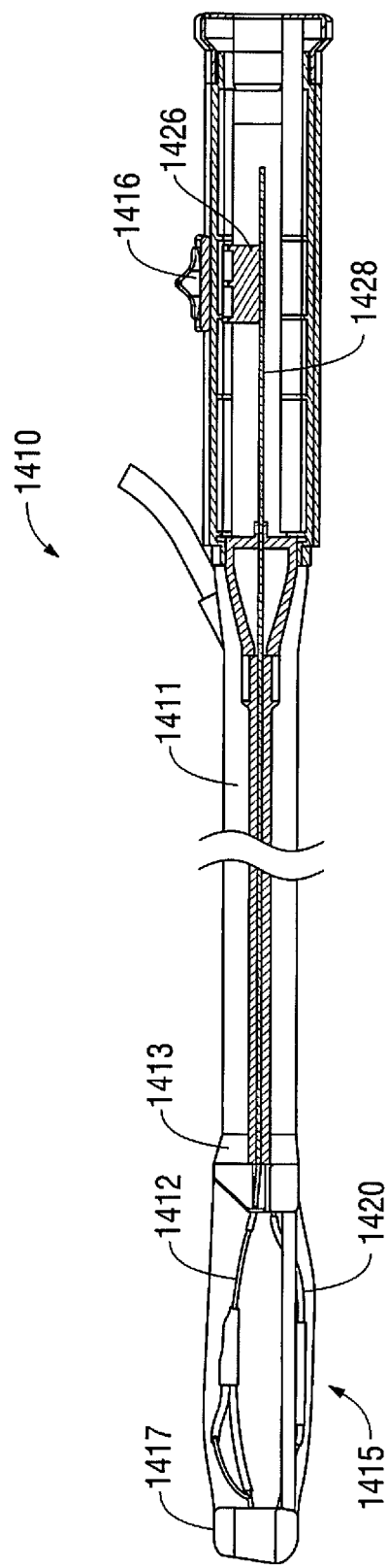
FIG. 40 is a longitudinal cross-sectional view of an alternate embodiment of the system with the retractor system shown in the collapsed insertion position.
Figure 41:
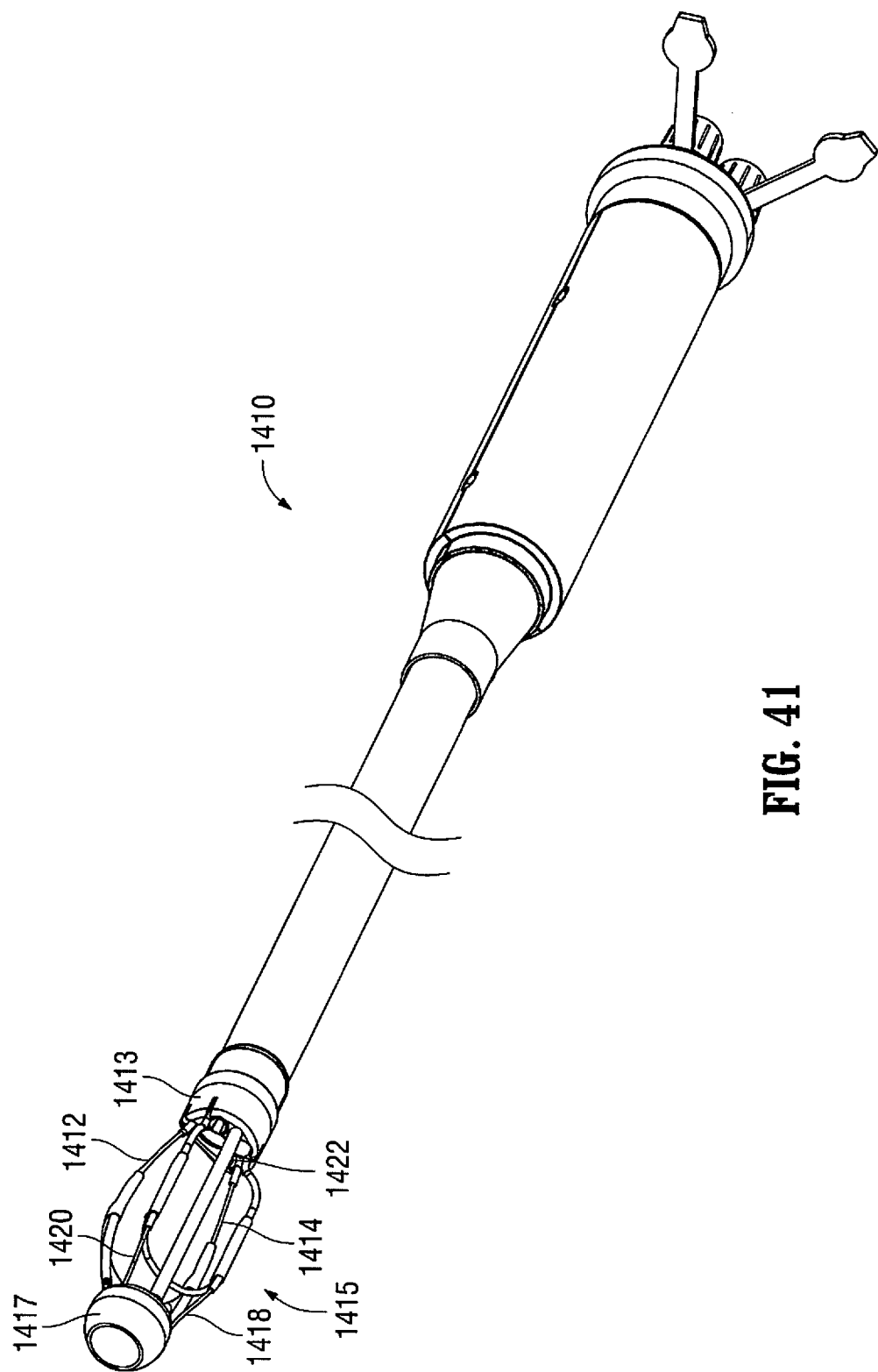
FIG. 41 is a bottom perspective view of the system of FIG. 40 with the retractor system shown in the non-expanded configuration.
Figure 42:
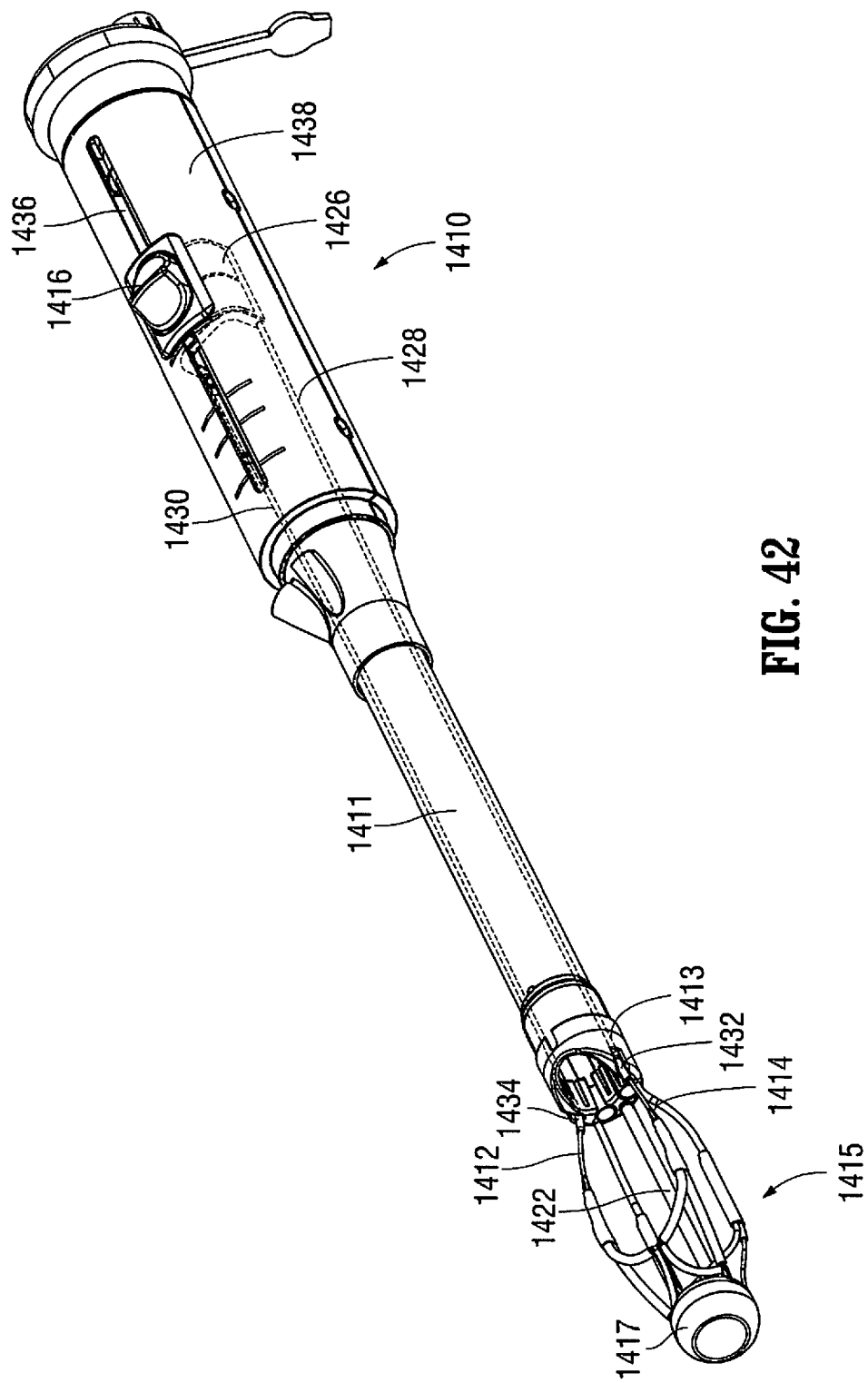
FIG. 42 is a side perspective view of the system of FIG. 41.

FIGS. 40-42 illustrate an alternative retractor system of the present invention. The retractor system 1415 of system 1410 is identical to the retractor system 1370 FIG. 39A (and system 1150 of FIG. 17C) except for the rigidifying structure. In this embodiment, instead of a movable beam to stiffen an otherwise flexible element, an element of the retractor system has inherent stiffness characteristics to stiffen the overall retractor system 1415. More specifically, retractor system 1415 has flexible retractor elements 1412, 1414 which expand (bow outwardly) to form the chamber (cage) to create the working space in the same manner as retractor elements 1380, 1382 described above. These flexible elements 1412, 1414 are expanded by movement of actuator 1416 in the same manner that movement of actuator 1252 (FIG. 33) expands flexible retractor elements 1380, 1382. That is, actuator 1416 is attached to block or carriage 1426 which contains a slot or opening for attachment of push cable 1428. Push cable 1430 is also attached within another slot or opening of block 1426. Thus, push cables 1428, 1430 are operatively connected at their proximal ends to actuator 1416. A connection tube 1432 connects push cable 1428 to flexible element 1414 and connection tube 1434 connects push cable 1430 to flexible element 1412. The connection tubes 1432, 1434 are at the distal end of the outer tube 1411 at the region of the proximal cap 1413. More specifically, a distal end of push cable 1428 is secured within connection tube 1432 and a proximal end of flexible retractor element 1414 is secured within connection tube 1432. A distal end of push cable 1430 is secured within connection tube 1434 and a proximal end of flexible retractor element 1412 is secured within connection tube 1434. Slidable advancement of actuator 1416 within slot 1436 of handle housing 1438 moves push cables 1428, 1430, distally which bows flexible elements 1412, 1414 outwardly to an expanded position due to their attachment at distal end cap 1417. Markings 1440 can be provided to indicate retractor element expansion as in FIG. 33.

Retractor system 1410 also has flexible elements 1418, 1420 forming the base of the cage and identical to retractor elements 1384, 1386 described above. Retractor system 1415, however, differs from retractor system 1370 (and 1150) in that a beam 1422 is provided which itself has sufficient rigidity to maintain the overall stiffness of the expanded cage when fairly mild forces are applied (e.g., weight of small portion of the intestinal wall, minor external intra-abdominal pressure, etc.) and limit bending of the cage with respect to the outer tube 1422 during use when fairly mild forces are applied. That is, the beam 1422 extending from the proximal cap 1413 to the distal cap 1417 maintains the rigidity of the system when fairly mild forces are applied as it is fixed at both ends and extends the length of the expanded cage. The rigidity of the beam 1422, however, is optimized to be sufficiently flexible when fairly significant force is applied to it (e.g., bending force of the endoscope). This rigidifying of the beam can be achieved in several ways. In some embodiments, the wire element which forms the rigidifying beam itself is sufficiently rigid to achieve the stability of the expanded cage. However, to further increase the rigidity, but preserve the desired flexibility, the rigidifying beam in alternate embodiments can have an increased thickness to further optimize the bending of the cage's elements such as beam 1422. As shown, in this embodiment, the diameter or (cross-sectional dimension if a non-circular beam is used) is greater than the diameter (or cross-sectional dimension if non-circular elements are used) of the flexible elements 1412, 1414, 1418, and/or 1420. In other embodiments, the rigidifying beam can be composed of a stiffer material than one or more of the other flexible elements. Such stiffer materials can include for example steel or plastic.

Note the flexible tool guides (tool channels) are not shown in FIGS. 40-42 for clarity, but flexible guides such as flexible guides 1270, 1271 of FIG. 33 can be utilized. Also, in this embodiment only a single actuator is provided for expansion of the retractor system 1415 since an actuator for rigidifying the structure is not necessary.

In all other respects, system 1410 is identical to system 1310.

Note as shown in FIG. 36, the retractor elements of the embodiments disclosed herein form an asymmetric cage to create a working space or working chamber for performance of the surgical procedure. The chamber facilitates instrument maneuverability, for example instruments' triangulation as described above. Note the asymmetric chamber causes a reconfiguration of the body lumen or working space without stretching the body lumen wall beyond a point when it can be injured, e.g., lacerated by the stretching force. Such reconfiguring can be appreciated by reference to FIG. 36 where the body lumen has changed from a substantially circular cross-sectional configuration to a somewhat oval shape configuration where the walls are elongated as shown. As can be appreciated, this increases the distance from the tips of the working instruments to the targeted tissue, such as the polyp C on the wall of the colon B. Thus, the retractor elements change the colon shape at the desired site to a narrower width, particularly at the bottom of the chamber, and taller in height (in the orientation of FIG. 36) to increase working space for the instruments thereby reconfiguring the colon lumen.

The retractor elements of the embodiments disclosed herein also stabilize the luminal wall motion which may be more prominent in the gastrointestinal tract. This may facilitate the surgical procedure, particularly in the gastrointestinal tract.

Note that the various embodiments of the cage described above are expandable to alter the working space within the body space or body lumen. As the cage is expanding, the working space around the target tissue, e.g., lesion, is increasing. More specifically, the distance between the instruments and the target tissue is increasing, hence, facilitating the instruments' maneuverability and ability to perform more advanced surgical techniques inside the lumen, e.g., tissue retraction, dissection, repair. As the cage expands it may press on and deflect at least a portion of the luminal wall. As a result, the shape of the lumen can be changed depending on the size and shape of the cage, the extent of its expansion and the size and shape of the body lumen. In smaller diameter body lumens, such as the bowel, the expansion of the cage may substantially reshape the body lumen as described above. This reshaping can also occur in larger diameter body lumens. However, it should also be appreciated that in certain larger diameter body lumens, such as the stomach, and especially when insufflation is utilized for the surgical procedure, the body lumen may not necessarily be reshaped. For example, the cage may only contact one side of the body lumen wall. However, even in this case, the expanded cage applies a radial force against the body wall to alter the working space. Therefore, whether the cage is used in small or larger diameter working spaces/lumens it advantageously moves at least one side of the wall to increase the distance between the tips of the instruments and the target tissue, thereby functioning as a working space expanding system to facilitate access and maneuverability as described in detail above. As can also be appreciated, the dynamic nature of the cage with its controlled expansion enables the system to function as an organizer to adjust and optimize the distance between the tips of the instruments and the target tissue. Also note that in larger diameter body lumens a symmetric cage might also be able to be utilized, although not optimal.

Note the endoscopic instruments can be used for partial tissue resection, for example, submucosal or subserosal resection. The endoscopic instruments could also be utilized for full thickness tissue resection. The instruments enable removal of the lesion with healthy tissue margins, thereby providing a complete, en-block removal of the pathological lesion.

In the systems described above, the user manually manipulates the components to expand the retractor elements of the cage, to move the tool channels and to move the endoscopic instruments within the tool channels (or directly through the catheter in the embodiments where the tool channels are not provided). However, it is also contemplated that in alternate embodiments, one or more of these movements can be robotically controlled. That is, expansion and collapse of the cage, slidable and rotational movement of the tool channels (flexible guides), slidable movement of the endoscopic instruments within the flexible guides (or within the catheter), and/or movement of the end effectors of the endoscopic instruments can be controlled by a robotics system.

Without intending to be limited to any theory or mechanism of action, the above teachings were provided to illustrate a sampling of all possible embodiments rather than a listing of the only possible embodiments. As such, it should be appreciated that there are several variations contemplated within the skill in the art that will also fall into the scope of the claims.

We claim:

1. A method, comprising:
   inserting a catheter into a body lumen of a patient, the catheter having a working space expanding system at a distal portion thereof;
   expanding the working space expanding system from a non-expanded insertion position to an expanded position to atraumatically contact a side wall of the body lumen and form an altered working space within the body lumen;
   inserting through the catheter a flexible outer sheath and a tissue retractor slidably disposed within the flexible outer sheath, the tissue retractor having a plurality of expandable petals, a distal portion of the flexible outer sheath movable to an angled position within the altered working space;
   exposing the petals from the flexible outer sheath such that the petals move from a collapsed insertion position to an expanded position within the altered working space; and
   either before or after exposing the petals from the flexible outer sheath, moving the flexible outer sheath axially to adjust the lateral extension of the tissue retractor within the altered working space.

2. The method of claim 1, further comprising: a) manipulating a proximal end of the tissue retractor such that one or more of the petals contacts and moves the side wall of the body lumen away from a tissue dissecting plane and b) dissecting a target tissue within the side wall of the body lumen with a dissecting instrument extending through the catheter and into the altered working space.

3. The method of claim 1, wherein the flexible outer sheath is independently rotatable and axially movable within the catheter.

4. The method of claim 1, wherein the flexible outer sheath extends through a first lumen of the catheter.

5. The method of claim 1, wherein the flexible outer sheath comprises a shape memory material.

6. The method of claim 4, wherein the catheter includes a second lumen to receive an endoscope therethrough.

7. The method of claim 1, wherein the petals comprise a shape memory material with a memorized position in the expanded position.

8. A method, comprising:
   inserting a catheter into a body lumen of a patient, the catheter having a working space expanding system at a distal portion thereof;
   expanding the working space expanding system from a non-expanded insertion position to an expanded position to atraumatically contact a side wall of the body lumen and form an altered working space within the body lumen;
   inserting a tissue retractor through the catheter, the tissue retractor having an outer member, an inner member and a plurality of expandable petals at a distal portion of the inner member, a distal portion of the outer member movable to an angled position within the altered working space;
   exposing the petals from the outer member such that the petals move from a collapsed insertion position to an expanded position within the altered working space;
   manipulating a proximal end of the tissue retractor such that one or more of the petals contacts and moves the side wall of the body lumen away from a tissue dissecting plane; and
   dissecting target tissue within the side wall of the body lumen with a dissecting instrument extending through the catheter and into the altered working space.

9. The method of claim 8, wherein the tissue retractor extends through a first lumen of the catheter.

10. The method of claim 8, , wherein the distal portion of the tissue retractor is movable to an angled position within the altered working space.

11. The method of claim 8, wherein the dissecting instrument guide is movable to an angled position within the altered working space.

12. The method of claim 8, further comprising controlling the extent of expansion of the petals of the tissue retractor.

13. The method of claim 8, further comprising, either before or after exposing the petals from the outer member, moving the outer member axially to adjust the lateral extension of the tissue retractor within the altered working space.

\* \* \* \* \*